US007112594B2

(12) United States Patent  (10) Patent No.: US 7,112,594 B2
Ushio et al.  (45) Date of Patent: Sep. 26, 2006

(54) FUSED BICYCLIC AMIDE COMPOUNDS AND MEDICINAL USE THEREOF

(75) Inventors: Hiroyuki Ushio, Tokyo (JP); Youichiro Naito, Tokyo (JP); Naoki Sugiyama, Tokyo (JP); Takafumi Kawaguchi, Tokyo (JP); Makio Ohtsuki, Tokyo (JP); Kenji Chiba, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 149 days.

(21) Appl. No.: 10/344,261

(22) PCT Filed: Aug. 9, 2001

(86) PCT No.: PCT/JP01/06852

§ 371 (c)(1),
(2), (4) Date: Apr. 29, 2003

(87) PCT Pub. No.: WO02/12189

PCT Pub. Date: Feb. 14, 2002

(65) Prior Publication Data

US 2003/0203909 A1 Oct. 30, 2003

(30) Foreign Application Priority Data

Aug. 9, 2000 (JP) ......................... 2000-241934

(51) Int. Cl.
A61K 31/445 (2006.01)
C07D 409/10 (2006.01)
C07D 211/06 (2006.01)

(52) U.S. Cl. .................... 514/324; 514/315; 514/323; 546/184; 546/192; 546/196; 546/200; 546/202; 544/106; 544/111; 544/358

(58) Field of Classification Search ................ 546/184, 546/192, 196, 200, 202; 514/315, 323, 324; 544/106, 111, 358
See application file for complete search history.

(56) References Cited

U.S. PATENT DOCUMENTS

| 3,413,308 | A |   | 11/1968 | Bockstahlev |         |
|-----------|---|---|---------|-------------|---------|
| 3,479,348 | A |   | 11/1969 | Yamamoto et al. |     |
| 4,145,364 | A |   | 3/1979  | Mulvey et al. |       |
| 4,179,578 | A |   | 12/1979 | Fleck et al. |        |
| 4,800,211 | A |   | 1/1989  | Tischler et al. |     |
| 6,015,829 | A |   | 1/2000  | Ishibuchi et al. | 514/404 |
| 6,069,151 | A |   | 5/2000  | Dyke et al. |         |
| 6,166,028 | A | * | 12/2000 | Bloom et al. | 514/277 |
| 6,207,693 | B1 |  | 3/2001  | Setoi et al. | 514/394 |
| 6,262,082 | B1 | * | 7/2001 | Bloom et al. | 514/336 |
| 6,555,561 | B1 | * | 4/2003 | Bloom et al. | 514/353 |
| 6,716,987 | B1 |  | 4/2004  | Ohshima et al. |      |

FOREIGN PATENT DOCUMENTS

| DE | 2441959 | 3/1975 |
| EP | 2892 | 7/1979 |
| EP | 23569 | 2/1981 |
| EP | 29992 | 6/1981 |
| EP | 594019 | 4/1994 |
| EP | 0 625 522 | 11/1994 |
| EP | 628038 | 12/1994 |
| EP | 797980 | 10/1997 |
| EP | 1 176 140 | 1/2002 |
| GB | 760750 | 11/1956 |
| JP | 6-298732 | 10/1994 |
| JP | 6-298732 | 11/1995 |
| JP | 2000-95767 | 4/2000 |
| JP | 2001-143635 | 5/2001 |
| WO | 91/05761 | 5/1991 |
| WO | 91/18902 | 12/1991 |
| WO | 94/27986 | 12/1994 |
| WO | 95/11885 | 5/1995 |
| WO | 96/30014 | 10/1996 |
| WO | 97/44036 | 11/1997 |
| WO | 97/44337 | 11/1997 |
| WO | 97/48697 | 12/1997 |
| WO | 98/2420 | 1/1998 |
| WO | 98/18765 | 5/1998 |
| WO | 98/20007 | 5/1998 |
| WO | 98/22452 | 5/1998 |

(Continued)

OTHER PUBLICATIONS

Eur. J. Med. Chem. Chim. Ther., (1985), 20 (2), pp. 187–189.

(Continued)

*Primary Examiner*—Golam M. M. Shameem
(74) *Attorney, Agent, or Firm*—Wenderoth, Lind & Ponack, L.L.P.

(57) ABSTRACT

Compounds represented by the following general formula (I) wherein ring A is benzene, cyclohexane, pyridine, piperidine, a derivative thereof, imidazole, a derivative thereof, etc.; the ring B represents benzene, cyclohexane, pyrrole or a derivative thereof, furan, thiophene, etc.; $R^1$, $R^2$ and $R^3$ represent each hydrogen, alkyl, halogen, hydroxyl, alkoxy, etc.; W represents hydrogen, alkyl or hydroxycarbonylalkyl; X represents halogen, cyano, nitro, etc.; X' represents hydrogen, halogen, etc.; and Y represents alkyl, hydroxyalkyl, hydroxycarbonylalkyl, aminoalkyl, etc.; salt thereof, and drugs comprising these compounds. Because of having an exellent effect of inhibiting activated lymphocyte proliferation, these compounds are usefull as preventives or remedies for various autoimmune diseases.

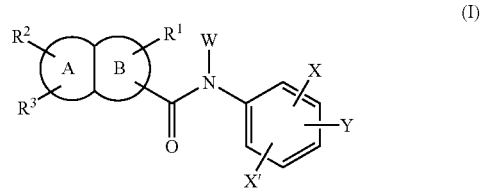

(I)

12 Claims, No Drawings

FOREIGN PATENT DOCUMENTS

| WO | 98/24771 | 6/1998 |
|---|---|---|
| WO | 98/28269 | 7/1998 |
| WO | 98/45255 | 10/1998 |
| WO | 99/15505 | 4/1999 |
| WO | 99/41239 | 8/1999 |
| WO | 99/45002 | 9/1999 |
| WO | 99/64423 | 12/1999 |
| WO | 00/06085 | 2/2000 |
| WO | 00/07980 | 2/2000 |
| WO | 00/07991 | 2/2000 |
| WO | 00/42213 | 7/2000 |
| WO | 00/47558 | 8/2000 |
| WO | 01/21615 | 3/2001 |
| WO | 01/28993 | 4/2001 |

OTHER PUBLICATIONS

Chemical Abstracts, vol. 92, Abstract No. 128647.
J. Pharm. Sci., (1975), 64 (6), pp. 1001–1005.
Chemical Abstracts, vol. 52, Abstract No. 13718c–e.
Chemical Abstracts, vol. 98, Abstract No. 53609.
J. Heterocycl. Chem., (1991), 28 (5), pp. 1309–1313.
J. Heterocycl. Chem., (1987), 24 (6), pp. 1589–1594.
Chemical Abstracts, vol. 106, ABstract No. 67157.
J. Svoboda et atl., "Synthesis and Biological Evaluation of New Antiinflammatory 1–Benzolhiophene–2–Carboxanilides", Collection of Czechoslovak Chemical Communications, vol. 65, No. 7, pp. 1082–1092, 2000.
K. L. Milkiewicz et al., "The Design, Synthesis and Activity of Non–ATP Competitive Inhibitors of $pp60^{osrc}$ Tyrosine Kinase. Part 2: Hydroxyindole Derivatives", Bioorganic & Medicinal Chemistry Letters, vol. 10, No. 5, pp. 483–486, Mar. 2000.
A. Taudou et al., "Recherche d'activite anti–parasitaire de carboxamido–2–benzopyrones–4", European Journal of Medicinal Cehmistry, vol. 22, pp. 583–585, 1987.

* cited by examiner

FUSED BICYCLIC AMIDE COMPOUNDS AND MEDICINAL USE THEREOF

TECHNICAL FIELD

The present invention relates to a pharmaceutical agent, particularly a fused bicyclic amide compound useful as an agent for the prophylaxis or treatment of autoimmune diseases and its use as a pharmaceutical agent.

BACKGROUND ART

It is considered that autoimmune diseases are induced because lymphocytes that inherently do not have self-reactivity have acquired autoreactivity or because autoreactive lymphocytes have not been deleted completely in thymus and the like. Of such diseases, rheumatoid arthritis (RA) is considered to be induced by immunoreaction of lymphocytes (particularly T cells and B cells) for type II collagen mostly present in one's own joints. It is a serious disease that accompanies infiltration of T cells and B cells into the joint part, activation and proliferation of these cells in the joint part, and with progression of symptoms, abnormal proliferation of synovial cells in the joint to result in destruction of the joint. In addition, because a great number of activated lymphocytes infiltrate into the joint tissues of RA patients, the activated lymphocytes are considered to play an important role in the establishment or progress of the disease state of RA.

It is generally known that, when lymphocytes are activated by an antigen, type 1 helper T cell (Th1 cell) in the lymphocytes produces cytokines, such as interleukin 2 (IL-2), interferon-γ (IFNγ) and the like, and the produced IL-2 and IFN-γ cause proliferation and differentiation of lymphocytes, particularly T cell. Because the IL-2 level is extremely low despite the presence of a great number of activated lymphocytes in the joint tissues of RA patients, the presence of a lymphocyte growth factor other than IL-2 has been predicted [Journal of Experimental Medicine, vol. 168, p. 1573 (1988)].

In recent years, interleukin 15 (IL-15) has been cloned as a new cytokine that promotes proliferation and differentiation of lymphocytes (T and B cell) [Science, vol. 264, p. 965, (1994)]. It has been clarified that IL-15 receptor consists of a chain specific to IL-15, β chain common to IL-15 and IL-2, and γ chain common to IL-15, IL-2, IL-4, IL-7, IL-9 and IL-13 receptors [EMBO Journal, vol. 13, p. 2822 (1994); EMBO Journal, vol. 14, p. 3654 (1995)]. It was also elucidated that a signal transduction pathway via tyrosine kinase, represented by JAK1 and JAK3, is present in the downstream of β chain and γ chain [Science, vol. 266, p. 1782 (1994)]. Therefore, it is expected that the pharmacological activity induced by the binding of IL-15 and IL-15 receptors should be the promotion of the proliferation of lymphocyte, which is of the same kind as that provided by the binding of IL-2 and IL-2 receptor. The IL-2 and IL-9 producing cell is T cell, particularly helper T cell activated by antigen, whereas the IL-7 producing cell is mainly stroma cell. The IL-15 producing cell has been reported to be macrophage, dendritic cell, synovial cell and the like [Science, vol. 264, p. 965 (1994)]. The presence of IL-15 at an extremely high concentration in the synovial fluid of RA patients has been recently reported, thereby suggesting the important role of IL-15 as a growth factor for the growth of activated lymphocytes in the joint part of RA. Furthermore, IL-15 has been reported to have many activities to promote migration of T cell into inflammatory sites, to activate memory T cell, promote production of inflammatory cytokines such as tumor necrosis factor (TNF)-α etc., and the like, besides the promotion of the proliferation of activated lymphocyte [Nature medicine, vol. 3, p. 189 (1997)], and its important role in the onset and the progress of various autoimmune diseases such as Crohn's disease, lupus nephritis in systemic lupus erythematosus and the like has been increasingly clarified.

From the foregoing, inhibition of the proliferation of IL-15-dependent activated lymphocyte is considered to be particularly effective for the improvement of the symptoms of autoimmune diseases represented by RA.

As conventional therapeutic agents of autoimmune diseases, particularly RA, pharmaceutical agents such as gold preparation, penicillamine, bucillamine, azathioprine, cyclophosphamide, methotrexate and the like have been widely used. These have an effect of inhibition of the proliferation of synovial cells in joints, but also have an antagonistic and inhibitory action on the metabolism of nucleic acid. As a result, a long-term dose thereof causes manifestation of side effects such as dyshematopoiesis, digestive disturbance and the like at high frequency, and is also associated with problems such as easy infection and the like. Accordingly, they are not therapeutically satisfactory. In addition, while adrenocorticosteroid is effective for these diseases, the use of this agent is associated with the expression of grave side effects such as moon face, degradation of adrenal gland function, avascular necrosis of the femoral head, and the like. It has been reported that, while leflunomide approved in the US as an antirheumatic drug shows a superior therapeutic effect, it shows a long half-life in blood and causes side effects of digestive disturbance, liver impairment, rash and the like [The Lancet, vol. 353, pp. 259–266 (1999)], and a clinically superior therapeutic agent is desired.

Thus, the need for a therapeutic agent for autoimmune diseases such as RA and the like, which has a superior treatment effect as compared to conventional pharmaceutical agents, and which is associated with less side effects is considered to be extremely high.

As mentioned above, the proliferation of activated lymphocytes in joint tissues is deeply involved in the progress of arthritis in RA, and the involvement of IL-15 in the proliferation of activated lymphocyte has been suggested. Thus, a compound that inhibits signal transduction from IL-15 receptors (β, γ chain commonly found in IL-2, and γ chain commonly found in IL-2, IL-4, IL-7, IL-9, IL-13 and IL-15) via tyrosine kinase is expected to show a superior effect for the prophylaxis or treatment of autoimmune diseases such as rheumatoid arthritis and the like. Moreover, a compound that inhibits, besides the aforementioned action, production of IL-15 itself or production of inflammatory cytokines induced by IL-15, such as TNF-α and the like, is considered to show a more superior effect in the prophylaxis or treatment of autoimmune diseases such as rheumatoid arthritis and the like. However, there has been no report so far on the study of a compound having inhibitory effects on the proliferation of activated lymphocyte as a therapeutic agent of autoimmune diseases or a therapeutic agent of RA, taking note of IL-15.

Journal of Medicinal Chemistry, vol. 21, pp. 1178–1181 (1978) discloses 1-hydroxynaphthamide derivative as an anthelmintic, and Journal of Medicinal Chemistry, vol. 20, pp. 826–829 (1977) and WO 94/05649 disclose a salicylamide derivative and a hydroxycoumarin derivative as antibacterial agent, respectively. In addition, WO 99/41239 discloses quinoline or indole derivative as a B cell inhibitor. However, inhibitory effects on the proliferation of activated lymphocyte of these compounds taking note of IL-15 have not been disclosed at all.

The present inventors have intensively studied in view of the above-mentioned situation, and as a result, found that a fused bicyclic amide compound represented by the following formula and pharmaceutically acceptable salts thereof inhibit a cytokine response that induces proliferation, differentiation and the like of various immunocompetent cells such as lymphocytes (T cell, B cell), macrophage and the like, due to the addition of cytokines such as IL-2, IL-4, IL-7, IL-9, IL-15 and the like, in the presence or absence of antigen or mitogen. Particularly, they have found that the compound and the salt inhibit IL-15-dependent proliferation of activated lymphocytes and production of inflammatory cytokines induced by IL-15, or IL-1, IL-6, IL-12, IL-15, IL-18, TNF-α and the like, which resulted in the completion of the present invention.

DISCLOSURE OF THE INVENTION

Accordingly, the present invention provides the following.

(1) A fused bicyclic amide compound represented by the formula (I)

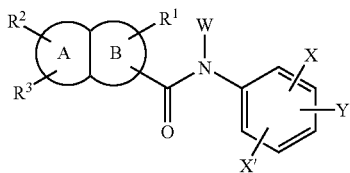

(I)

wherein
$R^1$, $R^2$ and $R^3$ are the same or different and each is hydrogen, alkyl, halogen, hydroxyl group, alkoxy or amino optionally having substituents;
ring A is benzene, cyclohexane, pyridine, piperidine or a derivative thereof, imidazole or a derivative thereof or 1,3-dioxolane, which is represented by the formula

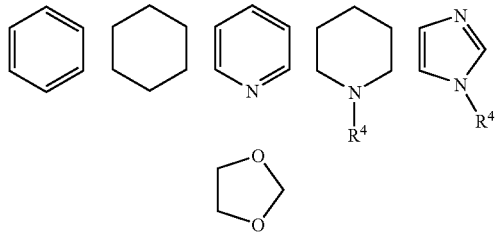

wherein $R^4$ is hydrogen, alkyl or acyl;
ring B is benzene, cyclohexane, pyrrole or a derivative thereof, furan, thiophene, pyridine, pyrazine, 5,6-dihydro-2H-pyran-4-one, 2,3,5,6-tetrahydro-2H-pyran-4-one or 5,6-dihydro-2H-pyran-2-one represented by the formula

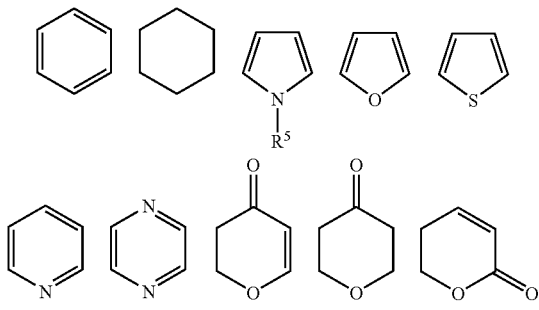

wherein $R^5$ is hydrogen, alkyl, alkoxycarbonylalkyl, hydroxycarbonylalkyl, acyloxyalkyl or hydroxyalkyl;

W is hydrogen, alkyl or hydroxycarbonylalkyl;
X is halogen, cyano, nitro, amino, alkyl, alkoxy, carboxy, alkoxycarbonyl, carbamoyl, alkenyl, alkynyl or haloalkyl;
X' is hydrogen, halogen, cyano or nitro; and
Y is halogen, alkyl, hydroxyalkyl, hydroxycarbonylalkyl, aminoalkyl optionally having substituents, hydroxyl group, alkoxy, haloalkoxy, aryloxy, cycloalkyloxy, azacycloalkyloxy optionally having substituents, hydroxyalkoxy, hydroxycarbonylalkoxy, aminoalkoxy optionally having substituents, mercapto, alkylthio, hydroxyalkylthio, hydroxycarbonylalkylthio, aminoalkylthio optionally having substituents or a group $N(Z^2)(Z^3)$ (wherein $Z^2$ and $Z^3$ are the same or different and each is hydrogen, alkyl, hydroxyalkyl or aminoalkyl optionally having substituents or $Z^2$ and $Z^3$ are groups that form, together with the adjacent nitrogen atom, cyclic amine optionally having, in the ring, one or two from oxygen atom, sulfur atom and nitrogen atom),
or a pharmaceutically acceptable salt thereof.

(2) The fused bicyclic amide compound described in the aforementioned (1), wherein the ring A-B is naphthalene, benzo[b]thiophene, benzo[b]furan, thieno[2,3-b]pyridine, 4,5,6,7-tetrahydrobenzo[b]thiophene, 4,5,6,7-tetrahydrothieno[2,3-c]pyridine or a derivative thereof ($R^4$ is hydrogen, alkyl or acyl), quinoline, or indole or a derivative thereof ($R^5$ is hydrogen, alkyl, alkoxycarbonylalkyl, hydroxycarbonylalkyl, acyloxyalkyl or hydroxyalkyl) represented by the following formula

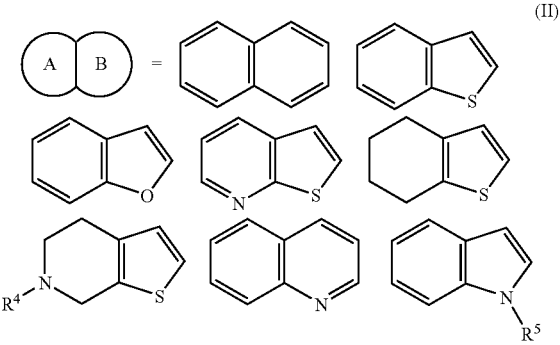

(II)

X' is hydrogen, and $R^1$, $R^2$, $R^3$, W, X and Y are as defined in the aforementioned (1),
or a pharmaceutically acceptable salt thereof.

(3) The fused bicyclic amide compound described in the aforementioned (1), wherein X' is hydrogen, X is halogen, cyano, nitro or haloalkyl that substitutes the 3-position of phenyl group, and $R^1$, $R^2$, $R^3$, $R^4$, $R^5$, W and Y are as defined in the aforementioned (1) and Y substitutes the 2-position or 4–6 position of phenyl group, or a pharmaceutically acceptable salt thereof.

(4) The fused bicyclic amide compound described in the aforementioned (1), wherein the ring A-B is benzo[b]thiophene, benzo[b]furan, thieno[2,3-b]pyridine, or indole or a derivative thereof ($R^5$ is hydrogen, alkyl, alkoxycarbonylalkyl, acyloxyalkyl or hydroxyalkyl) represented by the following formula

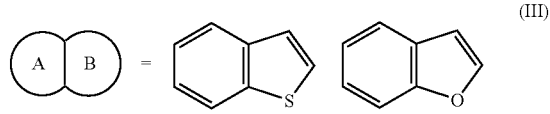

(III)

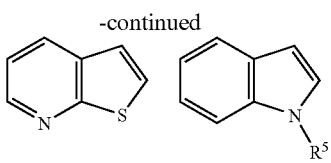

W is hydrogen or alkyl, X is halogen, cyano, nitro or haloalkyl that substitutes the 3-position of phenyl group, X' is hydrogen, and $R^1$, $R^2$, $R^3$ and Y are as defined in the aforementioned (1) and Y substitutes the 4-position of phenyl group, or a pharmaceutically acceptable salt thereof.

(5) The fused bicyclic amide compound described in the aforementioned (1), wherein the ring A-B is benzo[b]thiophene or indole or a derivative thereof ($R^5$ is hydrogen, alkyl, alkoxycarbonylalkyl, acyloxyalkyl or hydroxyalkyl) of the following formula

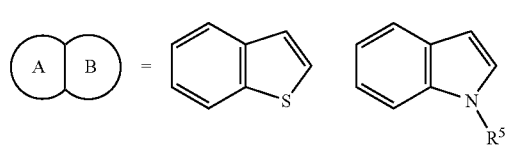

(IV)

W is hydrogen or alkyl, X is halogen, cyano, nitro or haloalkyl that substitutes the 3-position of phenyl group, X' is hydrogen, and $R^1$, $R^2$, $R^3$ and Y are as defined in the aforementioned (1) and Y substitutes the 4-position of phenyl group, or a pharmaceutically acceptable salt thereof.

(6) The fused bicyclic amide compound described in the aforementioned (1), which is selected from
N-(3-cyano-4-neopentyloxyphenyl)benzo[b]thiophene-2-carboxamide,
N-(3-cyano-4-phenoxyphenyl)-5-fluoro-2-methyl-1H-indole-3-carboxamide,
N-[3-cyano-4-(4-(2-hydroxyethyl)piperazin-1-yl)phenyl]benzo[b]thiophene-2-carboxamide,
N-[3-cyano-4-(4-(2-hydroxyethyl)piperidin-1-yl)phenyl]benzo[b]thiophene-2-carboxamide,
N-[3-cyano-4-(4-morpholinopiperidin-1-yl)phenyl]benzo[b]thiophene-2-carboxamide,
N-[3-cyano-4-(4-piperidinopiperidin-1-yl)phenyl]benzo[b]thiophene-2-carboxamide,
N-[3-cyano-4-(4-(3,4,5,6-tetrahydro-2H-pyran-4-yl)piperazin-1-yl)phenyl]benzo[b]thiophene-2-carboxamide,
N-(3-cyano-4-neopentyloxyphenyl)-3-hydroxy-6-isopropylthieno[2,3-b]pyridine-2-carboxamide,
N-[3-cyano-4-(4-hydroxypiperidin-1-yl)phenyl]-5-fluoro-2-methyl-1H-indole-3-carboxamide,
N-[3-cyano-4-(4-hydroxypiperidin-1-yl)phenyl]benzo[b]thiophene-2-carboxamide, and
N-{3-cyano-4-[4-(2-hydroxyethyl)piperidin-1-yl]phenyl}benzo[b]furan-2-carboxamide,
or a pharmaceutically acceptable salt thereof.

(7) A pharmaceutical composition comprising the fused bicyclic amide compound described in any of the aforementioned (1) to (6) or a pharmaceutically acceptable salt thereof, and a pharmaceutically acceptable carrier.

(8) A pharmaceutical agent comprising the fused bicyclic amide compound described in any of the aforementioned (1) to (6) or a pharmaceutically acceptable salt thereof.

(9) An inhibitor on the proliferation of activated lymphocyte comprising the fused bicyclic amide compound described in any of the aforementioned (1) to (6) or a pharmaceutically acceptable salt thereof as an active ingredient.

(10) The inhibitor on the proliferation of activated lymphocyte described in the aforementioned (9), which is IL-2, IL-4, IL-7, IL-9, IL-13 or IL-15-dependent.

(11) A phosphorylation inhibitor of tyrosine kinase involved in signal transduction in the downstream of common β chain, which is a receptor subunit common to IL-15 and IL-2, and/or common γ chain, which is a receptor subunit common to IL-2, IL-4, IL-7, IL-9, IL-13 and IL-15, which comprises the fused bicyclic amide compound described in any of the aforementioned (1) to (6) or a pharmaceutically acceptable salt thereof as an active ingredient.

(12) A cytokine production inhibitor comprising the fused bicyclic amide compound described in any of the aforementioned (1) to (6) or a pharmaceutically acceptable salt thereof as an active ingredient.

(13) An IL-2, IL-4, IL-13 or IFN-γ production inhibitor comprising the fused bicyclic amide compound described in any of the aforementioned (1) to (6) or a pharmaceutically acceptable salt thereof as an active ingredient.

(14) An IL-1, IL-6, IL-12, IL-15, IL-18 or TNF-α production inhibitor comprising the fused bicyclic amide compound described in any of the aforementioned (1) to (6) or a pharmaceutically acceptable salt thereof as an active ingredient.

(15) An agent for the prophylaxis or treatment of a disease caused by the proliferation of lymphocyte, which comprises the fused bicyclic amide compound described in any of the aforementioned (1) to (6) or a pharmaceutically acceptable salt thereof as an active ingredient.

(16) An agent for the prophylaxis or treatment of an autoimmune disease, which comprises the fused bicyclic amide compound described in any of the aforementioned (1) to (6) or a harmaceutically acceptable salt thereof as an active ingredient.

(17) A combination composition comprising the fused bicyclic amide compound described in any of the aforementioned (1) to (6) or a pharmaceutically acceptable salt thereof, and one or more drugs selected from antirheumatic drug, immunosuppressant, steroidal drug and nonsteroidal antiinflammatory drug.

(18) The combination composition described in the aforementioned (17), wherein the antirheumatic drug is selected from gold preparation, penicillamine, bucillamine, lobenzarit, actarit and salazosulfapyridine.

(19) The combination composition described in the aforementioned (17), wherein the immunosuppressant is selected from azathioprine, cyclophosphamide, methotrexate, brequinar sodium, deoxyspergualin, mizoribine, 2-morpholinoethyl ester of mycophenolic acid, cyclosporine, rapamycin, tacrolimus hydrate, leflunomide, OKT-3, anti-TNF-α antibody, anti-IL-6 antibody and FTY720.

(20) The combination composition described in the aforementioned (17), wherein the steroidal drug is selected from prednisolone, methylprednisolone, dexamethasone and hydrocortisone.

(21) The combination composition described in the aforementioned (17), wherein the nonsteroidal antiinflammatory drug is selected from aspirin, indomethacin, indomethacinfarnesyl, diclofenac sodium, alclofenac, amfenac sodium, ibuprofen, ketoprofen, loxoprofen sodium, naproxen, pranoprofen, zaltoprofen, mefenamic acid, flufenamic acid, tolfenamic acid, phenylbutazone, ketophenylbutazone, piroxicam, tenoxicam and ampiroxicam.

(22) An action potentiator of one or more drugs selected from antirheumatic drug, immunosuppressant, steroidal drug and nonsteroidal antiinflammatory drug, which comprises the fused bicyclic amide compound described in any of the aforementioned (1) to (6) or a pharmaceutically acceptable salt thereof.
(23) The action potentiator described in the aforementioned (22), wherein the antirheumatic drug is selected from gold preparation, penicillamine, bucillamine, lobenzarit, actarit and salazosulfapyridine.
(24) The action potentiator described in the aforementioned (22), wherein the immunosuppressant is selected from azathioprine, cyclophosphamide, methotrexate, brequinar sodium, deoxyspergualin, mizoribine, 2-morpholinoethyl ester of mycophenolic acid, cyclosporine, rapamycin, tacrolimus hydrate, leflunomide, OKT-3, anti-TNF-α antibody, anti-IL-6 antibody and FTY720.
(25) The action potentiator described in the aforementioned (22), wherein the steroidal drug is selected from prednisolone, methylprednisolone, dexamethasone and hydrocortisone.
(26) The action potentiator described in the aforementioned (22), wherein the nonsteroidal antiinflammatory drug is selected from aspirin, indomethacin, indomethacinfarnesyl, diclofenac sodium, alclofenac, amfenac sodium, ibuprofen, ketoprofen, loxoprofen sodium, naproxen, pranoprofen, zaltoprofen, mefenamic acid, flufenamic acid, tolfenamic acid, phenylbutazone, ketophenylbutazone, piroxicam, tenoxicam and ampiroxicam.
(27) A cyclic amino compound represented by the formula (Va)

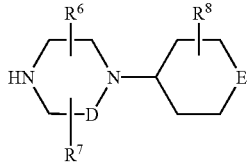

(Va)

wherein $R^6$, $R^7$ and $R^8$ are the same or different and each is hydrogen, alkyl, hydroxyl group, alkoxy or hydroxyalkyl, D is methylene or ethylene and E is oxygen atom or sulfur atom, or a pharmaceutically acceptable salt thereof.
(28) A 3-cyanoaniline compound represented by the formula (Vb)

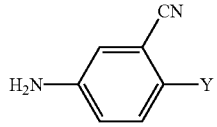

(Vb)

wherein Y is halogen, alkyl, hydroxyalkyl, hydroxycarbonylalkyl, aminoalkyl optionally having substituents, hydroxyl group, alkoxy, haloalkoxy, aryloxy, cycloalkyloxy, azacycloalkyloxy optionally having substituents, hydroxyalkoxy, hydroxycarbonylalkoxy, aminoalkoxy optionally having substituents, mercapto, alkylthio, hydroxyalkylthio, hydroxycarbonylalkylthio, aminoalkylthio optionally having substituents or a group $N(Z^2)(Z^3)$
(wherein $Z^2$ and $Z^3$ are the same or different and each is hydrogen, alkyl, hydroxyalkyl or aminoalkyl optionally having substituents, or $Z^2$ and $Z^3$ are groups that form, together with the adjacent nitrogen atom, cyclic amine optionally having, in the ring, one or two from oxygen atom, sulfur atom and nitrogen atom), or a pharmaceutically acceptable salt thereof.

DETAILED DESCRIPTION OF THE INVENTION

The present invention aims at providing a fused bicyclic amide compound and a pharmaceutically acceptable salt thereof, having inhibitory effects on the proliferation of activated lymphocyte taking note of IL-15. As used herein, by the inhibitory effects on the proliferation of activated lymphocyte taking note of IL-15 is meant inhibitory effects on the proliferation of IL-15-dependent activated lymphocyte and encompasses inhibitory effects on the proliferation of IL-2, IL-4, IL-7, IL-9 or IL-13-dependent activated lymphocyte, that are cytokines closely related to IL-15. Moreover, the present invention aims at inhibition of signal transduction from IL-15 receptors (common β chain, which is a receptor subunit common to IL-15, and IL-2 and/or common γ chain, which is a receptor subunit common to IL-2, IL-4, IL-7, IL-9, IL-13 and IL-15), inhibition of the pathway via tyrosine kinase in the course of signal transduction, and provision of a compound that inhibits the production of IL-15 and inflammatory cytokines (IL-1, IL-6, IL-12, IL-15, IL-18 and TNF-α etc.) induced by IL-15.

The substituents represented by each symbol in the present specification are explained in the following.

The alkyl for $R^1$, $R^2$, $R^3$, $R^4$, $R^5$, $R^6$, $R^7$ and $R^8$ is straight chain or branched chain alkyl having 1 to 4 carbon atoms, such as methyl, ethyl, propyl, isopropyl, butyl, isobutyl, tertiary butyl and the like.

The halogen for $R^1$, $R^2$ and $R^3$ is fluorine, chlorine, bromine or iodine.

The alkoxy for $R^1$, $R^2$, $R^3$, $R^6$, $R^7$ and $R^8$ is straight chain or branched chain alkoxy having 1 to 4 carbon atoms, such as methoxy, ethoxy, propoxy, isopropoxy, butoxy, tertiary butoxy and the like.

The amino optionally having substituents for $R^1$, $R^2$ and $R^3$ may be mono- or di-substituted by a substituent selected from straight chain or branched chain alkyl having 1 to 4 carbon atoms (as defined above), acyl having 1 to 4 carbon atoms (formyl, acetyl, propionyl and the like), aminocarbonyl and benzoyl, as a substituent and is exemplified by amino, methylamino, dimethylamino, ethylamino, diethylamino, formylamino, acetylamino, propionylamino, ureido and benzoylamino.

The acyl for $R^4$ is exemplified by acyl having 1 to 4 carbon atoms (formyl, acetyl, propionyl and the like) and benzoyl.

The hydroxycarbonylalkyl for $R^5$ is straight chain or branched chain alkyl having 1 to 4 carbon atoms (as defined above), which is substituted by hydroxycarbonyl, and is exemplified by hydroxycarbonylmethyl, 2-hydroxycarbonylethyl, 3-hydroxycarbonylpropyl, 4-hydroxycarbonylbutyl and the like.

The alkoxycarbonylalkyl for $R^5$ is straight chain or branched chain alkyl having 1 to 4 carbon atoms (as defined above), which is substituted by alkoxycarbonyl, wherein the alkoxy moiety is straight chain or branched chain alkoxy having 1 to 4 carbon atoms (as defined above), and is exemplified by methoxycarbonylmethyl, methoxycarbonylethyl, methoxycarbonylpropyl, methoxycarbonylbutyl, ethoxycarbonylmethyl, propoxycarbonylmethyl, isopropoxycarbonylmethyl, butoxycarbonylmethyl and the like, preferably ethoxycarbonylmethyl.

The acyloxyalkyl for $R^5$ is straight chain or branched chain alkyl having 1 to 4 carbon atoms (as defined above), which is substituted by acyloxy having 1 to 4 carbon atoms (formyloxy, acetyloxy, propionyloxy, butyryloxy and the like), and is exemplified by formyloxymethyl, 2-formyloxyethyl, acetyloxymethyl, 2-acetyloxyethyl, 3-acetyloxypropyl, 4-acetyloxybutyl, propionyloxymethyl and the like.

The hydroxyalkyl for $R^5$, $R^6$, $R^7$ and $R^8$ is straight chain or branched chain alkyl having 1 to 4 carbon atoms (as defined above), which is substituted by hydroxyl group, and is exemplified by hydroxymethyl, 2-hydroxyethyl, 3-hydroxypropyl, 4-hydroxybutyl and the like.

The alkyl for W is straight chain or branched chain alkyl having 1 to 4 carbon atoms, and is exemplified by methyl, ethyl, propyl, isopropyl, butyl and the like, preferably methyl and ethyl.

The hydroxycarbonylalkyl for W is straight chain or branched chain alkyl having 1 to 4 carbon atoms (as defined above), which is substituted by hydroxycarbonyl, and is exemplified by hydroxycarbonylmethyl, 2-hydroxycarbonylethyl, 3-hydroxycarbonylpropyl, 4-hydroxycarbonylbutyl and the like, preferably hydroxycarbonylmethyl and 3-hydroxycarbonylpropyl.

The halogen for X is fluorine, chlorine, bromine or iodine, preferably chlorine and bromine.

The alkyl for X is straight chain or branched chain alkyl having 1 to 6 carbon atoms, and is exemplified by methyl, ethyl, propyl, isopropyl, butyl, isobutyl, tertiary butyl, pentyl, isopentyl, neopentyl, hexyl and the like. Preferred is alkyl having 1 to 3 carbon atoms, particularly preferably methyl.

The alkoxy for X is straight chain or branched chain alkoxy having 1 to 6 carbon atoms, and is exemplified by methoxy, ethoxy, propoxy, isopropoxy, butoxy, isobutoxy, tertiary butoxy, pentyloxy, isopentyloxy, neopentyloxy, hexyloxy and the like. Of these, preferred is alkoxy having 1 to 3 carbon atoms.

The alkenyl for X is straight chain or branched chain alkenyl having 2 to 4 carbon atoms, and is exemplified by ethenyl, 1-propenyl, 1-butenyl and the like, particularly preferably ethenyl.

The haloalkyl for X is straight chain or branched chain haloalkyl having 1 to 4 carbon atoms, and is exemplified by fluoromethyl, chloromethyl, bromomethyl, trifluoromethyl, 2-fluoroethyl, 2-chloromethyl, 2,2,2-trifluoroethyl and the like, particularly preferably trifluoromethyl.

The alkoxycarbonyl for X is alkoxycarbonyl wherein the alkoxy moiety is straight chain or branched chain alkoxy having 1 to 4 carbon atoms (as defined above), and is exemplified by methoxycarbonyl, ethoxycarbonyl, propoxycarbonyl, isopropoxycarbonyl, butoxycarbonyl, tertiary butoxycarbonyl and the like.

The alkynyl for X is straight chain or branched chain alkynyl having 2 to 4 carbon atoms, and is exemplified by ethynyl, 1-propynyl, 1-butynyl and the like, particularly preferably ethynyl.

The halogen for X' is fluorine, chlorine, bromine or iodine, preferably chlorine.

The halogen for Y is fluorine, chlorine, bromine or iodine, preferably chlorine and bromine.

The alkyl for Y is straight chain or branched chain alkyl having 1 to 6 carbon atoms, and is exemplified by methyl, ethyl, propyl, isopropyl, butyl, isobutyl, tertiary butyl, pentyl, isopentyl, neopentyl, hexyl, isohexyl, neohexyl and the like. Of these, preferred is alkyl having 4 to 6 carbon atoms.

The hydroxyalkyl for Y is straight chain or branched chain alkyl having 1 to 4 carbon atoms (as defined above), which is substituted by hydroxyl group, and is exemplified by hydroxymethyl, 2-hydroxyethyl, 3-hydroxypropyl, 4-hydroxybutyl and the like.

The hydroxycarbonylalkyl for Y is straight chain or branched chain alkyl having 1 to 4 carbon atoms (as defined above), which is substituted by hydroxycarbonyl, and is exemplified by hydroxycarbonylmethyl, 2-hydroxycarbonylethyl, 3-hydroxycarbonylpropyl, 4-hydroxycarbonylbutyl and the like.

The aminoalkyl optionally having substituents for Y is straight chain or branched chain alkyl having 1 to 4 carbon atoms (as defined above), which is substituted by amino group, wherein the amino group may be mono- or di-substituted by a substituent such as straight chain or branched chain alkyl having 1 to 4 carbon atoms (as defined above), acyl having 1 to 4 carbon atoms (as defined above) and benzoyl and the like. Specific examples thereof include aminomethyl, 2-aminoethyl, dimethylaminomethyl, 2-diethylaminomethyl, formylaminomethyl, acetylaminomethyl, 2-formylaminoethyl, 2-acetylaminoethyl, benzoylaminomethyl and the like. The amino group may form, cyclic amine that may have, in the ring, one or two from oxygen atom, sulfur atom and nitrogen atom, and is exemplified by pyrrolidine, piperidine optionally having substituents, homopiperidine, piperazine optionally having substituents, homopiperazine optionally having substituents, morpholine, thiomorpholine and the like. Specific examples thereof include piperidinomethyl, 2-piperidinoethyl, morpholinomethyl, 2-morpholinoethyl, thiomorpholinomethyl, piperazinomethyl, (4-morpholinopiperidin-1-yl)methyl and the like.

The alkoxy for Y is straight chain or branched chain alkoxy having 1 to 6 carbon atoms, and is exemplified by methoxy, ethoxy, propoxy, isopropoxy, butoxy, isobutoxy, tertiary butoxy, pentyloxy, isopentyloxy, neopentyloxy, hexyloxy, isohexyloxy, neohexyloxy and the like. Of these, preferred is alkoxy having 4 to 6 carbon atoms.

The haloalkoxy for Y is straight chain or branched chain alkoxy having 1 to 4 carbon atoms (as defined above), which is substituted by halogen (as defined above), and is exemplified by fluoromethoxy, chloromethoxy, 2-fluoroethoxy, 2,2,2-trifluoroethoxy and the like, with preference given to 2,2,2-trifluoroethoxy.

The aryloxy for Y is that wherein the aryl moiety is aryl having 6 to 14 carbon atoms, and is exemplified by phenoxy, naphthyloxy and the like, with preference given to phenoxy.

The cycloalkyloxy for Y is cycloalkyloxy having 3 to 6 carbon atoms, and is exemplified by cyclopentyloxy, cyclohexyloxy and the like, with preference given to cyclohexyloxy.

The azacycloalkyloxy optionally having substituents for Y is that having 3 to 6 ring-constituting atoms, and is exemplified by pyrrolidin-3-yloxy, piperidin-4-yloxy and the like, with preference given to piperidin-4-yloxy. The substituent is exemplified by arylalkyl wherein the alkyl moiety is straight chain or branched chain alkyl having 1 to 4 carbon atoms (as defined above) and the aryl moiety is aryl having 6 to 14 carbon atoms (as defined above), straight chain or branched chain alkyl having 1 to 4 carbon atoms (as defined above) and the like. Specific examples thereof include piperidin-4-yloxy, 1-methylpiperidin-4-yloxy, 1-ethylpiperidin-4-yloxy, 1-benzylpiperidin-4-yloxy, pyrrolidin-3-yloxy, 1-methylpyrrolidin-3-yloxy, 1-ethylpyrrolidin-3-yloxy, 1-benzylpyrrolidin-3-yloxy and the like, with preference given to 1-benzylpiperidin-4-yloxy.

The hydroxyalkoxy for Y is straight chain or branched chain alkoxy having 3 to 6 carbon atoms, which is substituted by hydroxy, and is exemplified by 3-hydroxypropoxy, 3-hydroxy-2,2-dimethylpropoxy, 1-methyl-1-hydroxyethoxy, 4-hydroxybutoxy, 5-hydroxypentyloxy and 6-hydroxyhexyloxy.

The hydroxycarbonylalkoxy for Y is straight chain or branched chain alkoxy having 1 to 4 carbon atoms (as defined above), which is substituted by hydroxycarbonyl, and is exemplified by hydroxycarbonylmethoxy, 2-hydroxycarbonylethoxy, 3-hydroxycarbonylpropoxy and 4-hydroxycarbonylbutoxy.

The aminoalkoxy optionally having substituents for Y is straight chain or branched chain alkoxy having 1 to 6 carbon atoms (as defined above), which is substituted by amino, wherein the amino group may be mono- or di-substituted by a substituent such as straight chain or branched chain alkyl having 1 to 4 carbon atoms (as defined above), acyl having 1 to 4 carbon atoms (as defined above), benzoyl and the like. The amino group may form a cyclic amine that may have, in the ring, one or two from oxygen atom, sulfur atom and nitrogen atom, and is exemplified by pyrrolidine, piperidine optionally having substituents, homopiperidine, piperazine optionally having substituents, homopiperazine optionally having substituents, morpholine, thiomorpholine and the like. Specific examples thereof include aminomethoxy, aminoethoxy, aminopropoxy, methylaminomethoxy, dimethylaminomethoxy, 2-dimethylaminoethoxy, formylaminomethoxy, acetylaminomethoxy, propionylaminomethoxy, benzoylaminomethoxy, morpholinomethoxy, 2-morpholinoethoxy, 3-morpholinopropoxy, 2,2-dimethyl-3-morpholinopropoxy, 4-morpholinobutoxy, 5-morpholinopentyloxy, 6-morpholinohexyloxy, thiomorpholinomethoxy, 2-thiomorpholinoethoxy, 3-thiomorpholinopropoxy, 2,2-dimethyl-3-thiomorpholinopropoxy, 4-thiomorpholinobutoxy, 5-thiomorpholinopentyloxy, 6-thiomorpholinohexyloxy, piperidinomethoxy, 2-piperidinoethoxy, 3-piperidinopropoxy, 2,2-dimethyl-3-piperidinopropoxy, 4-piperidinobutoxy, 5-piperidinopentyloxy, 6-piperidinohexyloxy, piperazinomethoxy, 2-piperazinoethoxy, 3-piperazinopropoxy, 2,2-dimethyl-3-piperazinopropoxy, 4-piperazinobutoxy, 5-piperazinopentyloxy, 6-piperazinohexyloxy, 2-pyrrolidinoethoxy, 3-pyrrolidinopropoxy and the like of these, 2-dimethylaminoethoxy, 4-morpholinobutoxy, 3-morpholinopropoxy, 2-morpholinoethoxy, morpholinomethoxy and 2,2-dimethyl-3-morpholinopropoxy are preferable.

The alkylthio for Y is that wherein the alkyl moiety is straight chain or branched chain alkyl having 0.1 to 6 carbon atoms (as defined above), and is exemplified by methylthio, ethylthio, propylthio, n-butylthio, pentylthio, neopentylthio, hexylthio and the like.

The hydroxyalkylthio for Y is that wherein the alkyl moiety is straight chain or branched chain alkyl having 1 to 6 carbon atoms (as defined above), and is exemplified by hydroxymethylthio, 2-hydroxyethylthio, 3-hydroxypropylthio, 4-hydroxybutylthio, 5-hydroxypentylthio and 6-hydroxyhexylthio.

The hydroxycarbonylalkylthio for Y is that wherein the alkyl moiety is straight chain or branched chain alkyl having 1 to 4 carbon atoms (as defined above), and is exemplified by hydroxycarbonylmethylthio, 2-hydroxycarbonylethylthio, 3-hydroxycarbonylpropylthio and 4-hydroxycarbonylbutylthio.

The aminoalkylthio optionally having substituents for Y is that wherein the alkyl moiety is straight chain or branched chain alkyl having 1 to 6 carbon atoms (as defined above), wherein the amino group may be mono- or di-substituted by a substituent such as straight chain or branched chain alkyl having 1 to 4 carbon atoms (as defined above), acyl having 1 to 4 carbon atoms (as defined above), benzoyl and the like. The amino group may form a cyclic amine that may have, in the ring, one or two from oxygen atom, sulfur atom and nitrogen atom in the ring, and is exemplified by pyrrolidine, piperidine substituent optionally having substituents, homopiperidine, piperazine optionally having substituents, homopiperazine optionally having substituents, morpholine, thiomorpholine and the like. Specific examples thereof include aminomethylthio, 2-aminoethylthio, 3-aminopropylthio, 4-aminobutylthio, dimethylaminomethylthio, diethylaminomethylthio, 2-dimethylaminoethylthio, 3-dimethylaminopropylthio, 4-dimethylaminobutylthio and the like, formylaminomethylthio, 2-formylaminoethylthio, acetylaminomethylthio, 2-acetylaminoethylthio, benzoylaminomethylthio, 2-benzoylaminoethylthio, morpholinomethylthio, 2-morpholinoethylthio, 3-morpholinopropylthio, 4-morpholinobutylthio, 5-morpholinopentylthio, 6-morpholinohexylthio, thiomorpholinomethylthio, 2-thiomorpholinoethylthio, 3-thiomorpholinopropylthio, 4-thiomorpholinobutylthio, 5-thiomorpholinopentylthio, 6-thiomorpholinohexylthio, piperidinomethylthio, 2-piperidinoethylthio, 3-piperidinopropylthio, 4-piperidinobutylthio, 5-piperidinopentylthio, 6-piperidinohexylthio, piperazinomethylthio, 2-piperazinoethylthio, 3-piperazinopropylthio, 4-piperazinobutylthio, 5-piperazinopentylthio, 6-piperazinohexylthio, 2-pyrrolidinoethylthio and 3-pyrrolidinopropylthio.

The alkyl for $Z^2$ and $Z^3$ is straight chain or branched chain alkyl having 1 to 4 carbon atoms, and is exemplified by methyl, ethyl, propyl, isopropyl, butyl, isobutyl, tertiary butyl and the like, with preference given to ethyl.

The hydroxyalkyl for $Z^2$ and $Z^3$ is straight chain or branched chain alkyl having 1 to 4 carbon atoms (as defined above), which is substituted by hydroxyl group, and is exemplified by hydroxymethyl, 2-hydroxyethyl, 3-hydroxypropyl, 4-hydroxybutyl and the like, with preference given to 2-hydroxyethyl.

The aminoalkyl optionally having substituents for $Z^2$ and $Z^3$ is straight chain or branched chain alkyl having 1 to 4 carbon atoms (as defined above), which is substituted by amino group, wherein the amino group may be mono- or di-substituted by a substituent such as straight chain or branched chain alkyl having 1 to 4 carbon atoms (as defined above), acyl having 1 to 4 carbon atoms (as defined above), benzoyl and the like. Specific examples thereof include aminomethyl, aminoethyl, dimethylaminomethyl, diethylaminomethyl, formylaminomethyl, 2-formylaminoethyl, acetylaminomethyl, 2-acetylaminoethyl, benzoylaminomethyl and the like.

The group for $Z^2$ and $Z^3$, which may, together with the adjacent nitrogen atom, form a cyclic amine that may have, in the ring, one or two from oxygen atom, sulfur atom and nitrogen atom is cyclic amine selected from pyrrolidine, piperidine optionally having substituents, homopiperidine, piperazine optionally having substituents, homopiperazine optionally having substituents, morpholine and thiomorpholine.

The substituent of the aforementioned piperidine optionally having substituents is exemplified by hydroxy; carboxy; alkoxycarbonyl wherein the alkoxy moiety is straight chain or branched chain alkoxy having 1 to 4 carbon atoms (as defined above); straight chain or branched chain hydroxyalkyl having 1 to 4 carbon atoms (as defined above); alkoxyalkoxy wherein the alkoxy moiety is straight chain or branched chain alkoxy having 1 to 4 carbon atoms (as defined above) (methoxymethoxy, ethoxymethoxy, propoxymethoxy, butoxymethoxy, 2-methoxyethoxy, 3-methoxypropoxy, 4-methoxybutoxy and the like); carboxyalkylcarbonyloxy wherein the alkyl moiety is straight chain or branched chain alkyl having 1 to 4 carbon atoms (as defined above) (carboxymethylcarbonyloxy, 2-carboxyethylcarbonyloxy and the like); acyloxy having 1 to 4 carbon atoms (as defined above); benzoyloxy; phenyl; alkylenedioxy having 1 to 4 carbon atoms (methylenedioxy, ethylenedioxy and the like); oxo; amino optionally mono- or di-substituted by a substituent such as straight chain or branched chain alkyl having 1 to 4 carbon atoms (as defined above), alkoxyalkyl wherein the alkoxy moiety and the alkyl moiety are straight chain or branched chain alkyl having 1 to 4 carbon atoms (as defined above) and alkoxy having 1 to 4 carbon atoms (as defined above), respectively, which is exemplified by methoxymethyl, ethoxymethyl, 2-methoxyethyl, 2-ethoxyethyl and the like, straight chain or branched chain hydroxyalkyl having 1 to 4 carbon atoms (as defined above) and the like; cyclic amine selected from piperidine optionally having substituent (hydroxy, straight chain or branched chain alkoxy having 1 to 4 carbon atoms (as defined above), oxo and the like), morpholine, thiomorpholine, piperazine optionally having substituent (straight chain or branched chain alkyl having 1 to 4 carbon atoms (as defined above), acyl having 1 to 4 carbon atoms (as defined above) and the like) and the like (the cyclic amine may be N-oxide); morpholinomethyl and the like. Specific examples thereof include piperidin-1-yl, 4-hydroxypiperidin-1-yl, 4-carboxypiperidin-1-yl, 4-methoxycarbonylpiperidin-1-yl, 4-ethoxycarbonylpiperidin-1-yl, 4-((2-carboxyethyl)carbonyloxy)piperidin-1-yl, 4-benzoyloxypiperidin-1-yl, 4-piperidinopiperidin-1-yl, 4-morpholinopiperidin-1-yl, 4-thiomorpholinopiperidin-1-yl, 4-(N-oxidemorpholino)piperidin-1-yl, 4,4-ethylenedioxypiperidin-1-yl, 4-oxopiperidin-1-yl, 4-aminopiperidin-1-yl, 4-dimethylaminopiperidin-1-yl, 4-(N-(2-hydroxyethyl)amino)piperidin-1-yl, 4-(N,N-bis(2-hydroxyethyl)amino)piperidin-1-yl, 4-(N-(2-hydroxyethyl)-N-methylamino)piperidin-1-yl, 4-(4-methylpiperazin-1-yl)piperidin-1-yl, 4-(N-(2-hydroxyethyl)amino)piperidin-1-yl, 4-(piperazin-1-yl)piperidin-1-yl, 4-(4-(4-acetylpiperazin-1-yl)piperidine)-1-yl, 4-phenylpiperidin-1-yl, 4-(N-(2-methoxyethyl)amino)piperidin-1-yl, 4-(N-(2-methoxyethyl)-N-methylamino)piperidin-1-yl, 4-(N,N-bis(2-methoxyethyl)amino)piperidin-1-yl, 4-methoxymethoxypiperidin-1-yl, 4-(2-methoxyethyl)oxypiperidin-1-yl, 4-(2-hydroxyethyl)piperidin-1-yl, 4-(4-hydroxypiperidin-1-yl)piperidin-1-yl, 4-(4-morpholinomethyl)piperidin-1-yl, 4-(4-methoxypiperidin-1-yl)piperidin-1-yl, 4-(4-oxopiperidin-1-yl)piperidin-1-yl and the like.

The substituent of the aforementioned piperazine optionally having substituents is exemplified by straight chain or branched chain alkyl having 1 to 4 carbon atoms (as defined above); carboxyalkyl wherein the alkyl moiety is straight chain or branched chain alkyl having 1 to 4 carbon atoms (as defined above) (carboxylmethyl, carboxyethyl and the like); straight chain or branched chain hydroxyalkyl having 1 to 4 carbon atoms (as defined above); alkoxyalkyl wherein the alkyl moiety and the alkoxy moiety are straight chain or branched chain alkyl and alkoxy having 1 to 4 carbon atoms, respectively (as defined above); hydroxyalkoxyalkyl wherein the alkoxy moiety and the alkyl moiety are straight chain or branched chain alkoxy (as defined above) and alkyl (as defined above) having 1 to 4 carbon atoms, respectively, (hydroxymethoxymethyl, hydroxyethoxyethyl and the like); carboxy; alkoxycarbonyl wherein the alkoxy moiety is straight chain or branched chain alkoxy having 1 to 4 carbon atoms (as defined above); alkoxycarbonylalkyl wherein the alkoxy moiety and the alkyl moiety are straight chain or branched chain alkoxy and alkyl having 1 to 4 carbon atoms, respectively (as defined above); acyl having 1 to 4 carbon atoms (as defined above); acyloxyalkyl wherein the acyl moiety and the alkyl moiety are acyl having 1 to 4 carbon atoms and straight chain or branched chain alkyl, respectively (as defined above); straight chain or branched chain aminoalkyl having 1 to 4 carbon atoms and optionally having substituents (as defined above); carboxyalkylcarbonyloxy wherein the alkyl moiety is straight chain or branched chain alkyl having 1 to 4 carbon atoms (as defined above) (carboxymethylcarbonyloxy, (2-carboxyethyl)carbonyloxy and the like); heteroaralkyl (straight chain or branched chain alkyl having 1 to 4 carbon atoms (as defined above), which is substituted by monocyclic or polycyclic heteroaryl (pyridyl, thienyl, furyl and the like) having one or more hetero atoms such as nitrogen atom, oxygen atom, sulfur atom and the like, wherein 5 to 14 atoms constitute a ring); phenyl substituted by a substituent selected from halogen (as defined above), straight chain or branched chain alkyl having 1 to 4 carbon atoms (as defined above) and straight chain or branched chain alkoxy having 1 to 4 carbon atoms (as defined above); 3,4,5,6-tetrahydro-2H-pyran-4-yl; 3,4,5,6-tetrahydro-2H-thiopyran-4-yl; 5-methylisoxazol-4-ylcarbonyl; 2-cyano-3-hydroxycrotonoyl and the like. Specific examples thereof include piperazin-1-yl, 4-methylpiperazin-1-yl, 4-ethylpiperazin-1-yl, 4-hydroxymethylpiperazin-1-yl, 4-(2-hydroxyethyl)piperazin-1-yl, 4-(3-hydroxypropyl)piperazin-1-yl, 4-(tertiary butoxycarbonyl)piperazin-1-yl, 4-(ethoxycarbonylmethyl)piperazin-1-yl, 4-(2-ethoxycarbonylethyl)piperazin-1-yl, 4-(3-ethoxycarbonylpropyl)piperazin-1-yl, 4-(carboxymethyl)piperazin-1-yl, 4-(2-carboxyethyl)piperazin-1-yl, 4-(3-carboxypropyl)piperazin-1-yl, 4-((2-carboxyethyl)carbonyloxy)piperazin-1-yl, 4-(5-methylisoxazol-4-ylcarbonyl)piperazin-1-yl, 4-(2-cyano-3-hydroxycrotonoyl)piperazin-1-yl, 4-(dimethylaminomethyl)piperazin-1-yl, 4-(2-dimethylaminoethyl)piperazin-1-yl, 3,5-dimethyl-4-ethoxycarbonylmethylpiperazin-1-yl, 3,5-dimethyl-4-carboxymethylpiperazin-1-yl, 4-(3-(3-pyridyl)propyl)piperazin-1-yl, 4-(2-(2-hydroxyethoxy)ethyl)piperazin-1-yl, 4-(2-acetyloxyethyl)piperazin-1-yl, 4-(3,4,5,6-tetrahydro-2H-pyran-4-yl)piperazin-1-yl, 4-(3,4,5,6-tetrahydro-2H-thiopyran-4-yl)piperazin-1-yl, 4-(4-chlorophenyl)piperazin-1-yl, 4-(4-fluorophenyl)piperazin-1-yl, 4-(4-methylphenyl)piperazin-1-yl, 4-(4-methoxyphenyl)piperazin-1-yl, 4-methoxymethylpiperazin-1-yl, 4-(2-methoxyethyl)piperazin-1-yl, 4-(3-methoxypropyl)piperazin-1-yl and the like.

The aforementioned homopiperazine optionally having substituents may be substituted by a substituent such as straight chain or branched chain alkyl having 1 to 4 carbon atoms (as defined above) or straight chain or branched chain hydroxyalkyl having 1 to 4 carbon atoms (as defined above). Specific examples thereof include homopiperazine, 4-(hydroxymethyl)homopiperazin-1-yl, 4-(2-hydroxyethyl)homopiperazin-1-yl, 4-methylhomopiperazin-1-yl and the like.

The ring A-B is exemplified by those shown in the following, including any possible combination of ring A and ring B.

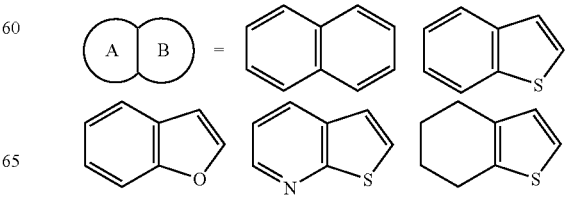

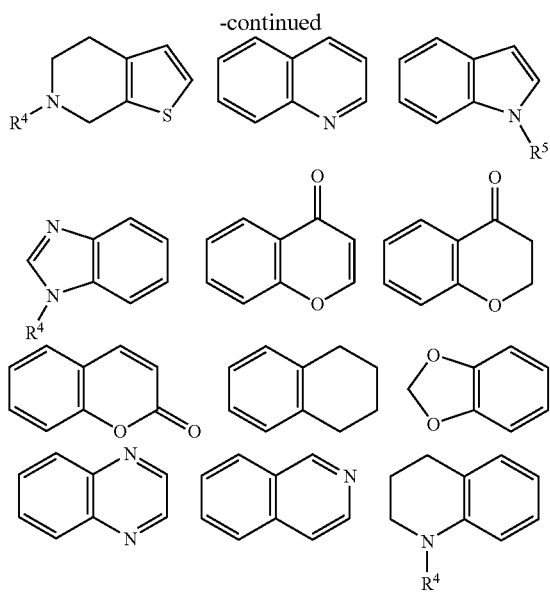

wherein each symbol is as defined above.

A pharmaceutically acceptable salt of the compound of the present invention is exemplified by inorganic acid salts such as hydrochloride, hydrobromate, sulfate, phosphate, nitrate and the like, organic acid salts such as acetate, propionate, succinate, maleate, fumarate, benzoate, citrate, malate, methanesulfonate, benzenesulfonate and the like, when carboxyl group is present, metal salts such as sodium salt, potassium salt, calcium salt, aluminum salt, magnesium salt and the like, salt with amine such as triethylamine and the like and salt with dibasic amino acid such as lysin and the like. The compound of the present invention encompasses hydrates (1 hydrate, ½ hydrate, ¾ hydrate and the like), solvates and the like. Furthermore, the compound of the present invention encompasses N-oxide compound.

Method 1: The compound (I) of the present invention can be produced by the following method:

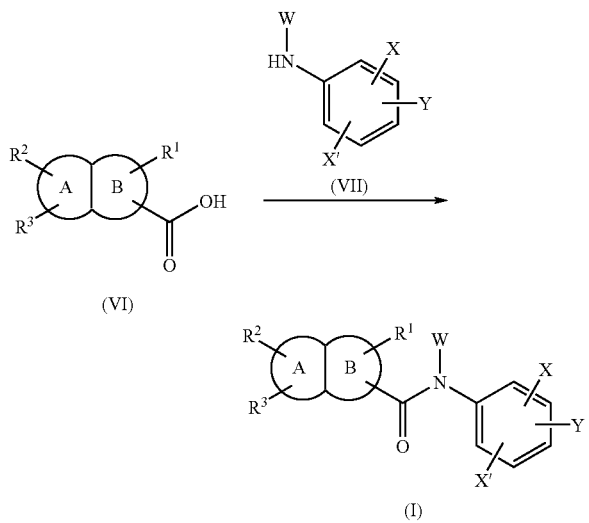

wherein each symbol is as defined above.

The condensation reaction of compound (VI) and compound (VII) can be carried out by the following three methods. (1) The compound (VI) is coverted to an acid halide by a conventional method with a halogenating agent such as thionyl chloride and the like, and condensed with compound (VII) in a suitable solvent (dichloromethane, dichloroethane, chloroform and the like), in the presence of a base (triethylamine, pyridine, sodium methoxide, sodium ethoxide, sodium hydroxide, potassium hydroxide, sodium acetate and the like) at a temperature of from −20° C. to the refluxing temperature of the solvent for 30 min to 12 hr to give compound (I). In this reaction, the base to be used can be used as a solvent. (2) The compound (VI) is condensed with compound (VII) as necessary in a suitable solvent (dimethylformamide, dimethyl sulfoxide, methanol, ethanol, isopropyl alcohol, butanol and the like), in the presence of condensing agent (1,3-dicyclohexylcarbodiimide, 1-ethyl-3-(3-dimethylaminopropyl)carbodiimide, carbonyldiimidazole and the like), or condensed with compound (VII) in a suitable solvent (dimethylformamide, dimethyl sulfoxide and the like), in the presence of phosphoric acid ester such as diethyl cyanophosphate and the like and a base (triethylamine, pyridine and the like) to give compound (I). The reaction temperature is generally from 0° C. to 100° C., and the reaction time is generally from 30 min to 24 hr. The reaction using a condensing agent may be carried out in the presence of 1-hydroxybenztriazole and the like as necessary. (3) The compound (VI) is coverted to lower alcohol (methanol, ethanol and the like) or to a mixed acid anhydride with carbonate (methyl chlorocarbonate, ethyl chlorocarbonate and the like) and the like and condensed with compound (VII) in a suitable solvent (methanol, ethanol, isopropyl alcohol, butanol, ethylene glycol, tetrahydrofuran, toluene, nitrobenzene, a mixed solvent thereof and the like) or without solvent, in the presence of a base (triethylamine, pyridine, sodium methoxide, sodium ethoxide, sodium hydroxide, potassium hydroxide and the like) at a temperature of from room temperature to the refluxing temperature of the solvent for 1 to 24 hr to give compound (I).

In this reaction, when W of compound (VII) is hydrogen, the reaction can be carried out using a protecting group generally used in the field of organic synthesis chemistry, such as tertiary butoxycarbonyl group, 9-fluorenylmethoxycarbonyl group, benzyloxycarbonyl group and the like.

Method 2: A compound (I) wherein w is alkyl or hydroxycarbonylalkyl can be produced by the following method:

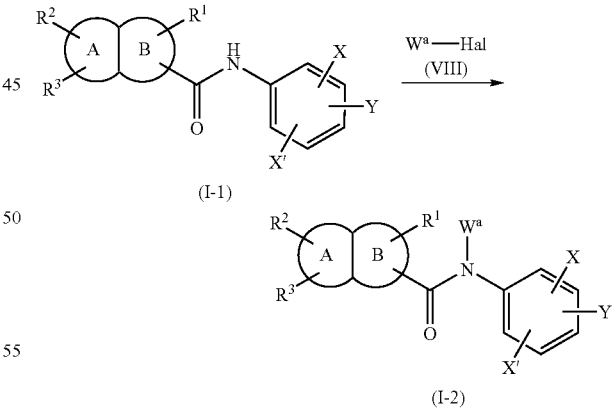

wherein $W^a$ is a group other than hydrogen as a substituent for W, Hal is halogen such as chlorine, bromine, iodine and the like, and other symbols are as defined above.

By reacting compound (1–1) with compound (VIII) in a suitable solvent (dimethylformamide, dimethyl sulfoxide, benzene, toluene, xylene, hexane, tetrahydrofuran, diethyl ether, methanol, ethanol, isopropyl alcohol, tertiary butyl alcohol and the like), in the presence of a base (sodium hydride, sodium hydroxide, potassium hydroxide, potassium carbonate, sodium carbonate, sodium methoxide, sodium ethoxide, triethylamine and the like), at a temperature of from −20° C. to 100° C. for 30 min to 24 hr, compound (1–2) can be produced.

Method 3: The compound (1–1) of the present invention can be also produced by the following method:

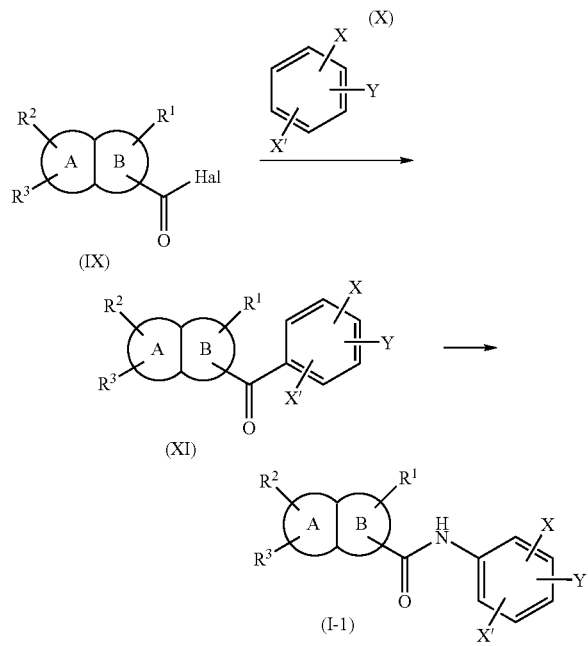

wherein each symbol is as defined above.

By subjecting compound (IX) and compound (X) to Friedel-Crafts reaction in a suitable solvent (tetrahydrofuran, diethyl ether, ethyleneglycol dimethylether, dimethylformamide, dimethyl sulfoxide, methylene chloride, chloroform, dichloroethane, acetonitrile, nitromethane, carbon disulfide etc.) or without solvent as necessary, in the presence of an acid catalyst (aluminum chloride, aluminum bromide, titanium tetrachloride etc.), at a temperature of from −20° C. to 100° C. for 30 min to 24 hr, compound (XI) can be produced. By subjecting compound (XI) to Schmidt reaction in a suitable solvent (benzene, toluene, xylene etc., preferably benzene) with a strong acid (sulfuric acid, trifluoroacetic acid and the like) and sodium azide at a temperature of from −20° C. to the refluxing temperature of the solvent for 1 to 24 hr, compound (1–1) can be produced.

Method 4: The compound (I-1) can be also produced by the following method:

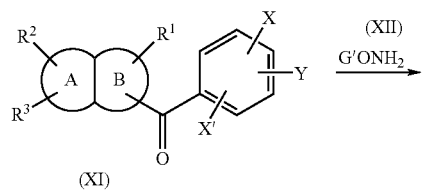

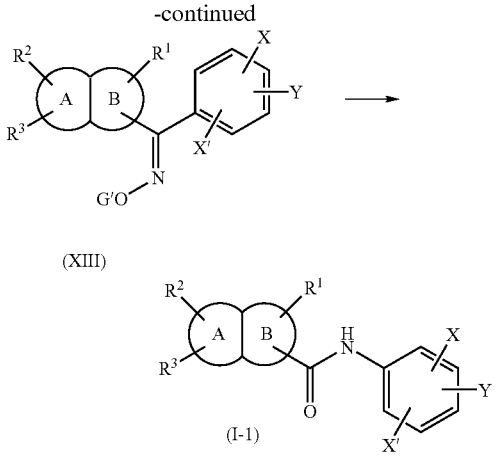

wherein G' is arylsulfonyl group such as hydrogen or benzenesulfonyl and the like, and other symbols are as defined above.

By reacting compound (XI) with compound (XII) in a suitable solvent (water, methanol, ethanol or a mixed solvent thereof etc.), in the presence of a base (sodium carbonate, potassium carbonate, sodium hydroxide, potassium hydroxide, sodium acetate, triethylamine etc.) at a temperature of from −20° C. to 100° C. for 1 to 24 hr, compound (XIII) can be produced. By subjecting compound (XIII) to Beckmann rearrangement reaction in a suitable solvent (water, dimethyl sulfoxide, dimethylformamide, benzene, toluene, xylene or a mixed solvent thereof and the like), at a temperature of from room temperature to the refluxing temperature of the solvent for 1 to 24 hr, compound (1–1) can be obtained.

Method 5: When the compound of the present invention has a hydroxyl group, by subjecting the compound to a condensation reaction generally employed in the field of organic synthetic chemistry with carboxylic acid compound, acid halide compound or acid anhydride compound, the corresponding ester compound can be produced. When the compound of the present invention has a carboxylic acid group, by subjecting the compound to a condensation reaction generally employed in the field of organic synthetic chemistry with alcohol compound or phenol compound, the corresponding ester compound can be produced. Furthermore, when the compound of the present invention has an ester group, by hydrolysis of the compound with an acid (hydrochloric acid, sulfuric acid and the like) or a base (sodium hydroxide, potassium hydroxide and the like) according to a conventional method, the corresponding carboxylic acid compound can be produced. When the compound of the present invention has an amino group, N-alkylation or N-acylation can be conducted using an alkyl halide or acyl halide in the presence of a base (triethylamine, pyridine and the like) according to a conventional method.

Method 6: A compound (VII) wherein W is hydrogen can be produced by the following method:

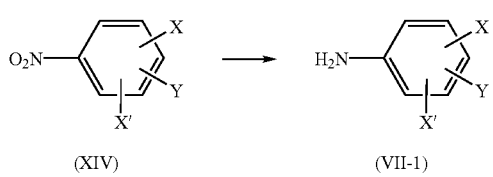

wherein each symbol is as defined above.

The compound (VII-1) can be obtained by reduction generally employed in the field of the organic synthetic chemistry, such as a method comprising treating compound (XIV) with diluted hydrochloric acid or a catalytic amount of ammonium chloride in a suitable solvent (water, methanol, ethanol, propanol, butanol, ethylene glycol or a mixed solvent thereof and the like), using iron powder as a catalyst, or a method of catalytic reduction comprising hydrogenation in the presence of a catalyst such as nickel, palladium, platinum and the like, a method comprising the use of iron chloride and hydrazine, a method comprising Birch reduction in liquid ammonia using alkaline metal such as sodium, lithium and the like, and the like. The reaction temperature is generally from room temperature to the refluxing temperature of the solvent and the reaction time is generally from 1 to 24 hr.

Method 7: The compound (VII-1) can be also produced by the following method:

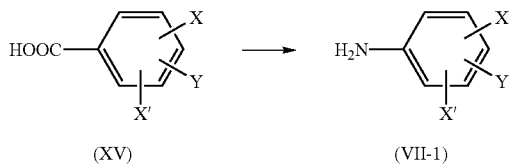

wherein each symbol is as defined above.

The compound (VII-1) can be obtained by treating compound (XV) with sodium azide and a strong acid (sulfuric acid, trifluoroacetic acid and the like) utilizing Schmidt reaction in a suitable solvent (water, methanol, ethanol, propanol, butanol, tertiary butyl alcohol, ethylene glycol, benzene, toluene, xylene, preferably benzene), at a temperature of from room temperature to the refluxing temperature of the solvent for 1 to 24 hr, or reacting with triethylamine and diphenylphosphonylazidine in a suitable solvent (methanol, ethanol, isopropyl alcohol, butanol, tertiary butanol, preferably tertiary butanol) at a temperature of from room temperature to the refluxing temperature of the solvent for 1 to 24 hr and treating with an acid (hydrochloric acid, sulfuric acid and the like).

Method 8: A compound (XIV) wherein X is halogen substituted at the 3-position and Y is alkoxy substituted at the 4-position can be produced by the following method:

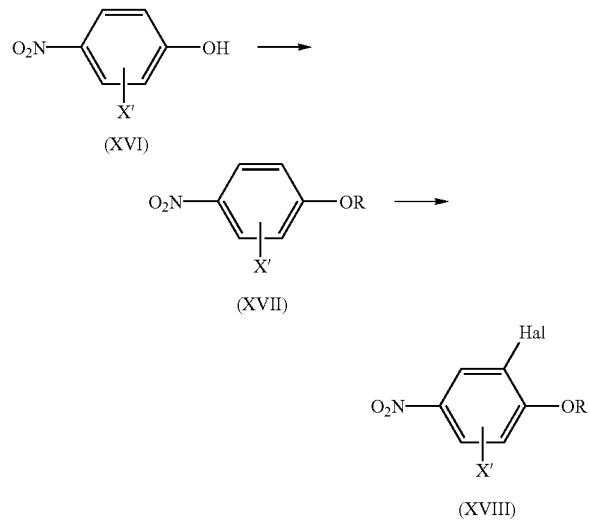

wherein R is alkyl having 1 to 6 carbon atoms and other symbols are as defined above.

The compound (XVII) can be obtained by reacting compound (XVI) with alkyl halide in a suitable solvent (water, dimethyl sulfoxide, dimethylformamide, toluene, methanol, ethanol, tetrahydrofuran or a mixed solvent thereof and the like) in the presence of a base (sodium hydroxide, sodium hydride, sodium methoxide, sodium ethoxide, butyl lithium, butyl magnesium chloride etc.) at a temperature of from −20° C. to the refluxing temperature of the solvent for 1 to 24 hr. The compound (XVIII) can be obtained by reacting compound (XVII) with halogen (chlorine, bromine etc.) at a temperature of from −20° C. to room temperature for 1 to 24 hr. The compound (XVIII) can be also obtained by halogenating compound (XVI) under the above-mentioned reaction conditions, followed by alkylation.

Method 9: A compound (XIV) wherein Y is alkoxy, hydroxyalkoxy, hydroxycarbonylalkoxy, aminoalkoxy optionally having substituents, alkylthio, hydroxyalkylthio, hydroxycarbonylalkylthio, aminoalkylthio optionally having substituents or a group $N(Z^2)(Z^3)$ can be produced by the following method:

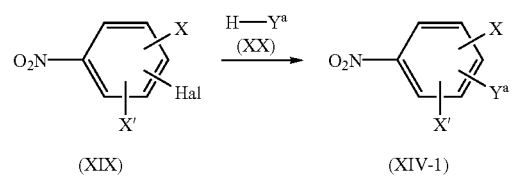

wherein $Y^a$ is alkoxy, hydroxyalkoxy, hydroxycarbonylalkoxy, aminoalkoxy optionally having substituents, alkylthio, hydroxyalkylthio, hydroxycarbonylalkylthio, aminoalkylthio optionally having substituents or a group $N(Z^2)(Z^3)$ and other symbols are as defined above.

The compound (XIV-1) can be produced by reacting compound (XIX) with compound (XX) in a suitable solvent (chloroform, acetonitrile, water, methanol, ethanol, tetrahydrofuran, diethyl ether, dimethylformamide, dimethyl sulfoxide or a mixed solvent thereof and the like) or without solvent, in the presence of a base (sodium hydroxide, sodium methoxide, sodium ethoxide, sodium hydride, butyl lithium and the like) at a temperature of from −20° C. to 100° C. for 1 to 24 hr.

Method 10: A compound (XIV) or (XV) wherein X is cyano can be produced by the following method:

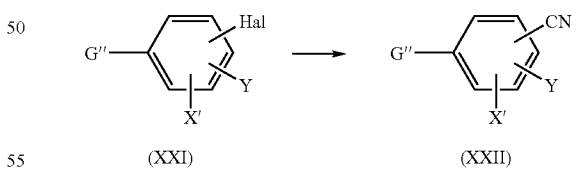

wherein G″ is nitro or carboxy and other symbols are as defined above.

The compound (XXII) can be obtained by reacting compound (XXI) with a cyanizing agent (sodium cyanide, potassium cyanide, copper (I) cyanide and the like) in a suitable solvent (water, methanol, ethanol, propanol, ethylene glycol, dimethyl sulfoxide, dimethylformamide or a mixed solvent thereof and the like) at a temperature of from room temperature to 100° C. for 1 to 24 hr.

Method 11: The compound (VII-2) can be produced by the following method:

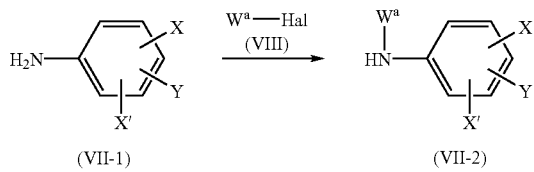

wherein each symbol is as defined above.

The compound (VII-2) can be obtained by reacting compound (VII-1) with compound (VIII) in the presence of sodium acetate without solvent or in a suitable solvent (tetrahydrofuran, diethyl ether, dimethylformamide, dimethyl sulfoxide and the like) at a temperature of from room temperature to 60° C. for 1 to 24 hr.

The compound (VII-2) can be also obtained by protecting compound (VII-1) by a conventional method with tertiary butoxycarbonyl group and the like which is generally used as an amino-protecting group, and reacting with compound (VIII) in the presence of sodium metal, sodium hydride, sodium amide and the like, followed by deprotection by a conventional method.

Method 12: A compound (XIV) wherein Y is substituted at the 4-position of phenyl group and Y is compound (Va) can be produced by the following method:

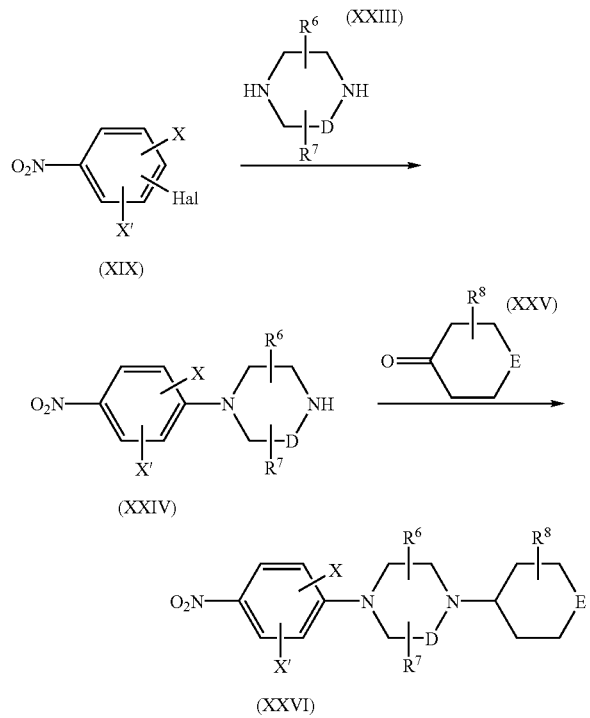

wherein each symbol is as defined above.

The compound (XXIV) can be obtained by reacting compound (XIX) (Hal is substituted at the 4-position of phenyl group) with compound (XXIII) in a suitable solvent (chloroform, acetonitrile, water, methanol, ethanol, tetrahydrofuran, diethyl ether, dimethylformamide, dimethyl sulfoxide or a mixed solvent thereof and the like) or without solvent, in the presence of a base (sodium hydroxide, sodium methoxide, sodium ethoxide, sodium hydride, butyl lithium and the like) as necessary, at a temperature of from −20° C. to 100° C. for 1 to 24 hr. The compound (XXVI) can be obtained by reacting compound (XXIV) with compound (XXV) in a suitable solvent (chloroform, acetonitrile, toluene, benzene, tetrahydrofuran, diethyl ether, dimethylformamide, dimethyl sulfoxide or a mixed solvent thereof and the like) according to the method described in Tetrahedron, vol. 38, 3, p. 413 (1982), or by reacting sodium cyanoborate.

Method 13: A compound (XIV) wherein Y is substituted at the 4-position of phenyl group and Y is compound (Va) can be produced by the following method.

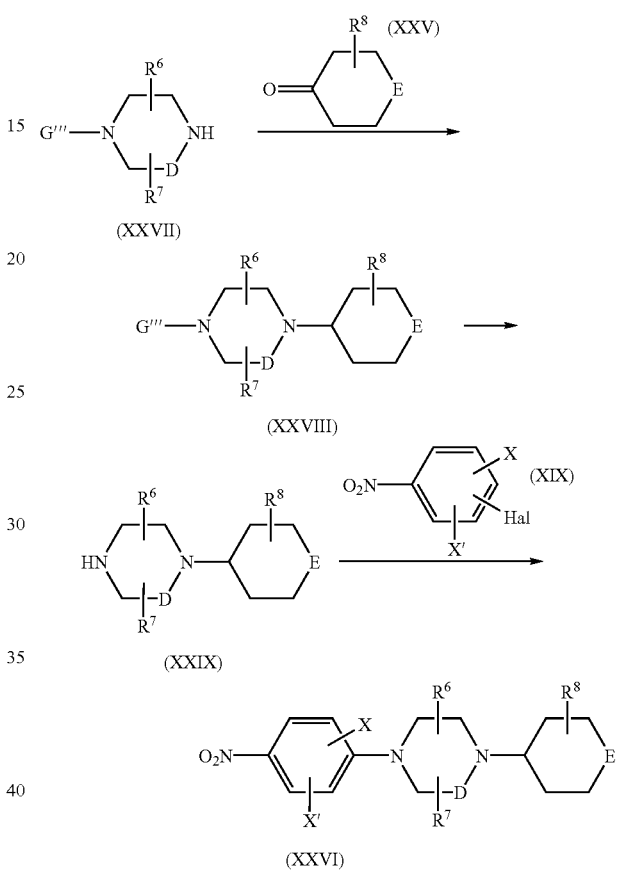

wherein G''' is a substituent widely used as a protecting group such as benzyl group, ethoxycarbonyl group and the like, and other symbols are as defined above.

The compound (XXVIII) can be obtained by reacting compound (XXVII) with compound (XXV) in a suitable solvent (chloroform, acetonitrile, toluene, benzene, tetrahydrofuran, diethyl ether, dimethylformamide, dimethyl sulfoxide or a mixed solvent thereof and the like) according to the method described in Tetrahedron, vol. 38, 3, p. 413 (1982), or by allowing reaction with sodium cyanoborate. By suitable deprotection of G''' of compound (XXVIII), compound (XXIX) can be obtained. The compound (XXVI) can be obtained by reacting compound (XXIX) with compound (XIX) (Hal is substituted at the 4-position of phenyl group) in a suitable solvent (chloroform, acetonitrile, water, methanol, ethanol, tetrahydrofuran, diethyl ether, dimethylformamide, dimethyl sulfoxide or a mixed solvent thereof and the like) or without solvent, in the presence of a base (sodium hydroxide, sodium methoxide, sodium ethoxide, sodium hydride, butyl lithium and the like) as necessary at a temperature of from −20° C. to 100° C. for 1 to 24 hr.

The compound of the present invention can be converted to an acid addition salt as necessary by treating the compound with an acid (inorganic acid such as hydrochloric acid, hydrobromic acid, sulfuric acid, phosphoric acid, nitric acid and the like or organic acid such as acetic acid, propionic acid, succinic acid, maleic acid, fumaric acid, benzoic acid, citric acid, malic acid, methanesulfonic acid, benzenesulfonic acid and the like), in a suitable solvent (water, methanol, ethanol, propanol, isopropyl alcohol, diethyl ether, tetrahydrofuran, dioxane etc.). When the obtained compound has a carboxyl group, it can be converted to the corresponding metal salt by treating the compound with sodium hydroxide, potassium hydroxide, calcium hydroxide, aluminum hydroxide, magnesium hydroxide, sodium alcoholate and the like, and to the corresponding salt as necessary by treating the compound with amine such as triethylamine and the like or dibasic amino acid such as lysin and the like in a suitable solvent. When the crystal of the compound of the present invention is anhydride, it can be converted to hydrates (1 hydrate, ½ hydrate, ¾ hydrate and the like) or solvate by treating the compound with water, hydrous solvent or other solvent. In addition, the compound of the present invention can be converted to an N-oxide compound by treating the compound with an oxidant such as hydrogen peroxide, metachloroperbenzoic acid and the like according to a conventional method.

The compound of the present invention thus obtained can be isolated and purified by a method known in the field of organic synthetic chemistry, such as recrystallization, column chromatography and the like. When the obtained product is a racemate, it can be resolved into a desired optically active form by, for example, fractional crystallization using a salt with optically active acid or base, or by passing a column packed with an optically active carrier. It can be also produced by using an optically active starting material compound and the like.

Since the compound of the present invention and a pharmaceutically acceptable salt thereof have a superior inhibitory effect on the proliferation of activated lymphocyte, particularly inhibitory effect on lymphocyte proliferation dependent on IL-2, IL-4, IL-7, IL-9, IL-13 or IL-15, and also inhibit production of IL-15 as well as inflammatory cytokines (IL-1, IL-6, IL-12, IL-15, IL-18, TNF-α and the like) derived by IL-15, and have been further clarified to inhibit phosphorylation of tyrosine kinase represented by JAK1, JAK3 and the like present in the signal transduction pathway involved in the lymphocyte proliferation induced by IL-15, they can be used for the prophylaxis or treatment of various-autoimmune diseases. More particularly, the compound of the present invention and a pharmaceutically acceptable salt thereof can be used for the prophylaxis or treatment of the diseases caused by the proliferation of lymphocyte, particularly autoimmune diseases, such as rheumatoid arthritis, systemic lupus erythematosus, nephrotic syndrome lupus, Hashimoto's thyroiditis, multiple sclerosis, myasthenia gravis, type I diabetes, type II adult-onset type diabetes, uveitis, nephrotic syndrome, steroid-dependent and steroid-resistant nephrosis, palmoplantar pustulosis, allergic encephalomyelitis, glomerulonephritis and the like. They can be also used for the treatment of inflammatory, proliferative and hyper-proliferative skin diseases, and the onset of immunity-mediated skin diseases, such as psoriasis, psoriatic arthritis, atopic eczema (atopic dermatitis), contact dermatitis, and further, eczematous dermatitis, seborrheic dermatitis, lichen planus, pemphigus, bullous pemphigoid, epidermolysis bullosa, urticaria, vascular edema, angiitis, erythema, skin eosinophilia, acne, alopecia areata, eosinophilic fasciitis and atherosclerosis. The compound of the present invention more particularly can be used for the recovery of hair in female pattern or male pattern alopecia or senile alopecia by the treatment of preventing hair loss, forming hair germ, and/or producing and growing hair.

The compound of the present invention is also applicable to the treatment of symptoms of respiratory diseases, such as sarcoidosis, pulmonary fibrosis, idiopathic interstitial pneumonia and reversible obstructive airway diseases, exemplified by asthma such as bronchial asthma, infantile asthma, allergic asthma, intrinsic asthma, extrinsic asthma and dust asthma, particularly chronic or intractable asthma (e.g., late asthma and bronchial hypersensitivity), bronchitis and the like. The compound of the present invention can be also used for the treatment of ischemia-related liver disturbance. Moreover, it is also effective for certain ocular diseases, such as conjunctivitis, keratoconjunctivitis, keratitis, vernal conjunctivitis, Behcet's disease-related uveitis, herpetic keratitis, keratoconus, corneal epithelial degeneration, corneal leukoma, ocular pemphigus, Mooren's ulcer, scleritis, Graves' ophthalmopathy, severe intraocular inflammation and the like.

The compound of the present invention can be also used for the prophylaxis or treatment of mucosal or vascular inflammations [e.g., leukotriene B4-mediated disease, gastric ulcer, vascular damage caused by ischemic disease and thrombus, ischemic bowel disease, inflammatory bowel diseases (e.g., Crohn's disease and ulcerative colitis), necrotizing colitis], thermal burn-related intestinal injury. The composition of the present invention can be used for the treatment or prophylaxis of renal diseases such as interstitial nephritis, Goodpasture's syndrome, hemolytic uremic syndrome and diabetic nephropathy; nervous diseases selected from polymyositis, Guillain-Barre syndrome, Meniere's disease and radiculopathy; endocrine diseases such as hyperthyroidism and Basedow's disease; hemopathy such as pure red-cell aplasia, aplastic anemia, hyoplastic anemia, essential thrombocytopenic purpura, autoimmune hemolytic anemia, defective production of granulocytopenia and erythrocyte; bone diseases such as osteoporosis; respiratory diseases such as sarcoidosis, pulmonary fibrosis and idiopathic interstitial pneumonia; skin diseases such as dermatomyositis, vitiligo vulgaris, ichthyosis vulgaris, photoallergic sensitivity and cutaneous T-cell lymphoma; circulatory diseases such as arteriosclerosis, aortitis, polyarteritis nodosa and cardiac myopathy; collagen diseases such as scleroderma, Wegener's granulomatosis and Sjogren's syndrome; adiposis; eosinophilic fasciitis; gum disease; nephrotic syndrome; hemolytic uremic syndrome; and muscular dystrophy.

Since the compound of the present invention is suitable for the prophylaxis or treatment of intestinal inflammation/allergy, such as coeliac disease, proctitis, eosinophilic gastroenteritis, mastocytosis, Crohn's disease and ulcerative colitis and allergosis, which are related to foodstuff but show symptoms not directly related to the gastrointestinal tract, such as migraine, rhinitis and eczema. Moreover, because the compound of the present invention promotes liver regeneration activity and/or thickening and overgrowth of hepatocytes, it can be used for the treatment or prophylaxis of immunogenic diseases (e.g., chronic autoimmune liver diseases including autoimmune hepatitis, primary biliary cirrhosis and sclerosing cholangitis), partial liver resection, acute liver necrosis (e.g., necrosis due to toxin, viral hepatitis, shock or oxygen depletion), and liver diseases such as viral hepatitis type B, hepatitis non-A/non-B and liver cirrhosis.

The compound of the present invention can be also used for the prophylaxis or treatment of malignant rheumatoid arthritis, amyloidosis, fulminant hepatitis, Shy-Drager syndrome, pustular psoriasis, Behcet's disease, systemic lupus erythematosus, endocrine ophthalmopathy, progressive systemic sclerosis, mixed connective tissue disease, aortitis syndrome, wegener's granuloma, active chronic hepatitis, Evans' syndrome, hay fever, idiopathic hypoparathyroidism, Addison's disease (autoimmune adrenalitis), autoimmune orchitis, autoimmune ovaritis, cold hemagglutinin disease, paroxysmal cold hemoglobinuria, pernicious anemia, adult T cell leukemia, autoimmune atrophic gastritis, lupoid hepatitis, tubulointerstitial nephritis, membranous nephropathy, amyotrophic lateral sclerosis, rheumatic fever, post-myocardial infarction syndrome and sympathetic ophthalmia.

In some cases, the compound of the present invention or a pharmaceutically acceptable salt thereof can be used along with other antirheumatic drugs (gold preparation, penicillamine, bucillamine, lobenzarit, actarit, salazosulfapyridine and the like), immunosuppressant, steroids (prednisolone, methylprednisolone, dexamethasone, hydrocortisone and the like), nonsteroidal antiinflammatory drug and the like. Particularly preferred as the immunosuppressant are selected from azathioprine, cyclophosphamide, methotrexate, brequinar sodium, deoxyspergualin, mizoribine, 2-morpholinoethyl ester of mycophenolic acid, cyclosporine, rapamycin, tacrolimus hydrate, leflunomide, OKT-3, anti-TNF-α antibody, anti-IL-6 antibody and FTY720 (EP627406-B1). Examples of the nonsteroidal antiinflammatory drug include aspirin, indomethacin, indomethacinfarnesyl, diclofenac sodium, alclofenac, amfenac sodium, ibuprofen, ketoprofen, loxoprofen sodium, naproxen, pranoprofen, zaltoprofen, mefenamic acid, flufenamic acid, tolfenamic acid, phenylbutazone, ketophenylbutazone, piroxicam, tenoxicam, ampiroxicam and the like.

As mentioned above, the compound of the present invention and a pharmaceutically acceptable salt thereof have a novel action mechanism, which is different from that of existing antirheumatic drugs, immunosuppressants, steroids, nonsteroidal antiinflammatory drugs and the like used for the treatment of various autoimmune diseases, and therefore, are expected to show synergistic action by concurrent use with the aforementioned existing pharmaceutical agents.

When the compound of the present invention or a pharmaceutically acceptable salt thereof is used as a pharmaceutical agent, the compound of the present invention can be administered orally or parenterally in the form of a pharmaceutical composition or preparation (tablet, pill, capsule, granule, powder, syrup, emulsion, elixir, suspension, solution, injection, drip injection, eye drop, eye ointment, suppository, ointment or lotion and the like) obtained by admixing with a pharmaceutically acceptable carrier (excipient, binder, disintegrant, flavoring agent, odor improving agent, emulsifier, diluent, dissolution aids and the like).

The pharmaceutical composition can be formulated into a pharmaceutical preparation according to a conventional method. In the present specification, by the parenteral is meant subcutaneous injection, intravenous injection, intramuscular injection, intraperitoneal injection, drip injection or eye drop instillation and the like. A preparation for injection, such as sterile aqueous suspension or oily suspension for injection can be prepared according to a method known in the pertinent field using suitable dispersing agent, moistening agent and suspending agent. The preparation for sterile injection may be a non-toxic sterile injectable solution or suspension in diluent or solvent, which is capable of parenteral administration, such as aqueous solution and the like. Acceptable vehicle or solvent that can be used is exemplified by water, Ringer's solution, isotonic saline solution and the like. In addition, sterile nonvolatile oil can be generally used as a solvent or suspending solvent. For this end, any nonvolatile oil or fatty acid can be used, including naturally occurring, synthetic or semi-synthetic fatty oil or fatty acid, naturally occurring, synthetic or semi-synthetic mono-, di- or triglycerides. When an injection is prepared, a suitable suspending agent, nonionic surfactant, dissolution aids and the like may be used concurrently as necessary. The suppository for rectal administration can be produced by admixing the drug and a suitable non-irritant vehicle, which is a substance which is solid at ambient temperature but liquid at the temperature of intestine and which dissolves in the rectum to release the drug, such as cocoa butter and polyethylene glycols. The dosage form of solid composition for oral administration is exemplified by those mentioned above such as powder, granule, tablet, pill, capsule and the like. In the above-mentioned dosage form, one or more active compounds can be admixed with at least one additive such as sucrose, lactose, cellulose sugar, mannitol, multitol, dextran, starches, agar, arginates, chitins, chitosans, pectins, gum tragacanths, acacia, gelatins, collagens, casein, albumin, synthesis, semi-synthetic polymers and glycerides. Such dosage form can contain a further usual additive, which is exemplified by inert diluent, lubricant such as magnesium stearate and the like, preservative such as parabens, sorbins and the like, antioxidant such as arcorbic acid, α-tocopherol, cysteine and the like, disintegrant, binder, thickener, buffer, sweetener, flavor, perfume and the like. Tablet and pill may be produced with an application of an enteric coating. The liquid for oral administration is exemplified by emulsion, syrup, elixir, suspension, solution and the like, which are acceptable for pharmaceutical agents and which may contain inert diluent, such as water and the like, generally used in this field. When an eye drop is to be formed, an aqueous liquid or aqueous solution is used, which is particularly an aqueous solution for sterile injection. The liquid for eye drop instillation may contain various additives as appropriate, such as buffer, isotonicity agent, dissolution aids, preservative, thickener, chelating agent, pH adjuster and aromatic agent. When an ointment is to be formed, oleaginous base, emulsion base, water-soluble base, suspension base and the like are used and a dissolution or absorption promoter may be added as appropriate. When a lotion is to be formed, the compound is dispersed or partially dissolved in a liquid medium and an emulsifier, a dissolution or absorption promoter, a thickener and a stabilizer can be added as appropriate.

The compound of the formula (I) and a pharmaceutically acceptable salt thereof of the present invention are expected to show a superior treatment effect by combined use with one or more pharmaceutical agents selected from antirheumatic drug, immunosuppressant, steroidal drug and nonsteroidal antiinflammatory drug. As used herein, by the "combined use" is meant a combination composition of the compound of the present invention or a pharmaceutically acceptable salt thereof with one or more pharmaceutical agents selected from antirheumatic drug, immunosuppressant, steroidal drug and nonsteroidal antiinflammatory drug, and the use as a potentiator of one or more pharmaceutical agents selected from antirheumatic drug, immunosuppressant, steroidal drug and nonsteroidal antiinflammatory drug, containing the compound of the present invention or a pharmaceutically acceptable salt thereof, including combined use and concurrent use, wherein two or more active ingredient compounds are simultaneously used with or without mixing or used in a staggered manner. The pharmaceutical agent of the present invention which is characterized by the combined use of the compound represented by the above-mentioned formula (I) or a pharmaceutically acceptable salt thereof and one or more pharmaceutical agents selected from antirheumatic drug, immunosuppressant, steroidal drug and nonsteroidal antiinflammatory drug is not particularly limited in terms of the mode of use thereof as long as the compound represented by the above-mentioned formula (I) or a pharmaceutically acceptable salt thereof and one or more pharmaceutical agents selected from antirheumatic drug, immunosuppressant, steroidal drug and nonsteroidal antiinflammatory drug are combined. For example, (A) the compound represented by the formula (I) or a pharmaceutically acceptable salt thereof, and (B) one or more pharmaceutical agents selected from antirheumatic drug, immunosuppressant, steroidal drug and nonsteroidal antiinflammatory drug may be respectively contained as preparations generally administered or may be a composition wherein they are combined in advance. The combined pharmaceutical agent of the present invention may be a single agent obtained by, for example, mixing the compound represented by the formula (I) or a pharmaceutically acceptable salt thereof and one or more pharmaceutical agents selected from antirheumatic drug, immunosuppressant, steroidal drug and nonsteroidal antiinflammatory drug according to a known production method of pharmaceutical preparations using, where desired pharmaceutically acceptable diluent, excipient and the like, or each processed into each preparation using, where desired pharmaceutically acceptable diluent, excipient and the like, or a combination preparation in a container (set, kit, pack) including respective preparations separately prepared. For example, the combined pharmaceutical agent of the present invention can be used as (1) a combination preparation packaging the same or different preparations of a preparation containing the compound represented by the formula (I) or a pharmaceutically acceptable salt thereof, and one or more pharmaceutical agents selected from antirheumatic drug, immunosuppressant, steroidal drug and nonsteroidal antiinflammatory drug, or (2) as a composition containing the compound represented by the formula (I) or a pharmaceutically acceptable salt thereof and one or more pharmaceutical agents selected from antirheumatic drug, immunosuppressant, steroidal drug and nonsteroidal antiinflammatory drug.

The administration route of the pharmaceutical combination agent of the present invention may be oral administration or parenteral administration as in the case of the administration route of the pharmaceutical agent of the above-mentioned compound of the present invention, which is concretely determined in consideration of the location and the like of the target disease. When the compound of the present invention or a pharmaceutically acceptable salt thereof and one or more pharmaceutical agents selected from antirheumatic drug, immunosuppressant, steroidal drug and nonsteroidal antiinflammatory drug are separately prepared, these may be administered to a single subject separately, simultaneously, or at a timelag, by the same route or different routes. For administration of the pharmaceutical combination agent of the present invention, the compound of the present invention or a pharmaceutically acceptable salt thereof, and one or more pharmaceutical agents selected from antirheumatic drug, immunosuppressant, steroidal drug and nonsteroidal antiinflammatory drug can be administered in a dosage form prepared by a conventional method similar to the above-mentioned method.

When the compound of the present invention or a pharmaceutically acceptable salt thereof is used as a combination composition, the ratio of composition is optional, and the amount of the compound of the present invention or a pharmaceutically acceptable salt thereof to be mixed can be determined depending on the kind of the various pharmaceutical agents to be mixed in combination, and the factors such as titer and the like. When it is used as a combination drug, the dose of the compound of the present invention or a pharmaceutically acceptable salt thereof, and the pharmaceutical agent to be combined can be determined as appropriate within the range generally employed. It is preferable to administer in a smaller dose than the dose for single use of each pharmaceutical agent, with the hope of affording a synergistic effect.

When the compound of the present invention or a pharmaceutically acceptable salt thereof is used as a pharmaceutical agent or a combination drug, the dose is determined depending on the age, body weight, general health conditions, sex, diet, administration time, administration method, clearance rate, combination of drugs, the condition of the disease then under treatment and other factors.

The compound of the present invention and a pharmaceutically acceptable salt thereof are low-toxic and can be used safely. The daily dose varies depending on the conditions and body weight of patients, the kind of compound, administration route and the like. It is preferably from about 0.01 mg to 100 mg/patient/day, preferably 0.01 mg to 50 mg/patient/day, by parenteral administration (subcutaneous, intravenous, intramuscular or rectal) or from about 0.01 mg to 1000 mg/patient/day, preferably 0.01 mg to 500 mg/patient/day, by oral administration.

The compounds of the formulas (Va) and (Vb) are novel substances and useful as a synthetic intermediate for the compound of the formula (I). As the compound of the formula (Va), the compound obtained in Starting Material Synthetic Example 11 is preferable, and as the compound of the formula (Vb), the compounds obtained in Starting Material Synthetic Examples 2–9 and Starting Material Synthetic Examples 12–16 are preferable.

BEST MODE FOR EMBODYING THE INVENTION

The present invention is explained in detail by referring to Starting Material Synthetic Examples, Examples, Formulation Examples and Experimental Examples, which are not to be construed as limitative.

STARTING MATERIAL SYNTHETIC EXAMPLE 1

4,5,6,7-tetrahydrobenzo[b]thiophene-3-carboxylic acid

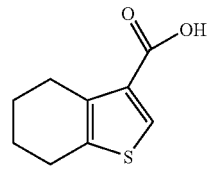

Cyclohexanone (98 μg), ethyl cyanoacetate (113 g), sulfur (32 g) and piperidine (85 g) were added to ethanol (250 ml), and the mixture was stirred at 78° C. for 3 hr. The reaction mixture was cooled, and the precipitated crystals were collected by filtration. The crystals were added to tetrahydrofuran (300 ml) and the mixture was stirred together with isoamyl nitrite (351 g) and triethylamine (202 g) at room temperature for 24 hr to give ethyl 4,5,6,7-tetrahydrobenzo[b]thiophene-3-carboxylate (101 g). This was subjected to hydrolysis under basic conditions to give the title compound (85 g). melting point: 170–172° C.

STARTING MATERIAL SYNTHETIC EXAMPLE 2

5-amino-2-neopentyloxybenzonitrile

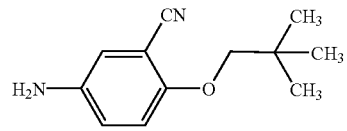

To a dimethylformamide solution (364 ml) containing 2-chloro-5-nitrobenzonitrile (91 g) and neopentyl alcohol (52 g) was added sodium hydride (60% contained, 27.8 g) under ice-cooling, and the mixture was stirred for 1 hr. Water was added to the reaction mixture and the mixture was extracted with toluene. The organic layer was washed with saturated brine and dried over anhydrous magnesium sulfate. The solvent was evaporated under reduced pressure. Diisopropyl ether was added to the residue to allow crystallization and the crystals were recrystallized from a mixed solvent of ethyl acetate-n-hexane to give 2-neopentyloxy-5-nitrobenzonitrile (105 g). Subsequently, ammonium chloride (10 g) and iron powder (75 g) were added to a mixed solvent of water (286 ml) and ethanol (753 ml) and the mixture was heated to 65° C. 2-Neopentyloxy-5-nitrobenzonitrile (80.5 g) was added by portions over 20 min and the mixture was stirred at the refluxing temperature for 30 min. The reaction mixture was ice-cooled and filtrated. The solvent was evaporated under reduced pressure. An aqueous sodium hydroxide solution was added and the mixture was extracted with toluene. The organic layer was washed with saturated brine and dried over anhydrous sodium sulfate. The solvent was evaporated under reduced pressure. Diisopropyl ether was added to the residue to allow crystallization and the crystals were recrystallized from a mixed solvent of ethyl acetate-n-hexane to give the title compound (70 g). melting point: 55–56° C.

$^1$H-NMR (270 MHz, CDCl$_3$)δ(ppm):1.06 (9H, s), 3.4–3.5 (2H, brs), 3.61 (2H, s), 6.74–6.82 (3H, m)

STARTING MATERIAL SYNTHETIC EXAMPLE 3

5-amino-2-phenoxybenzonitrile

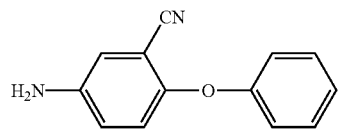

By the reaction and treatment in the same manner as in Starting Material Synthetic Example 2 using 2-chloro-5-nitrobenzonitrile (10 g) and phenol (5.7 g), the title compound (3 g) was obtained. melting point: 89° C.

$^1$H-NMR (270 MHz, CDCl$_3$)δ(ppm):3.6–3.9 (2H, brs), 6.81 (1H, d, J=1.3 Hz), 6.89 (1H, d, J=1.3 Hz), 6.93 (1H, m), 6.98–7.13 (2H, m), 7.25–7.35 (2H, m), 7.46–7.49 (1H, m)

STARTING MATERIAL SYNTHETIC EXAMPLE 4

5-amino-2-piperidinobenzonitrile

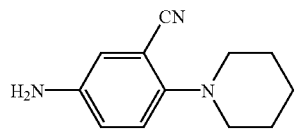

2-Chloro-5-nitrobenzonitrile (20 g) and piperidine (9.34 g) were added to acetonitrile (100 ml) and the mixture was stirred at the refluxing temperature for 1 hr. The solvent was evaporated under reduced pressure. Diisopropyl ether was added to the residue to allow crystallization and the crystals were recrystallized from methanol to give 5-nitro-2-piperidinobenzonitrile (17 g). Subsequently, ammonium chloride (1.6 g) and iron powder (8.4 g) were added to a mixed solvent of water (40 ml) and ethanol (120 ml) and the mixture was heated to 65° C. 5-Nitro-2-piperidinobenzonitrile (10 g) was added by portions over 20 min and the mixture was stirred at the refluxing temperature for 30 min. The reaction mixture was ice-cooled and the reaction solution was filtrated. The solvent was evaporated under reduced pressure. An aqueous sodium hydroxide solution was added and the mixture was extracted with toluene. The organic layer was washed with saturated brine and dried over anhydrous sodium sulfate. The solvent was evaporated under reduced pressure. Diisopropyl ether was added to the residue to allow crystallization and the crystals were recrystallized from a mixed solvent of ethyl acetate-n-hexane to give the title compound (8.3 g). melting point: 148–149° C.

$^1$H-NMR (270 MHz, CDCl$_3$)δ(ppm):1.50–1.59 (2H, m), 1.71–1.79 (4H, m), 2.96–3.04 (4H, m), 3.6 (2H, brs), 6.76–6.90 (3H, m).

STARTING MATERIAL SYNTHETIC EXAMPLE 5

5-amino-2-(4-hydroxypiperidin-1-yl)benzonitrile

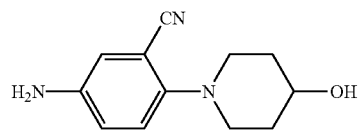

By the reaction and treatment in the same manner as in Starting Material Synthetic Example 4 using 2-chloro-5-nitrobenzonitrile (36 g) and 4-hydroxypiperidine (50 g), the title compound (25 g) was obtained. melting point: 144–145° C.

$^1$H-NMR (270 MHz, CDCl$_3$)δ(ppm):1.70–1.79 (2H, m), 1.81–2.04 (2H, m), 2.78–2.86 (2H, m), 3.3–3.4 (2H, m), 3.7–3.8 (1H, m), 3.7–3.8 (2H, brs), 6.85–6.94 (3H, m)

STARTING MATERIAL SYNTHETIC EXAMPLE 6

5-amino-2-[4-(2-hydroxyethyl)piperazin-1-yl]benzonitrile

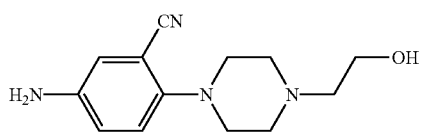

By the reaction and treatment in the same manner as in Starting Material Synthetic Example 4 using 2-chloro-5-nitrobenzonitrile (15 g) and piperazinoethanol (16 g), the title compound (15 g) was obtained. melting point: 137–138° C.

$^1$H-NMR (270 MHz, DMSO-$d_6$)δ(ppm):2.44 (2H, dd, J=5.3, 6.6 Hz), 2.55 (4H, dd, J=4.0, 5.3 Hz), 2.90 (4H, dd, J=4.0, 5.3 Hz), 3.51 (2H, dt, J=5.3, 6.6 Hz), 4.39 (1H, t, J=5.3 Hz), 5.17 (2H, brs), 6.81–6.86 (2H, m), 6.93 (1H, m)

STARTING MATERIAL SYNTHETIC EXAMPLE 7

5-amino-2-[N,N-bis(2-hydroxyethyl)amino]benzonitrile

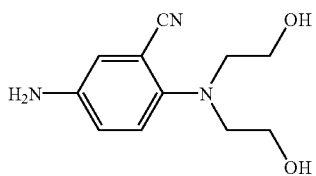

By the reaction and treatment in the same manner as in Starting Material Synthetic Example 4 using 2-chloro-5-nitrobenzonitrile (25.5 g) and diethanolamine (102 g), the title compound (24 g) was obtained. melting point: 38° C.

$^1$H-NMR (270 MHz, CDCl$_3$)δ(ppm):3.26 (4H, dd, J=5.3, 5.9 Hz), 3.60 (4H, dd, J=5.3, 5.9 Hz), 3.7–4.0 (4H, brs), 6.86–6.91 (2H, m), 7.10–7.13 (1H, m)

STARTING MATERIAL SYNTHETIC EXAMPLE 8

5-amino-2-(4-methylpiperazin-1-yl)benzonitrile

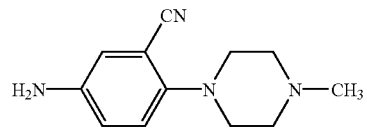

By the reaction and treatment in the same manner as in Starting Material Synthetic Example 4 using 2-chloro-5-nitrobenzonitrile (15 g) and methylpiperazine (9.8 g), the title compound (11.1 g) was obtained. melting point: 45–46° C.

STARTING MATERIAL SYNTHETIC EXAMPLE 9

5-amino-2-[4-(2-hydroxyethyl)piperidin-1-yl]benzonitrile

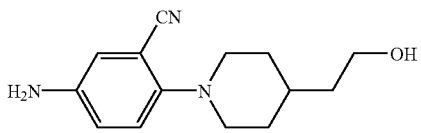

By the reaction and treatment in the same manner as in Starting Material Synthetic Example 4 using 2-chloro-5-nitrobenzonitrile (10 g) and piperidineethanol (21 g), the title compound (9.5 g) was obtained. melting point: 60–63° C.

$^1$H-NMR (270 MHz, CDCl$_3$)δ(ppm):1.44–1.53 (3H, m), 1.59–1.72 (4H, m), 2.92–2.99 (5H, m), 3.34 (2H, brs), 6.55–6.59 (2H, m), 6.76–6.81 (1H, m)

STARTING MATERIAL SYNTHETIC EXAMPLE 10

4-morpholinopiperidine

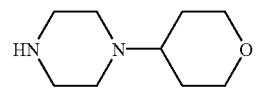

1-Ethoxycarbonyl-4-piperidone (250 g), morpholine (152.0 g) and p-toluenesulfonic acid (5 g) were added to toluene (600 ml) and the mixture was heated under reflux for 15 hr with dehydration. Then, the solvent was evaporated and the obtained oily component was added to a suspension of ethanol (1L) containing sodium borohydride (58 g) under ice-cooling. The mixture was further stirred at room temperature for 10 hr. The reaction mixture was treated with diluted hydrochloric acid and the solvent was evaporated under reduced pressure. Thereto were added 2-propanol (2 L) and potassium hydroxide (365 g) and the mixture was heated under reflux at 80° C. for 15 hr. The solvent was evaporated under reduced pressure. The obtained oily component was purified by distillation to give the title compound (168 g).

boiling point: 95–100° C./1.2 mmHg $^1$H-NMR(400 MHz, CDCl$_3$)δ(ppm): 1.3–1.4 (2H, m), 1.8–1.9 (2H, m), 2.2–2.3 (1H, m), 2.5–2.6 (4H, m), 3.1–3.2 (2H, m), 3.7–3.8 (4H, m)

STARTING MATERIAL SYNTHETIC EXAMPLE 11

4-(3,4,5,6-tetrahydro-2H-pyran-4-yl)piperazine

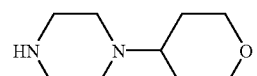

By the reaction and treatment in the same manner as in Starting Material Synthetic Example 10 using 1-ethoxycarbonylpiperazine (50 g) and 2,3,5,6-tetrahydropyran-4-one (34 g), the title compound (21 g) was obtained. boiling point: 95–100° C./5 mmHg $^1$H-NMR(400 MHz, CDCl$_3$)δ(ppm) 1.5–1.65 (2H, m), 1.7–1.8 (2H, m), 2.35–2.45 (1H, m), 2.45–2.6 (4H, m), 2.85–2.95 (4H, m), 3.3–3.45 (2H, m), 3.95–4.1 (2H, m).

STARTING MATERIAL SYNTHETIC EXAMPLE 12

5-amino-2-(4-morpholinopiperidin-1-yl)benzonitrile

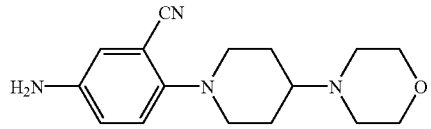

By the reaction and treatment in the same manner as in Starting Material Synthetic Example 4 using 2-chloro-5-nitrobenzonitrile (10 g) and 4-morpholinopiperidine (27 g), the title compound (9.4 g) was obtained. melting point: 84–86° C.

$^1$H-NMR (400 MHz, DMSO-d$_6$)δ(ppm):1.49–1.57 (2H, m), 1.86 (2H, d, J=11.2 Hz), 2.20–2.25 (1H, m), 2.42–2.58 (4H, m), 2.59–2.64 (2H, m), 3.20 (2H, d, J=11.2 Hz), 3.58 (4H, m), 5.18 (2H, brs), 6.79–6.80 (2H, m), 6.93–6.95 (1H, m).

STARTING MATERIAL SYNTHETIC EXAMPLE 13

5-amino-2-(1-benzylpiperidine-4-yloxy)benzonitrile

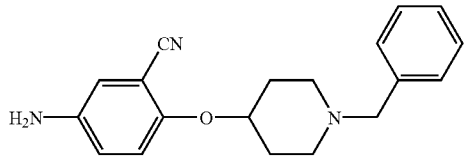

By the reaction and treatment in the same manner as in Starting Material Synthetic Example 4 using 2-chloro-5-nitrobenzonitrile (10 g) and 1-benzyl-4-hydroxypiperidine (11.5 g), the title compound (7 g) was obtained as an oil.

$^1$H-NMR (400 MHz, CDCl$_3$)δ(ppm):1.80–1.98 (5H, m), 2.33 (2H, m), 2.70–2.85 (2H, m), 3.52 (2H, s), 3.59 (2H, brs), 4.29 (1H, m), 6.81–6.83 (8H, m).

STARTING MATERIAL SYNTHETIC EXAMPLE 14

5-amino-2-[4-(3,4,5,6-tetrahydro-2H-pyran-4-yl)piperazin-1-yl]benzonitrile

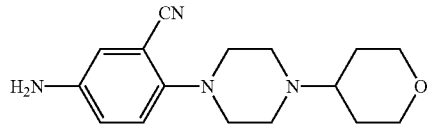

By the reaction and treatment in the same manner as in Starting Material Synthetic Example 4 using 2-chloro-5-nitrobenzonitrile (10 g) and 4-(3,4,5,6-tetrahydro-2H-pyran-4-yl)piperazine (27 g), the title compound (10.5 g) was obtained. melting point: 162° C.

$^1$H-NMR (400 MHz, DMSO-d$_6$)δ(ppm):1.39–1.43 (2H, m), 1.71 (2H, d, J=11.7 Hz), 2.38–2.50 (1H, m), 2.52–2.63 (4H, brs), 2.86–2.97 (4H, brs), 3.28 (2H, dd, J=11.2, 11.7 Hz), 3.88 (2H, d, J=9.7 Hz), 5.19 (2H, brs), 6.81 (2H, brs), 6.92–6.94 (1H, m)

STARTING MATERIAL SYNTHETIC EXAMPLE 15

5-amino-2-(3-hydroxy-2,2-dimethylpropoxy)benzonitrile

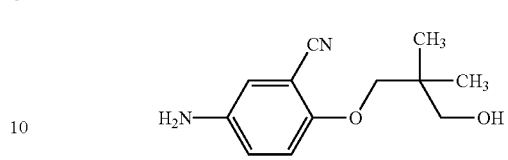

By the reaction and treatment in the same manner as in Starting Material Synthetic Example 2 using 2-chloro-5-nitrobenzonitrile (10 g) and 2,2-dimethyl-1,3-propanediol (5.7 g), the title compound (7.2 g) was obtained. melting point: 194–196° C.

STARTING MATERIAL SYNTHETIC EXAMPLE 16

5-amino-2-(4-piperidinopiperidin-1-yl)benzonitrile

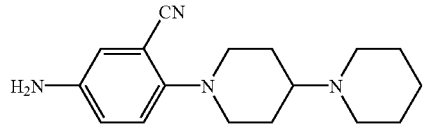

By the reaction and treatment in the same manner as in Starting Material Synthetic Example 4 using 2-chloro-5-nitrobenzonitrile (3.9 g) and piperidinopiperidine (7.2 g), the title compound (6.2 g) was obtained. melting point: 134–135° C.

STARTING MATERIAL SYNTHETIC EXAMPLE 17

6-isopropylthieno[2,3-b]pyridine-2-carboxylic acid

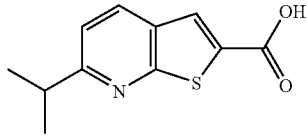

(1) 3-Cyano-6-isopropyl-2-mercaptopyridine (50 g) synthesized according to U.S. Pat. No. 5,001,137 (Mar. 19, 1991), sodium ethoxide (22.9 g) and bromoethyl acetate (34.2 ml) were added to ethanol (500 ml) and the mixture was stirred at room temperature for 1 hr and the solvent was evaporated. The residue was recrystallized from ethanol to give ethyl 3-amino-6-isopropylthieno[2,3-b]pyridine-2-carboxylate (69.3 g) (melting point: 161–162° C.).

(2) This ester (30 g) and isoamyl nitrite (45.7 ml) were added to tetrahydrofuran (300 ml) and the mixture was stirred at 60° C. for 2 hr and the solvent was evaporated under reduced pressure. The residue was separated and purified by silica gel column chromatography (mobile phase; chloroform) to give ethyl 6-isopropylthieno[2,3-b]pyridine-2-carboxylate (7.1 g). melting point: 73–74° C.

(3) This was subjected to hydrolysis under basic conditions according to a conventional method to give the title compound (5.8 g). melting point: 218–220° C.

$^1$H-NMR (270 MHz, DMSO-d$_6$)δ(ppm):1.28 (6H, d, J=7.2 Hz), 3.10–3.25 (1H, m), 7.44 (1H, d, J=7.6 Hz), 8.14 (1H, s), 8.32 (1H, d, J=7.6 Hz).

STARTING MATERIAL SYNTHETIC EXAMPLE 18

3-hydroxy-6-isopropylthieno[2,3-b]pyridine-2-carboxylic acid methyl ester

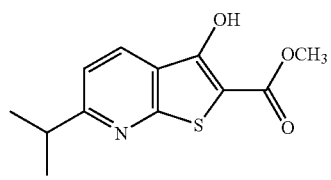

Under ice-cooling, metal sodium (6.9 g) was added to methanol (70 ml)-and methyl thioglycolate (32 g) was added with stirring. Ethyl 2-chloro-6-isopropylpyridine-3-carboxylate (42 g) synthesized according to U.S. Pat. No. 5,001,137 (Mar. 19, 1991) was dissolved in dimethylformamide (170 ml) and the mixture was stirred at room temperature for 2 hr. The reaction mixture was treated with water, and the organic layer was extracted with ethyl acetate, washed with saturated brine and dried over anhydrous magnesium sulfate. The solvent was evaporated under reduced pressure. The obtained crystals were recrystallized from water-containing methanol to give the title compound (20.9 g). melting point: 80–81° C.

$^1$H-NMR (270 MHz, CDCl$_3$)δ(ppm):1.35 (6H, d, J=7.2 Hz), 3.10–3.25 (1H, m), 3.96 (3H, s), 7.44 (1H, d, J=7.6 Hz), 8.14 (1H, d, J=7.6 Hz), 10.19 (1H, s).

EXAMPLE 1

3-amino-N-(2,4-dichlorophenyl)-6-methoxybenzofuran-2-carboxamide ¼ hydrate

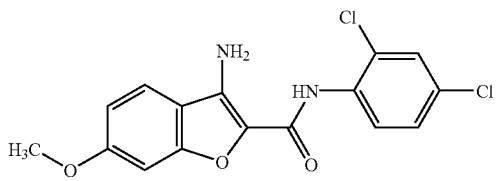

2-Hydroxy-4-methoxybenzonitrile (3 g) synthesized according to the method described in JP-A-8-253466 was dissolved in dimethylformamide (20 ml) and potassium tert-butoxide (5 g) was added under ice-cooling. After stirring for 30 min, 2-chloro-N-(2,4-dichlorophenyl) acetamide was added and the mixture was further stirred for 1 hr. Then water (20 ml) was added and the crystals were precipitated. The crystals were added to ethanol (20 ml) to give a solution, to which sodium ethoxide (0.6 mg) was added. The mixture was stirred at 78° C. for 1 hr and cooled to give the title compound (1.36 g). melting point: 187–188° C.

$^1$H-NMR (270 MHz, DMSO-d$_6$)δ(ppm):3.84(3H, s), 6.35 (2H, brs), 6.91 (1H, dd, J=2.0, 8.6 Hz), 7.07 (1H, d, J=2.0 Hz), 7.44 (1H, dd, J=2.6, 8.6 Hz), 7.70 (1H, d, J=2.6 Hz), 7.81 (1H, d, J=8.6 Hz), 8.09 (1H, d, J=8.6 Hz), 8.68 (1H, brs).

EXAMPLE 2

N-(2,4-dichlorophenyl)-6-methoxy-3-ureido-1-benzofuran-2-carboxamide

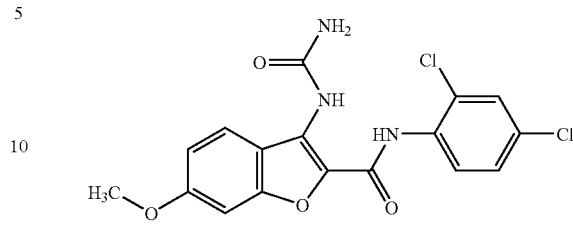

3-Amino-N-(2,4-dichlorophenyl)-6-methoxybenzofuran-2-carboxamide ¼ hydrate (0.9 g) obtained in Example 1 was dissolved in dichloromethane (10 ml) and chlorosulfonyl isocyanate (0.4 g) was added under ice-cooling. The mixture was further stirred at room temperature for 1 hr. Then water was added and the precipitated crystals were recrystallized from water-containing dimethylformamide to give the title compound (0.3 g). melting point: >260° C.

$^1$H-NMR (270 MHz, DMSO-d$_6$)δ(ppm):3.86 (3H, s), 6.73 (2H, brs), 6.93 (1H, dd, J=2.6, 9.2 Hz), 7.11 (1H, d, J=2.6 Hz), 7.48 (1H, dd, J=2.0, 8.6 Hz), 7.73 (1H, d, J=2.0 Hz), 7.85 (1H, d, J=8.6 Hz), 8.16 (1H, d, J=9.2 Hz), 9.03 (1H, brs), 9.94 (1H, brs).

EXAMPLE 3

[2-(N-(3-cyano-4-neopentyloxyphenyl)carbamoyl)indol-1-yl]ethyl acetate

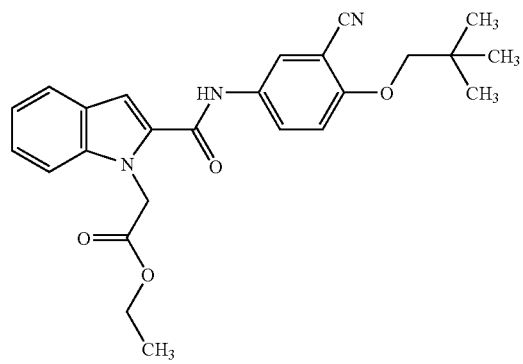

1-(Ethoxycarbonylmethyl)indole-2-carboxylic acid (2 g) obtained by reacting 1H-indol-2-carboxylic acid with potassium carbonate and bromoethyl acetate in dimethylformamide, 5-amino-2-neopentyloxybenzonitrile (1.6 g), triethylamine (2.4 g) and diethyl cyanophosphate (2 g) were added to dimethylformamide solution (20 ml) and the mixture was stirred at room temperature for 1 hr. Then the reaction mixture was treated with diluted hydrochloric acid and the organic layer was extracted with ethyl acetate. The extract solution was washed with aqueous sodium hydrogencarbonate solution and saturated brine and dried over anhydrous magnesium sulfate. The solvent was evaporated. Methanol was added to the residue to allow crystallization and the crystals were recrystallized from water-containing methanol to give the title compound (2.3 g). melting point: 169–170° C.

$^1$H-NMR (270 MHz, DMSO-d$_6$)δ(ppm):1.09 (9H, s), 1.32 (3H, t, J=7.3 Hz), 3.67 (2H, s), 4.24 (2H, q, J=7.3 Hz), 5.38 (2H, s), 7.04 (1H, s), 7.08–7.13 (1H, m), 7.22–7.29 (2H, m), 7.55–7.60 (2H, m), 7.61–7.64 (1H, m), 8.09 (1H, s), 10.61 (1H, s).

EXAMPLE 4

[2-(N-(3-cyano-4-neopentyloxyphenyl)carbamoyl)indol-1-yl]acetic acid

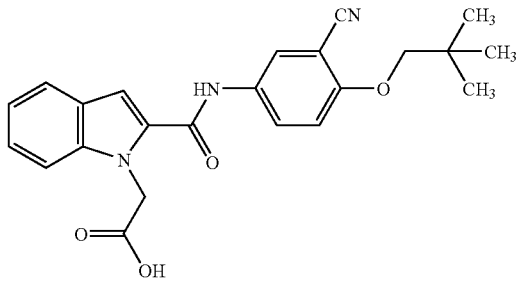

By hydrolysis of [2-(3-cyano-4-neopentyloxyphenylcarbamoyl)indol-1-yl]ethyl acetate (1.3 g) obtained in Example 3 according to a conventional method using sodium hydroxide, the title compound (0.4 g) was obtained. melting point: 194–195° C.

$^1$H-NMR (270 MHz, DMSO-d$_6$)δ(PPM):1.04 (9H, s), 3.79 (2H, s), 5.34 (2H, s), 7.12–7.18 (1H, m), 7.24–7.34 (2H, m), 7.13 (1H, s), 7.60 (1H, d, J=7.9 Hz), 7.71 (1H, d, J=8.9 Hz), 7.94 (1H, dd, J=2.6, 9.2 Hz), 8.07 (1H, d, J=2.6 Hz) 10.43 (1H, s).

EXAMPLE 5

N-(3-cyano-4-neopentyloxyphenyl)benzo[b]thiophene-2-carboxamide

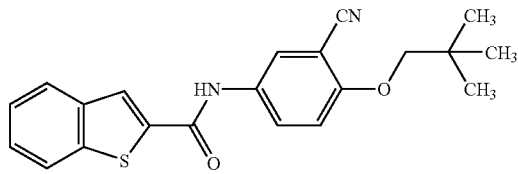

By the reaction and treatment in the same manner as in Example 3 using benzo[b]thiophene-2-carboxylic acid (1.5 g) and 5-amino-2-neopentyloxyphenylbenzonitrile (1.7 g), the title compound (1.9 g) was obtained. melting point: 227° C.

$^1$H-NMR (270 MHz, CDCl$_3$)δ(PPM):1.09 (9H, s), 3.69 (2H, s), 6.92 (1H, d, J=9.2 Hz), 7.39–7.49 (2H, m), 7.78 (1H, d, J=2.4 Hz), 7.80–7.89 (3H, m), 7.91 (1H, s), 8.00 (1H, brs).

EXAMPLE 6

N-(3-cyano-4-phenoxyphenyl)-5-fluoro-2-methyl-1H-indole-3-carboxamide

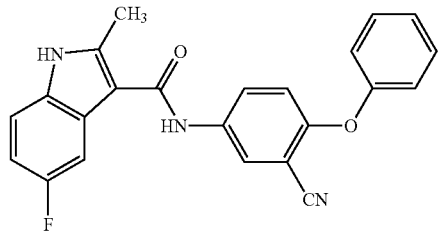

5-Fluoro-2-methyl-1H-indole-3-carboxylic acid (1.2 g) and thionyl chloride (0.9 g) were added to dichloroethane (10 ml) and the mixture was stirred at 83° C. for 1 hr and the solvent was evaporated. A solution (10 ml) of 5-amino-2-phenoxybenzonitrile (1.3 g) in pyridine was added at room temperature and the mixture was stirred for 1 hr. Water was added to the reaction mixture, and the organic layer was extracted with ethyl acetate and dried over anhydrous magnesium sulfate. The solvent was evaporated. Diisopropyl ether was added to the residue to allow crystallization and the crystals were recrystallized from hydrous dimethylformamide to give the title compound (0.3 g). melting point: 237° C.

$^1$H-NMR (270 MHz, DMSO-d$_6$)δ(ppm):2.63 (3H, s), 6.95–7.00 (1H, m), 7.10–7.12 (3H, m), 7.20–7.25 (1H, m), 7.34–7.44 (1H, m), 7.45–7.56 (3H, m), 7.96 (1H, dd, J=2.2, 8.8 Hz), 8.24 (1H, d, J=2.2 Hz), 9.84 (1H, s), 11.78 (1H, s).

EXAMPLE 7

N-(3-cyano-4-piperidinophenyl)benzo[b]thiophene-2-carboxamide

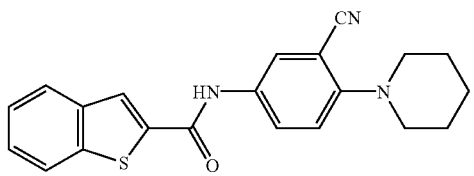

By the reaction and treatment in the same manner as in Example 6 using benzo[b]thiophene-2-carboxylic acid (1.7 g) and 5-amino-2-piperidinobenzonitrile (2.0 g), the title compound (1.0 g) was obtained. melting point: 219–245° C.

EXAMPLE 8

N-[3-cyano-4-(4-hydroxypiperidin-1-yl)phenyl]-5-fluoro-2-methyl-1H-indole-3-carboxamide

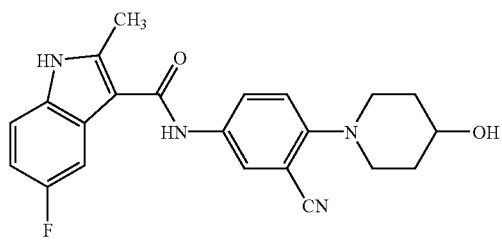

By the reaction and treatment in the same manner as in Example 6 using 5-fluoro-2-methyl-1H-indole-3-carboxylic acid (0.9 g) and 5-amino-2-(4-hydroxypiperidin-1-yl)benzonitrile (1.1 g), the title compound (0.6 g) was obtained. melting point: 169–171° C.

$^1$H-NMR (270 MHz, DMSO-d$_6$)δ(ppm):1.53–1.66 (2H, m), 1.88–1.91 (2H, m), 2.62 (3H, s), 2.83–2.91 (2H, m), 3.29–3.35 (2H, m), 3.62–3.69 (1H, m), 4.71 (1H, d, J=4.6 Hz), 6.96 (1H, dt, J=2.6, 9.2 Hz), 7.17 (1H, d, J=9.2 Hz), 7.35 (1H, dd, J=4.6, 8.6 Hz), 7.43–7.48 (1H, m), 7.86 (1H, dd, J=2.6, 9.2 Hz), 8.05 (1H, d, J=2.6 Hz), 9.63 (1H, s), 11.74 (1H, s).

EXAMPLE 9

N-(3-cyano-4-neopentyloxyphenyl)-5-fluoro-2-methyl-1H-indole-3-carboxamide ½ hydrate

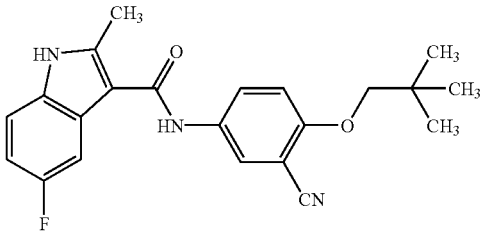

By the reaction and treatment in the same manner as in Example 6 using 5-fluoro-2-methyl-1H-indole-3-carboxylic acid (1 g) and 5-amino-2-neopentyloxybenzonitrile (1.1 g), the title compound (0.6 g) was obtained. melting point: 169–171° C.

$^1$H-NMR (270 MHz, CH$_3$OD)δ(ppm):1.10 (9H, s), 3.72 (2H, s), 6.91 (1H, dt, J=2.6, 6.6 Hz), 6.97 (1H, d, J=8.6 Hz), 7.28 (1H, dd, J=4.6, 8.6 Hz), 7.41–7.46 (1H, m), 7.80 (1H, dd, J=2.6, 8.6 Hz), 7.87 (1H, d, J=2.6 Hz), 8.38 (1H, s), 10.82 (1H, s).

EXAMPLE 10

[3-(N-(3-cyano-4-(4-hydroxypiperidin-1-yl)phenyl)carbamoyl)-5-fluoro-2-methylindol-1-yl]acetic acid

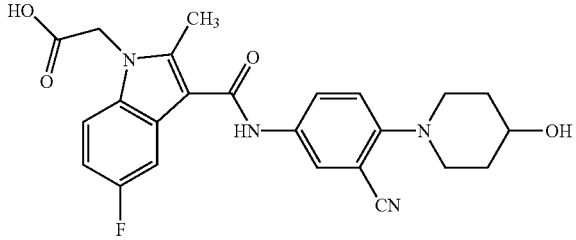

By the reaction and treatment in the same manner as in Example 3 using 1-(ethoxycarbonylmethyl)-5-fluoro-2-methyl-indole-2-carboxylic acid (3 g) obtained by reacting 5-fluoro-2-methyl-1H-indole-2-carboxylic acid with potassium carbonate and bromoethyl acetate in dimethylformamide and 5-amino-2-(4-hydroxypiperidin-1-yl)benzonitrile (3.2 g), the title compound (1.4 g) was obtained.

melting point: >250° C.

$^1$H-NMR (270 MHz, DMSO-d$_6$)δ (ppm):1.59–1.66 (2H, m), 1.87–1.91 (2H, m), 2.62 (3H, s), 2.73–2.91 (2H, m), 3.30–3.34 (2H, m), 3.63–3.69 (1H, m), 4.6–4.7 (1H, brs), 5.10 (2H, s), 7.02 (1H, dt, J=2.6, 9.2 Hz), 7.17 (1H, d, J=9.2 Hz), 7.45 (1H, dd, J=2.6, 9.9 Hz), 7.52 (1H, dd, J=4.6, 9.2 Hz), 7.86–7.90 (1H, m), 8.07 (1H, d, J=2.6 Hz), 9.86 (1H, s).

EXAMPLE 11

N-[3-cyano-4-(4-(2-hydroxyethyl)piperazin-1-yl)phenyl]benzo[b]thiophene-2-carboxamide

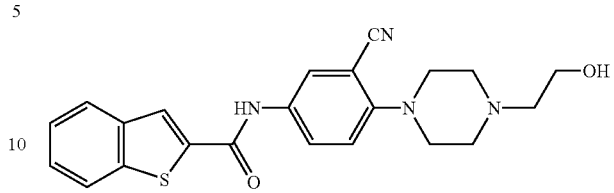

By the reaction and treatment in the same manner as in Example 6 using benzo[b]thiophene-2-carboxylic acid (1 g) and 5-amino-2-[4-(2-hydroxyethyl)piperazin-1-yl]benzonitrile (1.2 g), the title compound (0.8 g) was obtained. melting point: 238–239° C.

$^1$H-NMR (270 MHz, DMSO-d$_6$)δ(ppm):2.45–2.52 (2H, m), 2.59–2.61 (4H, m), 3.11–3.14 (4H, m), 3.55 (2H, q, J=5.9 Hz), 4.43 (1H, t, J=5.9 Hz), 7.21 (1H, d, J=9.2 Hz), 7.47–7.51 (2H, m), 7.91 (1H, dd, J=2.6, 9.2 Hz), 7.96–8.03 (1H, d, J=2.6 Hz), 8.03 (1H, d, J=2.6 Hz), 8.09 (1H, d, J=2.6 Hz), 8.34 (1H, s), 10.63 (1H, s).

EXAMPLE 12

N-[3-cyano-4-(4-hydroxypiperidin-1-yl)phenyl]benzo[b]thiophene-2-carboxamide

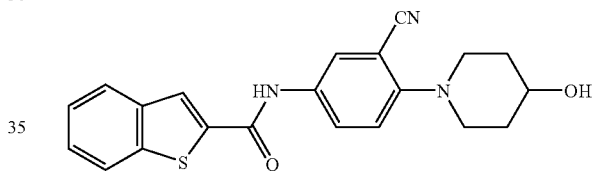

By the reaction and treatment in the same manner as in Example 6 using benzo[b]thiophene-2-carboxylic acid (4 g) and 5-amino-2-(4-hydroxypiperidin-1-yl)benzonitrile (4 g), the title compound (2.8 g) was obtained. melting point: 224–225° C.

$^1$H-NMR (270 MHz, DMSO-d$_6$)δ(ppm):1.54–1.67 (2H, m), 1.88–1.92 (2H, m), 2.86–2.91 (2H, m), 3.27–3.38 (2H, m), 3.44–3.71 (1H, m), 4.74 (1H, d, J=4.6 Hz), 7.20 (1H; d, J=9.2 Hz), 7.45–7.54 (2H, m), 7.90 (1H, dd, J=2.6, 9.2 Hz), 7.98–8.07 (2H, m), 8.08 (1H, d, J=2.6 Hz), 8.10 (1H, s), 10.62 (1H, brs).

EXAMPLE 13

N-[3-cyano-4-(4-hydroxypiperidin-1-yl)phenyl]-N-methylbenzo[b]thiophene-2-carboxamide

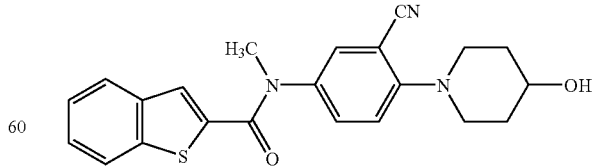

N-[3-Cyano-4-(4-hydroxypiperidin-1-yl)phenyl]benzo[b]thiophene-2-carboxamide (2.0 g) obtained in Example 12, tertiary butyldimethylsilyl chloride (0.9 g) and imidazole (0.4 g) were added to dimethylformamide (20 ml) and the mixture was stirred at room temperature for 12 hr. Then the reaction mixture was treated with water and the organic layer was extracted with ethyl acetate. The extract was washed with aqueous sodium hydrogencarbonate solution and dried over anhydrous magnesium sulfate. The solvent was evaporated under reduced pressure and the obtained residue was dissolved in dimethylformamide. Under ice-cooling, sodium hydride (60% contained, 0.2 g) (was added and the mixture was stirred for 1 hr and methyl iodide (0.6 g) was added. The mixture was further stirred for 1 hr. The reaction mixture was treated with water and the organic layer was extracted with toluene. The extract was washed with water and the solvent was evaporated under reduced pressure. To the residue were added tetrabutylammonium fluoride (0.93 g) and tetrahydrofuran(15 ml) and the mixture was stirred at 60° C. for 4.5 hr. Then the solvent was evaporated and the residue was separated and purified by silica gel column chromatography (mobile phase: chloroform) to give the title compound (0.8 g). melting point: 211–212° C.

$^1$H-NMR (270 MHz, DMSO-$d_6$)δ(ppm):1.15–1.67 (2H, m), 1.86–1.92 (2H, m), 2.92–3.16 (2H, m), 3.35 (3H, s), 3.35–3.44 (2H, m), 3.61–3.72 (1H, m), 4.74 (1H, d, J=4.6 Hz), 7.14 (1H, d, J=8.6 Hz), 7.22 (1H, s), 7.34–7.40 (2H, m), 7.53 (1H, dd, J=2.6, 8.6 Hz), 7.76–7.80 (1H, m), 7.84 (1H, d, J=2.6 Hz), 7.90 (1H, d, J=7.9 Hz).

EXAMPLE 14

1-(2-acetyloxyethyl)-N-(3-cyano-4-neopentyloxyphenyl)-5-fluoro-2-methylindole-3-carboxamide

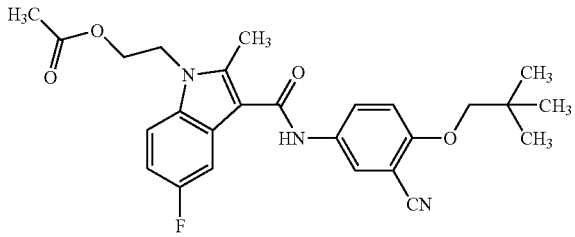

N-(3-Cyano-4-neopentyloxyphenyl)-5-fluoro-2-methyl-1H-indole-3-carboxamide ¼ hydrate (0.8 g) obtained in Example 9,. potassium carbonate (0.2 g) and 2-bromoethyl acetate (0.4 g) were added to dimethylformamide (5 ml) and the mixture was stirred at 40° C. for 3 hr. Then the reaction mixture was treated with water and the oganic layer was extracted with ethyl acetate. The extract was dried over anhydrous magnesium sulfate and the solvent was evaporated. The residue was separated and purified by silica gel column chromatography (mobile phase: chloroform) to give the title compound (0.3 g). melting point: 124–125° C.

$^1$H-NMR (270 MHz, CDCl$_3$)δ(ppm):1.10 (9H, s), 1.99 (3H, s), 2.76 (3H, s), 3.70 (2H, s), 4.32–4.38 (4H, m), 6.94 (1H, d, J=9.2 Hz), 7.00 (1H, dt, J=2.6, 6.6 Hz), 7.31 (1H, dd, J=4.6, 9.2 Hz), 7.40 (1H, dd, J=2.6, 9.2 Hz), 7.50 (1H, brs), 7.74 (1H, dd, J=2.6, 9.2 Hz), 7.82 (1H, d, J=2.6 Hz).

EXAMPLE 15

[3-(N-(4-[N,N-bis(2-hydroxyethyl)amino]-3-cyanophenyl)carbamoyl)-5-fluoro-2-methylindol-1-yl]acetic acid ½ hydrate

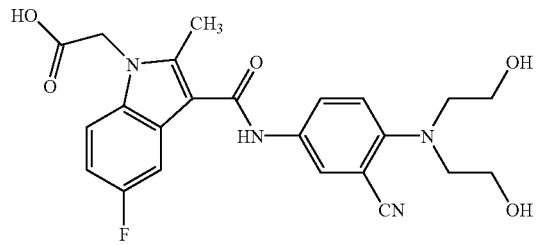

By the reaction and treatment in the same manner as in Examples 3 and 4 using 5-fluoro-2-methylindole-3-carboxylic acid (1.0 g) and 5-amino-2-[N,N-bis(2-hydroxyethyl)amino]benzonitrile (0.9 g), the title compound (0.6 g) was obtained. melting point: 150–153° C.

$^1$H-NMR (270 MHz, DMSO-$d_6$)δ(ppm):2.55 (3H, s), 2.67 (2H, s), 3.45 (4H, t, J=5.9 Hz), 3.56 (4H, t, J=5.9 Hz), 5.09 (2H, brs), 7.02 (1H, dt, J=2.6, 6.6 Hz), 7.19 (1H, d, J=9.2 Hz), 7.44 (1H, dd, J=2.6, 9.9 Hz), 7.49–7.54 (1H, m), 7.77–7.82 (1H, m), 7.98 (1H, d, J=2.6 Hz), 9.79 (1H, s).

EXAMPLE 16

N-[4-(N,N-bis(2-hydroxyethyl)amino)-3-cyanophenyl]benzo[b]thiophene-2-carboxamide ¼ hydrate

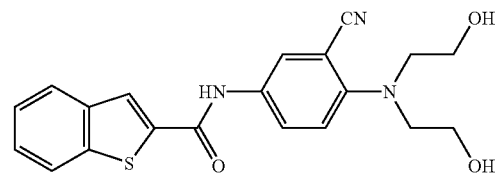

By the reaction and treatment in the same manner as in Example 6 using benzo[b]thiophene-2-carboxylic acid (1.0 g) and 5-amino-2-[N,N-bis(2-hydroxyethyl)amino]benzonitrile (0.9 g), the title compound (0.3 g) was obtained. melting point: 163–168° C.

$^1$H-NMR (400 MHz, DMSO-$d_6$)δ:3.49 (4H, t, J=5.9 Hz), 3.55 (4H, t, J=5.9 Hz), 4.65 (2H, brs), 7.19 (1H, d, J=9.3 Hz), 7.45–7.51 (2H, m), 7.79 (1H, dd, J=2.5, 9.3 Hz), 7.98 (1H, d, J=3 Hz), 7.99–8.01 (1H, m), 8.04–8.06 (1H, m), 8.30 (1H, s), 10.54 (1H, brs)

EXAMPLE 17

N-[3-cyano-4-(4-methylpiperazin-1-yl)phenyl]benzo[b]thiophene-2-carboxamide

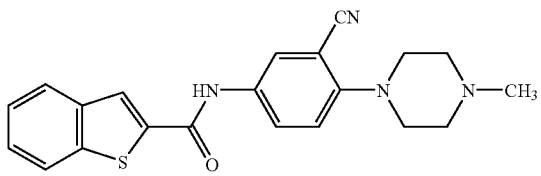

By the reaction and treatment in the same manner as in Example 6 using benzo[b]thiophene-2-carboxylic acid (1.3 g) and 5-amino-2-(4-methylpiperazin-1-yl)benzonitrile (1.6 g), the title compound (1.0 g) was obtained. melting point: 263–264° C.

$^1$H-NMR (270 MHz, DMSO-d$_6$)δ:2.24 (3H, s), 3.13–3.14 (4H, m), 3.34–3.35 (4H, m), 7.21 (1H, d, J=9.2 Hz), 7.47–7.51 (2H, m), 7.90–7.93 (1H, m), 8.00–8.08 (2H, m), 8.09 (1H, d, J=2.6 Hz), 8.32 (1H, s), 10.64 (1H, s).

EXAMPLE 18

N-[3-cyano-4-(4-hydroxypiperidin-1-yl)phenyl]-4,5,6,7-tetrahydrobenzo[b]thiophene-3-carboxamide

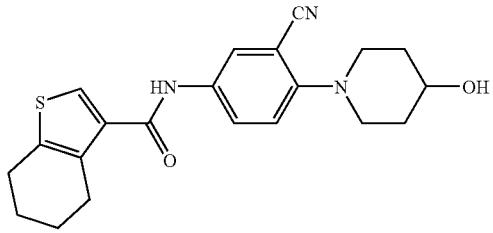

By the reaction and treatment in the same manner as in Example 6 using 4,5,6,7-tetrahydrobenzo[b]thiophene-3-carboxylic acid (1.2 g) and 5-amino-2-(4-hydroxypiperidin-1-yl)benzonitrile (1.3 g), the title compound (1.2 g) was obtained. melting point: 172–173° C.

$^1$H-NMR (270 MHz, DMSO-d$_6$)δ:1.55–1.63 (2H, m), 1.64–1.80 (4H, m), 1.86–1.90 (2H, m), 2.7–2.8 (4H, M), 2.87 (2H, t, J=9.2 Hz), 3.29–3.34 (2H, m), 3.65–3.68 (1H, m), 4.70 (1H, m), 6.98 (1H, d, J=8.6 Hz), 7.83 (1H, dd, J=2.6, 8.6 Hz), 7.92 (1H, s), 8.03 (1H, d, J=2.6 Hz), 10.10 (1H, s).

EXAMPLE 19

N-[3-cyano-4-(4-(2-hydroxyethyl)piperidin-1-yl)phenyl]benzo[b]thiophene-2-carboxamide

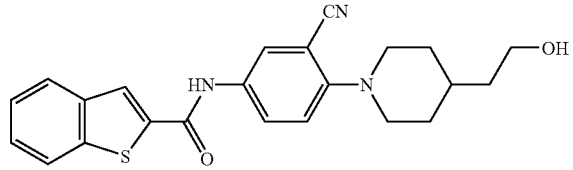

By the reaction and treatment in the same manner as in Example 6 using benzo[b]thiophene-2-carboxylic acid (1.5 g) and 5-amino-2-[4-(2-hydroxyethyl)piperidin-1-yl]benzonitrile (1.4 g), the title compound (0.8 g) was obtained. melting point: 218° C.

$^1$H-NMR (270 MHz, DMSO-d$_6$)δ:1.31–1.40 (2H, m), 1.42–1.45 (2H, m), 1.50–1.60 (1H, m), 1.79–1.85 (2H, m), 2.73–2.89 (2H, m), 3.38–3.46 (4H, m), 4.39–4.42 (1H, m), 7.21 (1H, d, J=8.2 Hz), 7.48–7.54 (2H, m), 7.89–7.92 (1H, m), 7.92–8.00 (1H, m), 8.03–8.07 (1H, m), 8.08 (1H, d, J=2.6 Hz), 8.23 (1H, s), 10.62 (1H, s)

EXAMPLE 20

N-{3-cyano-4-[4-(2-hydroxyethyl)piperidin-1-yl]phenyl}benzo[b]furan-2-carboxamide

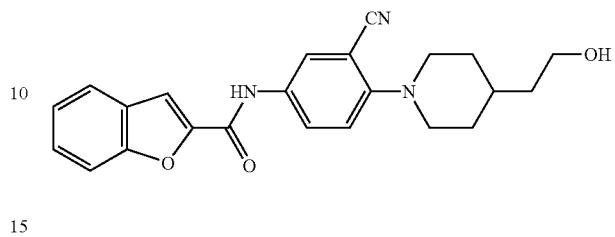

By the reaction and treatment in the same manner as in Example 7 using benzo[b]furan-2-carboxylic acid (2 g) and 5-amino-2-[4-(2-hydroxyethyl)piperidin-1-yl]benzonitrile (3 g), the title compound (0.5 g) was obtained. melting point: 214° C.

$^1$H-NMR (270 MHz, CDCl$_3$)δ:1.40–1.75 (5H, m), 1.85 (2H, d, J=12.5 Hz), 2.80 (2H, t, J=11.9 Hz), 3.57 (2H, d, J=12.5 Hz), 3.75 (2H, m), 7.02 (1H, d, J=9.2 Hz), 7.30–7.36 (1H, m), 7.47 (1H, t, J=7.3 Hz), 7.54 (1H, s), 7.57 (1H, dd, J=2.6, 8.6 Hz), 7.70 (1H, d, J=7.3 Hz), 7.82 (1H, dd, J=2.6, 8.6 Hz), 7.92 (1H, d, J=2.6 Hz), 8.28 (1H, s)

EXAMPLE 21

N-[3-cyano-4-(4-morpholinopiperidin-1-yl)phenyl]benzo[b]thiophene-2-carboxamide monohydrochloride

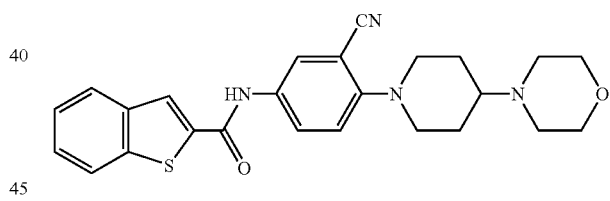

Benzo[b]thiophene-2-carboxylic acid (1 g) and thionyl chloride (0.9 g) were added to dichloroethane (10 ml) and the mixture was stirred at 83° C. for 1 hr. The solvent was evaporated and thereto was added a solution (10 ml) of 5-amino-2-(4-morpholinopiperidin-1-yl)benzonitrile (1.3 g) in pyridine at room temperature and the mixture was stirred for 1 hr. Then water was added to the reaction mixture and the organic layer was extracted with ethyl acetate. The extract was dried over anhydrous magnesium sulfate and the solvent was evaporated. Diluted hydrochloric acid was added to the residue to allow crystallization and the crystals were recrystallized from water-containing methanol to give the title compound (0.3 g). melting point: >270° C.

$^1$H-NMR (400 MHz, DMSO-d$_6$)δ:1.70–1.85 (2H, m), 2.12–2.30 (3H, m), 2.40–2.55 (4H, m), 2.71–2.80 (2H, m), 3.42–3.50 (4H, m), 3.55–3.62 (2H, m), 7.17 (1H, d, J=8.6 Hz), 7.38–7.44 (2H, m), 7.87 (1H, dd, J=1.9, 9.2 Hz), 7.92 (1H, d, J=7.3 Hz), 7.92 (1H, d, J=7.3 Hz), 8.03 (1H, d, J=1.9 Hz), 8.28 (1H, s), 10.67 (1H, s)

EXAMPLE 22

3-chloro-N-[3-cyano-4-(4-morpholinopiperidin-1-yl)phenyl]benzo[b]thiophene-2-carboxamide

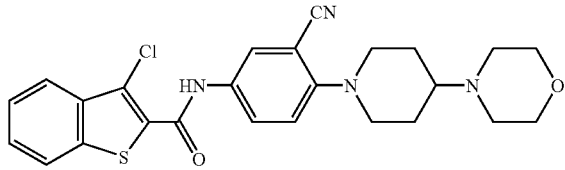

By the reaction and treatment in the same manner as in Example 6 using 3-chlorobenzo[b]thiophene-2-carboxylic acid (1.1 g) and 5-amino-2-(4-morpholinopiperidin-1-yl)benzonitrile (1.5 g), the title compound (1.3 g) was obtained. melting point: 227–228° C.

$^1$H-NMR (400 MHz, DMSO-$d_6$)δ:1.55–1.59 (2H, m), 1.90 (2H, d, J=11.3 Hz), 2.28–2.31 (1H, m), 2.49–2.52 (4H, m), 2.80 (2H, dd, J=11.3, 11.7 Hz), 3.50 (2H, d, J=12.2 Hz), 3.52–3.60 (4H, m), 7.21 (1H, d, J=9.2 Hz), 7.62–7.64 (2H, m), 7.85 (1H, dd, J=2.4, 9.3 Hz), 7.94 (1H, d, J=2.9, 5.8 Hz), 8.03 (1H, d, J=2.4 Hz), 8.15 (1H, dd, J=2.9, 5.8 Hz), 10.65 (1H, s).

EXAMPLE 23

N-[3-cyano-4-(4-piperidinopiperidin-1-yl)phenyl]benzo[b]thiophene-2-carboxamide ⅕ hydrate

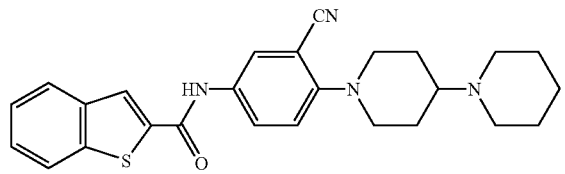

By the reaction and treatment in the same manner as in Example 6 using benzo[b]thiophene-2-carboxylic acid (1.0 g) and 5-amino-2-(4-piperidinopiperidin-1-yl)benzonitrile (1.4 g), the title compound (0.6 g) was obtained. melting point: 275° C.

$^1$H-NMR (400 MHz, DMSO-$d_6$)δ:1.38–1.42 (2H, m), 1.45–1.52 (4H, m), 17.58–1.66 (2H, m), 1.83 (2H, d, J=11.3 Hz), 2.33–2.39 (1H, m), 2.47–2.51 (4H, m), 2.77 (2H, dd, J=11.3, 11.8 Hz), 3.51 (2H, d, J=12.2 Hz), 7.20 (1H, d, J=8.8 Hz), 7.46–7.53 (2H, m), 7.89 (1H, dd, J=2.5, 8.8 Hz), 8.01 (2H, dd, J=2.5, 8.8 Hz), 8.08 (1H, d, J=2.5 Hz), 8.33 (1H, s), 10.63 (1H, s).

EXAMPLE 24

N-[4-(1-benzylpiperidin-4-yloxy)-3-cyanophenyl]benzo[b]thiophene-2-carboxamide

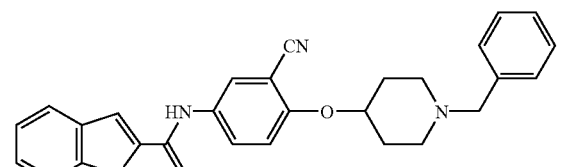

By the reaction and treatment in the same manner as in Example 6 using benzo[b]thiophene-2-carboxylic acid (0.7 g) and 5-amino-2-(1-benzylpiperidine-4-yloxy)benzonitrile (1.2 g), the title compound (0.6 g) was obtained. melting point: 206° C.

$^1$H-NMR (400 MHz, DMSO-$d_6$)δ:1.70–1.73 (2H, m), 1.93–1.96 (2H, m), 2.29–2.33 (2H, m), 2.62–2.68 (2H, m), 3.50 (2H, s), 4.60–4.63 (1H, m), 7.23–7.33 (5H, m), 7.37 (1H, d, J=9.3 Hz), 7.48–7.53 (2H, m), 7.92 (1H, dd, J=2.5, 9.3 Hz), 8.01–8.03 (2H, m), 8.08 (1H, d, J=2.5 Hz), 8.32 (1H, s), 10.64 (1H, s).

EXAMPLE 25

N-[4-(1-benzylpiperidin-4-yloxy)-3-cyanophenyl]benzo[b]furan-2-carboxamide

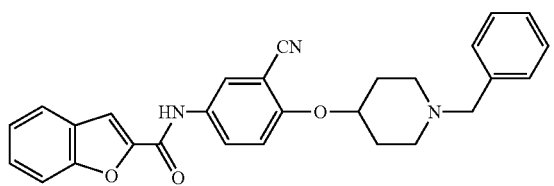

By the reaction and treatment in the same manner as in Example 6 using benzo[b]furan-2-carboxylic acid (1.2 g) and 5-amino-2-(1-benzylpiperidin-4-yloxy)benzonitrile (2.2 g), the title compound (1.3 g) was obtained. melting point: 175° C.

$^1$H-NMR (400 MHz, DMSO-$d_6$)δ:1.68–1.72 (2H, m), 1.94–1.97 (2H, m), 2.29–2.33 (2H, m), 2.49–2.52 (2H, m), 3.50 (2H, s), 4.60–4.63 (1H, m), 7.23–7.28 (1H, m), 7.32–7.40 (5H, m), 7.50–7.54 (1H, m), 7.72 (1H, d, J=8.3 Hz), 7.76 (1H, s), 7.83 (1H, d, J=7.9 Hz), 8.00 (1H, dd, J=2.5, 9.2 Hz), 8.14 (1H, d, J=2.5 Hz), 8.43 (1H, s), 10.70 (1H, s).

EXAMPLE 26

N-[3-cyano-4-(4-(3,4,5,6-tetrahydro-2H-pyran-4-yl)piperazin-1-yl)phenyl]benzo[b]thiophene-2-carboxamide

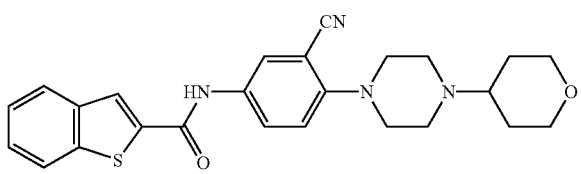

By the reaction and treatment in the same manner as in Example 6 using benzo[b]thiophene-2-carboxylic acid (0.4 g) and 5-amino-2-[4-(3,4,5,6-tetrahydro-2H-pyran-4-yl)piperazin-1-yl]benzonitrile (0.6 g), the title compound (0.6 g) was obtained. melting point: >285° C.

$^1$H-NMR (270 MHz, DMSO-$d_6$)δ:1.41–1.47 (2H, m), 1.75 (2H, d, J=12.2 Hz), 2.42–2.50 (1H, m), 2.63–2.70 (4H, m), 3.30–3.35 (4H, m), 3.90 (2H, d, J=12.2 Hz), 7.22 (1H, d, J=8.8 Hz), 7.46–7.53 (2H, m), 7.91 (1H, dd, J=2.4, 8.8 Hz), 8.02–8.08 (2H, m), 8.10 (1H, d, J=2.4 Hz), 8.33 (1H, s), 10.60 (1H, brs).

EXAMPLE 27

N-(3-cyano-4-neopentyloxyphenyl)-6-isopropylthieno[2,3-b]pyridine-2-carboxamide

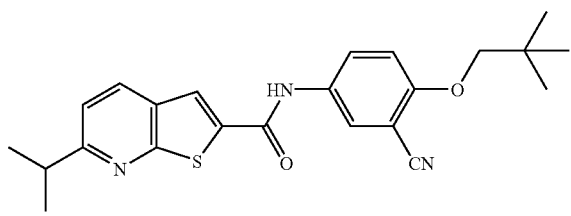

By the reaction and treatment in the same manner as in Example 6 using 6-isopropylthieno[2,3-b]pyridine-2-carboxylic acid (2 g) and 5-amino-2-neopentyloxybenzonitrile (1.9 g), the title compound (0.6 g) was obtained. melting point: 244–245° C.

$^1$H-NMR (270 MHz, DMSO-d$_6$)δ:1.04 (9H, s), 1.30 (6H, d, J=6.6 Hz), 3.13–3.23 (1H, m), 3.80 (2H, s), 7.28 (1H, d, J=9.2 Hz), 7.45 (1H, d, J=8.6 Hz), 7.95 (1H, dd, J=2.6, 9.2 Hz), 8.06 (1H, d, J=2.6 Hz), 8.25 (1H, s), 8.34 (1H, d, J=8.6 Hz), 10.66 (1H, brs).

EXAMPLE 28

N-(3-cyano-4-neopentyloxyphenyl)-3-hydroxy-6-isopropylthieno[2,3-b]pyridine-2-carboxamide

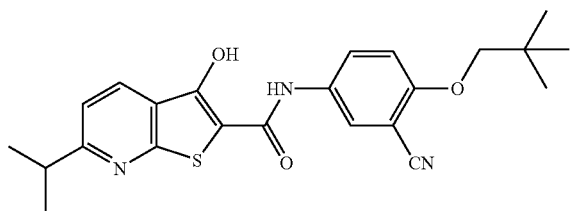

Methyl 3-hydroxy-6-isopropylthieno[2,3-b]pyridine-2-carboxylate (1.6 g) and 5-amino-2-neopentyloxybenzonitrile (2.6 g) were stirred at 170° C. for 2 hr. Then the reaction mixture was treated with diluted hydrochloric acid and the organic layer was extracted with ethyl acetate. The extract was washed with brine and dried over anhydrous magnesium sulfate. The solvent was evaporated under reduced pressure. The obtained crystals were recrystallized from water-containing dimethylformamide to give the title compound (0.6 g). melting point: 211–212° C.

$^1$H-NMR (270 MHz, CD$_3$OD)δ:1.10 (9H, s), 1.37 (6H, d, J=7.3 Hz), 3.10–3.22 (1H, m), 3.72 (2H, s), 6.98 (1H, d, J=9.2 Hz), 7.30 (1H, d, J=8.6 Hz), 7.86 (1H, dd, J=2.6, 9.2 Hz), 7.91 (1H, d, J=2.6 Hz), 8.18 (1H, brs), 8.30 (1H, d, J=8.6 Hz).

EXAMPLE 29

N-[3-cyano-4-(2,2-dimethyl-3-hydroxypropoxy)phenyl]benzo[b]thiophene-2-carboxamide

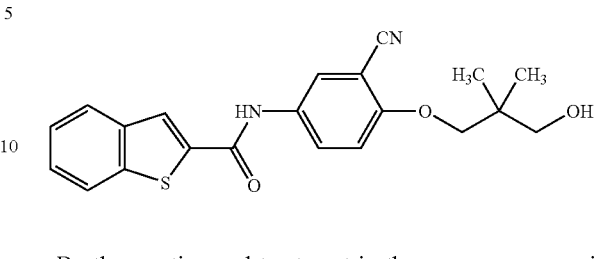

By the reaction and treatment in the same manner as in Example 6 using benzo[b]thiophene-2-carboxylic acid (0.77 g), 5-amino-2-(2,2-dimethyl-3-hydroxypropoxy)benzonitrile monohydrochloride (1.0 g) and triethylamine (0.6 ml), the title compound (0.45 g) was obtained. melting point: 188–189° C.

$^1$H-NMR (400 MHz, DMSO-d$_6$)δ:0.96 (6H, s), 3.32 (2H, d, J=5.4 Hz), 3.86 (2H, s), 4.70 (1H, t, J=5.8 Hz), 7.29 (1H, d, J=9.2 Hz), 7.45–7.55 (2H, m), 7.95 (1H, dd, J=9.2, 2.4 Hz), 8.0–8.1 (3H, m), 8.33 (1H, s), 10.65 (1H, brs).

EXAMPLE 30

N-[3-cyano-4-(2,2-dimethyl-3-hydroxypropoxy)phenylbenzo[b]furan-2-carboxamide

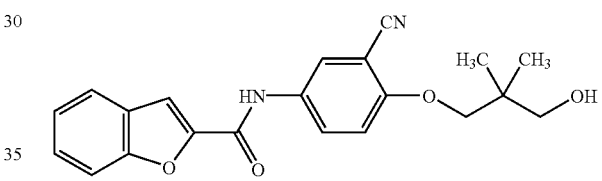

By the reaction and treatment in the same manner as in Example 6 using benzo[b]furan-2-carboxylic acid (0.7 g), 5-amino-2-(2,2-dimethyl-3-hydroxypropoxy)benzonitrile monohydrochloride (1.0 g) and triethylamine (0.6 ml), the title compound (0.26 g) was obtained. melting point: 199–201° C.

$^1$H-NMR (400 MHz, DMSO-d$_6$)δ:0.95 (6H, s), 3.31 (2H, s), 3.84 (2H, s), 4.69 (1H, s), 7.27 (1H, d, J=8.8 Hz), 7.37 (1H, t, J=6.8 Hz), 7.51 (1H, t, J=6.8, Hz), 7.7–7.85 (3H, m), 7.95–8.05 (1H, m), 8.1–8.2 (1H, m), 10.69 (1H, brs).

EXAMPLE 31

N-[3-cyano-4-(2,2-dimethyl-3-hydroxypropoxy)phenyl]-4,5,6,7-tetrahydrobenzo[b]thiophene-3-carboxamide

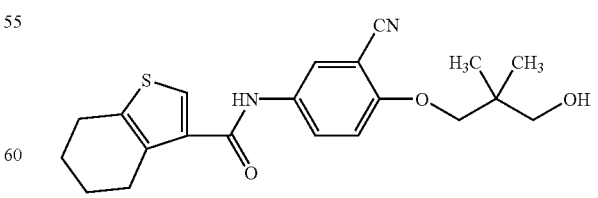

By the reaction and treatment in the same manner as in Example 6 using 4,5,6,7-tetrahydrobenzo[b]thiophene-3-carboxylic acid (0.78 g) and 5-amino-2-(2,2-dimethyl-3-hydroxypropoxy)benzonitrile monohydrochloride (1.0 g)

and triethylamine (0.6 ml), the title compound (0.87 g) was obtained. melting point: 148–150° C.

$^1$H-NMR (400 MHz, DMSO-d$_6$)δ:0.94 (6H, s), 1.7–1.8 (4H, m), 2.7–2.8 (4H, m), 3.30 (2H, s), 3.89 (2H, s), 4.68 (1H, s), 7.22 (1H, d, J=8.8 Hz), 7.87 (1H, d, J=8.8 Hz), 7.92 (1H, s), 8.02 (1H, s), 10.12 (1H, brs).

EXAMPLE 32

N-[3-cyano-4-(4-hydroxypiperidin-1-yl)phenyl]naphthalene-2-carboxamide

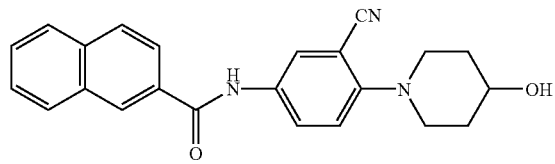

By the reaction and treatment in the same manner as in Example 6 using naphthalene-2-carboxylic acid (0.44 g) and 5-amino-2-(4-hydroxypiperidin-1-yl)benzonitrile (0.5 g), the title compound (0.58 g) was obtained. melting point: 183–185° C.

$^1$H-NMR (400 MHz, DMSO-d$_6$)δ:1.55–1.65 (2H, m), 1.85–1.95 (2H, m), 2.85–2.95 (2H, m), 3.3–3.4 (2H, m), 3.65–3.70 (1H, m), 4.74 (1H, d, J=4.4 Hz), 7.23 (1H, d, J=8.8 Hz), 7.6–7.7 (2H, m), 7.9–8.2 (6H, m), 8.57 (1H, s), 10.55 (1H, brs).

EXAMPLE 33

N-[3-cyano-4-(4-hydroxypiperidin-1-yl)phenyl]-1,2,3,4-tetrahydronaphthalene-2-carboxamide

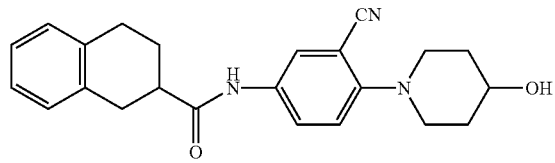

By the reaction and treatment in the same manner as in Example 6 using 1,2,3,4-tetrahydronaphthalene-2-carboxylic acid (0.45 g) and 5-amino-2-(4-hydroxypiperidin-1-yl)benzonitrile (0.58 g), the title compound (0.57 g) was obtained. melting point: 163–165° C.

$^1$H-NMR (400 MHz, DMSO-d$_6$)δ:1.5–1.6 (2H, m), 1.7–1.8 (1H, m), 1.8–1.9 (2H, m), 2.0–2.1 (1H, m), 2.55–2.65 (1H, m), 2.8–2.95 (6H, m), 3.2–3.3 (2H, m), 3.6–3.7 (1H, m), 4.71 (1H, d, J=4.4 Hz), 7.05–7.1 (4H, m), 7.16 (1H, d, J=8.8 Hz), 7.70 (1H, d, J=8.8 Hz), 9.99 (1H, s), 10.13 (1H, brs).

In the same manner as in the above-mentioned Starting Material Synthetic Examples and Examples, the following compounds can be produced.

EXAMPLE 34
N-[3-cyano-4-[4-(3,4,5,6-tetrahydro-2H-pyran-4-yl)piperazin-1-yl]phenyl]benzimidazole-5-carboxamide EXAMPLE 35
N-[3-cyano-4-(4-morpholinopiperidin-1-yl)phenyl]benzimidazole-5-carboxamide EXAMPLE 36
N-[3-cyano-4-[4-(2-hydroxyethyl)piperazin-1-yl]phenyl]benzimidazole-5-carboxamide EXAMPLE 37
N-(3-cyano-4-neopentyloxyphenyl)benzimidazole-5-carboxamide EXAMPLE 38
N-[3-cyano-4-[4-(3,4,5,6-tetrahydro-2H-pyran-4-yl)piperazin-1-yl]phenyl]-1-benzopyran-4(4H)-one-2-carboxamide EXAMPLE 39
N-[3-cyano-4-(4-morpholinopiperidin-1-yl)phenyl]-1-benzopyran-4(4H)-one-2-carboxamide EXAMPLE 40
N-[3-cyano-4-[4-(2-hydroxyethyl)piperazin-1-yl]phenyl]-1-benzopyran-4(4H)-one-2-carboxamide EXAMPLE 41
N-(3-cyano-4-neopentyloxyphenyl)-1-benzopyran-4(4H)-one-2-carboxamide EXAMPLE 42
N-[3-cyano-4-[4-(3,4,5,6-tetrahydro-2H-pyran-4-yl)piperazin-1-yl]phenyl]coumarin-3-carboxamide EXAMPLE 43
N-[3-cyano-4-(4-morpholinopiperidin-1-yl)phenyl]coumarin-3-carboxamide EXAMPLE 44
N-[3-cyano-4-[4-(2-hydroxyethyl)piperazin-1-yl]phenyl]coumarin-3-carboxamide EXAMPLE 45
N-(3-cyano-4-neopentyloxyphenyl)coumarin-3-carboxamide EXAMPLE 46
N-[3-cyano-4-[4-(3,4,5,6-tetrahydro-2H-pyran-4-yl)piperazin-1-yl]phenyl]-3,4-methylenedioxybenzamide EXAMPLE 47
N-[3-cyano-4-(4-morpholinopiperidin-1-yl)phenyl]-3,4-methylenedioxybenzamide EXAMPLE 48
N-[3-cyano-4-[4-(2-hydroxyethyl)piperazin-1-yl]phenyl]-3,4-methylenedioxybenzamide EXAMPLE 49
N-(3-cyano-4-neopentyloxyphenyl)-3,4-methylenedioxybenzamide EXAMPLE 50
N-[3-cyano-4-[4-(3,4,5,6-tetrahydro-2H-pyran-4-yl)piperazin-1-yl]phenyl]quinoxaline-2-carboxamide EXAMPLE 51
N-[3-cyano-4-(4-morpholinopiperidin-1-yl)phenyl]quinoxaline-2-carboxamide EXAMPLE 52
N-[3-cyano-4-[4-(2-hydroxyethyl)piperazin-1-yl]phenyl]quinoxaline-2-carboxamide EXAMPLE 53
N-(3-cyano-4-neopentyloxyphenyl)quinoxaline-2-carboxamide EXAMPLE 54
N-[3-cyano-4-[4-(3,4,5,6-tetrahydro-2H-pyran-4-yl)piperazin-1-yl]phenyl]-isoquinoline-3-carboxamide

EXAMPLE 55

N-[3-cyano-4-(4-morpholinopiperidin-1-yl)phenyl]-isoquinoline-3-carboxamide

EXAMPLE 56

N-[3-cyano-4-[4-(2-hydroxyethyl)piperazin-1-yl]phenyl]-isoquinoline-3-carboxamide

EXAMPLE 57

N-(3-cyano-4-neopentyloxyphenyl)-isoquinoline-3-carboxamide

EXAMPLE 58

N-[3-cyano-4-[4-(3,4,5,6-tetrahydro-2H-pyran-4-yl)piperazin-1-yl]phenyl]-4-methoxyquinoline-2-carboxamide

EXAMPLE 59

N-[3-cyano-4-(4-morpholinopiperidin-1-yl)phenyl]-4-methoxyquinoline-2-carboxamide

EXAMPLE 60

N-[3-cyano-4-[4-(2-hydroxyethyl)piperazin-1-yl]phenyl]-4-methoxyquinoline-2-carboxamide

EXAMPLE 61

N-(3-cyano-4-neopentyloxyphenyl)-4-methoxyquinoline-2-carboxamide

EXAMPLE 62

N-[3-cyano-4-[4-(3,4,5,6-tetrahydro-2H-pyran-4-yl)piperazin-1-yl]phenyl]-4,5,6,7-tetrahydrothieno[2,3-c]pyridine-2-carboxamide

EXAMPLE 63

N-[3-cyano-4-(4-morpholinopiperidin-1-yl)phenyl]-4,5,6,7-tetrahydrothieno[2,3-c]pyridine-2-carboxamide

EXAMPLE 64

N-[3-cyano-4-[4-(2-hydroxyethyl)piperazin-1-yl]phenyl]-4,5,6,7-tetrahydrothieno[2,3-c]pyridine-2-carboxamide

EXAMPLE 65

N-(3-cyano-4-neopentyloxyphenyl)-4,5,6,7-tetrahydrothieno[2,3-c]pyridine-2-carboxamide The structural formulas of the compounds of the above-mentioned Examples 34 to 65 are shown in the following.

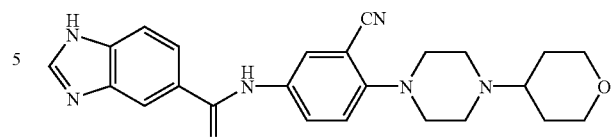

34

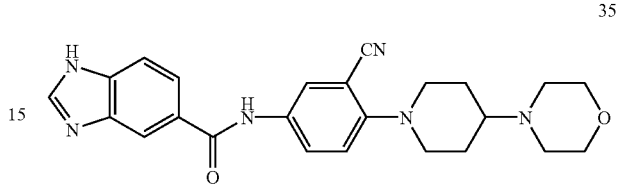

35

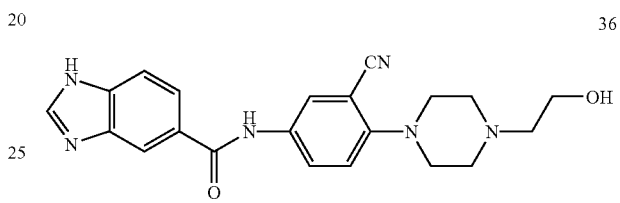

36

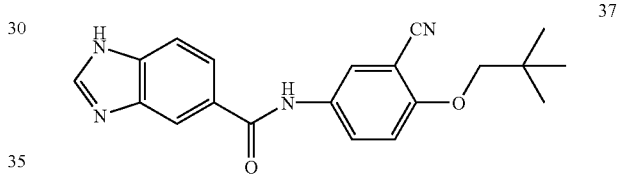

37

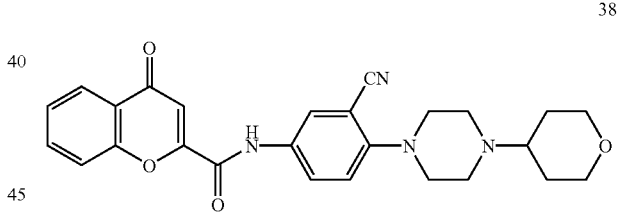

38

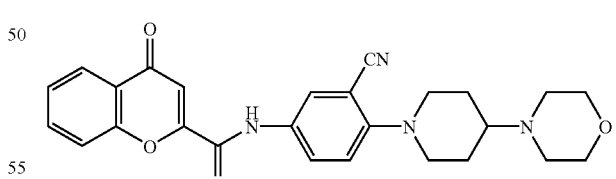

39

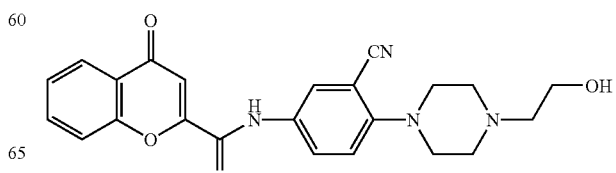

40

-continued
41
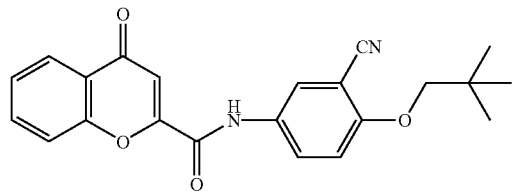
42
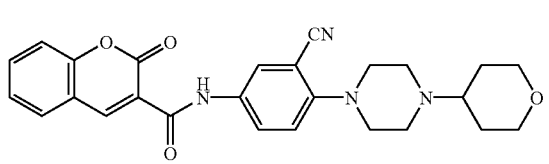
43
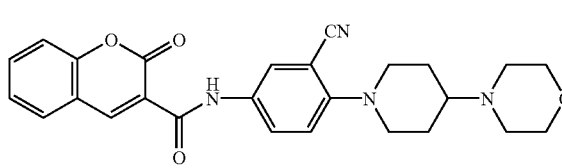
44
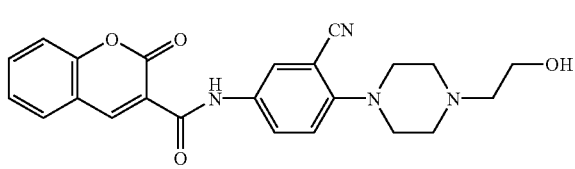
45
46
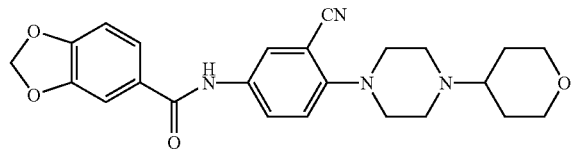
47
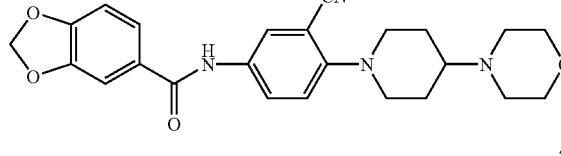
48
49
-continued
50
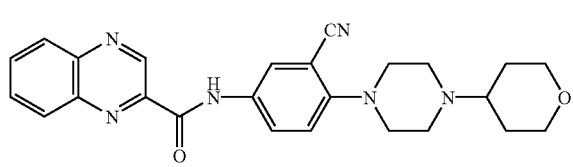
51
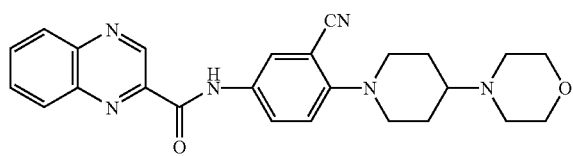
52
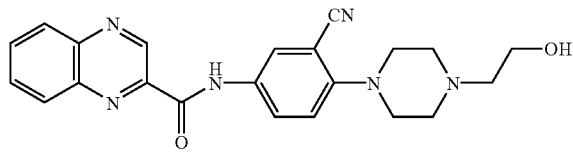
53
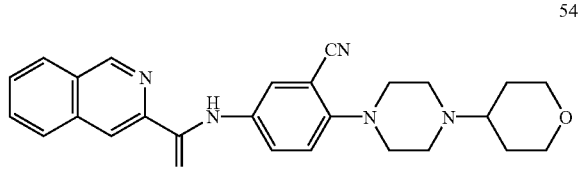
54
55
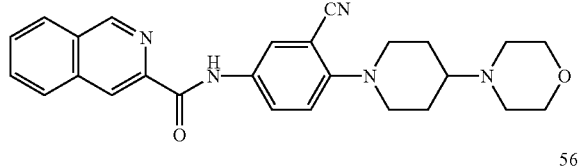
56
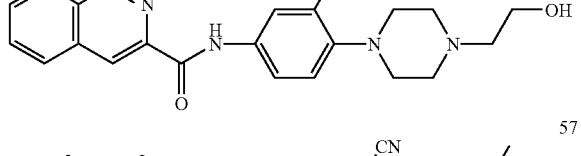
57
58
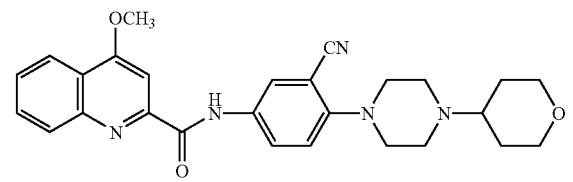

59

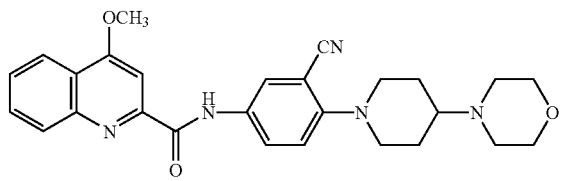

60

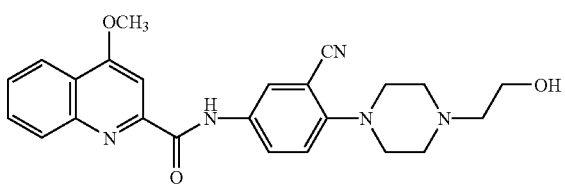

61

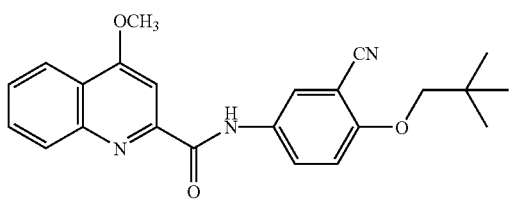

62

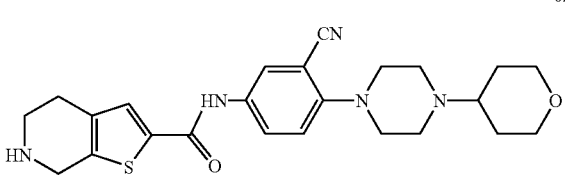

63

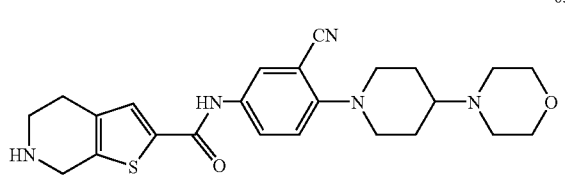

64

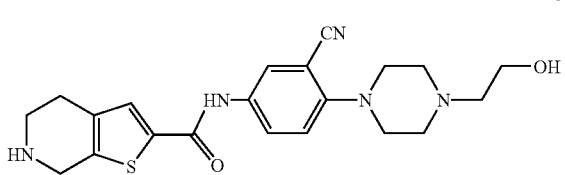

65

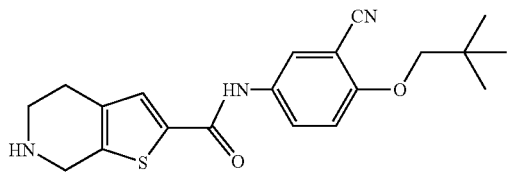

| Formulation Example 1 | (mg) |
|---|---|
| Compound of the present invention | 10.0 |
| Lactose | 109.6 |
| Microrystalline cellulose | 27.4 |

| Formulation Example 1 | (mg) |
|---|---|
| Light silicic anhydride | 1.5 |
| Magnesium stearate | 1.5 |
| | 150.0 (one tablet) |

The compound of the present invention (30 g), lactose (328.8 g) and microcrystalline cellulose (82.2 g) are mixed. The mixture is compression-shaped using a roller compactor to give a flake compression product. Using a hammer mill, the flake compression product is pulverized and the pulverized product is passed through a 20 mesh sieve. Light silicic anhydride (4.5 g) and magnesium stearate (4.5 g) were added to the sieved product and the mixture was tableted with a punch having a diameter of 7.5 mm to give 3000 tablets weighing 150 mg per tablet.

The pharmacological activity of the compound of the present invention and a pharmaceutically acceptable salt thereof can be evaluated by determining the inhibitory activity thereof in in vitro proliferation reaction of lymphocytes of mouse, rat, dog, monkey or human activated by antigen or mitogen, lymphocyte proliferation reaction dependent on cytokines such as IL-2, IL-4, IL-7, IL-9, IL-13 and IL-15, and the like, or production test of inflammatory cytokines such as TNF-α, IL-1, IL-6, IL-12, IL-15, IL-18 and the like, which is induced by lymphocyte, macrophage, dendritic cell and the like by the addition of IL-15, lipopolysaccharide and the like. The compound of the present invention and a pharmaceutically acceptable salt thereof show a significant inhibitory activity at a concentration of 0.001–100 μM in the above-mentioned in vitro tests as compared to control group free of addition of the compound.

In addition, the in vivo pharmacological activity of the compound of the present invention and a pharmaceutically acceptable salt thereof can be evaluated by inhibitory effect on type II collagen-induced arthritis by the immunization of mouse, rat, dog or monkey with type II collagen derived from bovine or a suitable mammal together with Freund's complete adjuvant, and by intravenously, intraperitoneally, subcutaneously or orally administering the compound of the present invention or a pharmaceutically acceptable salt thereof. Besides the above-mentioned tests, similar evaluation is possible in an autoimmune disease model such as adjuvant arthritis, experimental encephalomyelitis and the like in rat or mouse. In addition, the treatment effect of the compound of the present invention and a pharmaceutically acceptable salt thereof on autoimmune diseases can be evaluated by the use of MRL/MpJ-lpr/lpr mouse, (NZB×NZW)F1 mouse or BXSB mouse that spontaneously develops an autoimmune disease similar to systemic lupus erythematosus in human, while using, as indices, expression of proteinuria associated with lupus nephritis, production amount of anti-self antibody such as anti-DNA antibody, rheumatoid factor, antierythrocyte antibody, anti-type II collagen antibody and the like, infiltration and proliferation of activated lymphocyte in inflammatory site, survival days and the like. The compound of the present invention and a pharmaceutically acceptable salt thereof show a significant inhibitory activity or a treatment effect in the above-mentioned in vivo pharmacological tests, by intravenous, intraperitoneal, subcutaneous or oral administration of 0.1–100 mg/kg body weight, as compared to the control group given a vehicle alone. In the following, Experimental Examples are given for explanation.

EXPERIMENTAL EXAMPLE 1

Action on the Proliferation of Rat Lymphocytes Stimulated by Phorbol 12-myristate 13-acetate (PMA) and Calcium Ionophore A23187

An RPMI1640 medium (Sigma) was used as a medium, to which kanamycin sulfate (60 μg/ml) and penicillin G potassium (100 units/ml) were added, and then 10% of fetal calf serum (FCS, Gibco) inactivated at 56° C. for 30 min was added and used for the test. The compound of the present invention or a pharmaceutically acceptable salt thereof was dissolved in dimethyl sulfoxide and diluted with the 10% FCS-containing RPMI1640 medium to a desired concentration and used for the test.

The spleens were aseptically removed from 6-week-old male F344 rats or LEW rats (Charles River Japan, Inc.) and minced with tweezers in RPMI1640 medium and then prepared into a single cell suspension of splenic cell. After hematolysis by a hypotonicity treatment using a 9:1 mixed solution of 0.83% aqueous ammonium chloride solution and Tris-HCl buffer (pH 7.65), the suspension was passed through a nylon wool column to give nylon non-adhesive T cell concentration fraction for use. The cell suspension prepared using 10% FCS-containing RPMI1640 medium was added to a flat 96 well microtest plate at $5 \times 10^5$ cells/ well. The compound of the present invention or a pharmaceutically acceptable salt thereof at a concentration of 0.0001–100 μM, 10 ng/ml of PMA and 100 ng/ml of A23187 were added and the mixture was cultured at 37° C., 5% carbon dioxide and 95% air for 44 hr. After the completion of the culture, tritium thymidine (18.5 kBq/well, specific activity: 185 GBq/mmol, Amersham Pharmacia Biotech) was added and the mixture was cultured at 37° C., 5% carbon dioxide, 95% air for further 4 hr. Then using a cell harvester, the cells were recovered on a glass fiber filter, and using a scintillation counter (MicroBeta 1460) for plate, the radioactivity taken into the cells was measured, and the proliferation of rat lymphocyte induced by stimulation with PMA and A23187 was measured. To be specific, the inhibition rate was calculated by the following formula based on average tritium thymidine uptake (cpm) by lymphocyte in the wells to which various concentrations of the compound of the present invention were added.

$$(\%) \text{ inhibition} = \left(1 - \frac{\text{radioactivity (cpm) of well with addition of compound}}{\text{radioactivity (cpm) of well without addition of compound}}\right) \times 100$$

Based on the dose-response curve obtained by plotting average value of tritium thymidine uptake (cpm) or inhibition rate in the longitudinal axis and concentration in the horizontal axis, the concentration ($IC_{50}$) of the compound that inhibits the level to 50% of the value of the control group was determined by nonlinear regression.

The compound of the present invention and a pharmaceutically acceptable salt thereof showed a significant and concentration-dependent inhibitory activity as compared to the control group free of addition of the compound in the above-mentioned in vitro test, wherein the specific $IC_{50}$ values of the compounds of Example 6, Example 11, Example 20 and Example 28 were 0.39 μM, 1.5 μM, 0.23 μM and 2.0 μM, respectively.

EXPERIMENTAL EXAMPLE 2

Effect on IL-2, IL-4, IL-7, IL-9, IL-13 or IL-15-Dependent Proliferation of IL-2-Dependent Mouse CTLL-2 Cell, D10.G4.1 Cell or HT2 Cell An RPMI1640 medium (Sigma) was used as a medium, to which kanamycin sulfate (60 μg/ml) and penicillin G potassium (100 units/ml) were added, and then 10% of fetal calf serum (FCS, Gibco) inactivated at 56° C. for 30 min was added and used for the test. The compound of the present invention or a pharmaceutically acceptable salt thereof was dissolved in dimethyl sulfoxide and diluted with the 10% FCS-containing RPMI1640 medium to a desired concentration and used for the test.

Using IL-2-dependent mouse CTLL-2 cells, D10.G4.1 cells or HT2 cells (purchased from American Type Culture Collection), the IL-2, IL-4, IL-7, IL-9, IL-13 or IL-15-dependent proliferation was measured with tritium thymidine uptake into the cell as an index.

The CTLL-2 cells, D10.G4.1 cells or HT2 cells were prepared to a concentration of $10^5$ cells/ml using RPMI1640 medium containing 10% FCS and $5 \times 10^{-5}$ M of 2-mercaptoethanol, and added to 96 well microtest plate at $10^4$ cells/well. Then 0.01–10 ng/ml recombinant human, monkey or mouse IL-2, IL-4, IL-7, IL-9, IL-13 or IL-15 (Genzyme/Techne) and the compound of the present invention or a pharmaceutically acceptable salt thereof at a concentration of 0.0001–100 μM were added and the mixture was cultured at 37° C., 5% carbon dioxide and 95% air for 20–92 hr. After the completion of the culture, tritium thymidine (18.5 kBq/well, specific activity: 185 GBq/mmol, Amersham Pharmacia Biotech) was added and the mixture was cultured at 37° C., 5% carbon dioxide, 95% air for further 4 hr. Then using a cell harvester, the cells were recovered on a glass fiber filter, and using a scintillation counter (MicroBeta 1460) for plate, the radioactivity taken into the cells was measured, and IL-2, IL-4, IL-7, IL-9, IL-13 or IL-15-dependent proliferation of T cell was measured. To be specific, the inhibition rate was calculated by the following formula based on average tritium thymidine uptake (cpm) by lymphocyte in the wells to which various concentrations of the compound of the present invention were added.

$$(\%) \text{ inhibition} = \left(1 - \frac{\text{radioactivity (cpm) of well with addition of compound}}{\text{radioactivity (cpm) of well without addition of compound}}\right) \times 100$$

Based on the dose-response curve obtained by plotting average value of tritium thymidine uptake (cpm) or inhibition rate in the longitudinal axis and concentration in the horizontal axis, the concentration ($IC_{50}$) of the compound that inhibits the level to 50% of the value of the control group was determined by nonlinear regression.

The compound of the present invention and a pharmaceutically acceptable salt thereof showed a significant and concentration-dependent inhibitory activity as compared to the control group free of addition of the compound in the above-mentioned in vitro test.

EXPERIMENTAL EXAMPLE 3

Effect on Production of IL-1, IL-6, IL-12, IL-15, IL-18, TNF-α from Mouse Macrophage or Macrophage-like Cell Line J774A.1 Cells An RPMI1640 medium (Sigma) is used as a medium, to which kanamycin sulfate (60 μg/ml) and penicillin G potassium (100 units/ml) is added, and then 10% of fetal calf serum (FCS, Gibco) inactivated at 56° C. for 30 min is added and used for the test. The compound of the present invention or a pharmaceutically acceptable salt thereof is dissolved in dimethyl sulfoxide and diluted with the 10% FCS-containing RPMI1640 medium to a desired concentration and used for the test.

A 10% proteose peptone (Difco) solution is intraperitoneally administered to 7-week-old male C57BL/6 mouse (Charles River Japan, Inc.) and 4 days later, intraperitoneally infiltrated cells are recovered, and after incubation in 24 well plate for 1 hr and removal of non-adherent cells, used as macrophage. To the single cell layer (monolayer) of macrophage obtained by the aforementioned operation or mouse macrophage-like cell line J774A.1 (purchased from American Type Culture Collection) is added 0.1–10 μg/ml of lipopolysaccharide (Difco) or 0.01–10 ng/ml of recombinant human, monkey or mouse IL-15 (Genzyme) and the compound of the present invention or a pharmaceutically acceptable salt thereof at a concentration of 0.0001–100 μM and the mixture is cultured at 37° C., 5% carbon dioxide and 95% air for 12–96 hr. After the completion of the culture, culture supernatant is recovered and IL-1, IL-6, IL-12, IL-15, IL-18, TNF-α produced in the supernatant is quantitated by the enzyme antibody method (ELISA), based on which the cytokine production inhibitory activity is evaluated. In addition, the activity of IL-1, IL-6, IL-12, IL-15, IL-18, TNF-α produced in the supernatant is also evaluated by a bioassay using a dependent cell line. In addition, the total RNA in the cells is recovered and mRNA of the cytokine is amplified by the reverse transcriptase-polymerase chain reaction (RT-PCR). The expression of various cytokine mRNAs is semi-quantitatively determined using hypoxanthine-guanine phosphoribosyltransferase as a control mRNA, and used as an index of cytokine production. The inhibition rate is calculated by the following formula based on average cytokine production amount or average mRNA expression amount when various concentrations of the compound of the present invention are added.

$$(\%)\ \text{inhibition} = \left(1 - \frac{\text{cytokine production amount with addition of compound}}{\text{cytokine production amount without addition of compound}}\right) \times 100$$

Based on the dose-response curve obtained by plotting average value of cytokine production amount or inhibition rate in the longitudinal axis and concentration in the horizontal axis, the concentration ($IC_{50}$) of the compound that inhibits the level to 50% of the value of the control group is determined by nonlinear regression.

The compound of the present invention and a pharmaceutically acceptable salt thereof show a significant and concentration-dependent inhibitory activity as compared to the control group free of addition of the compound in the above-mentioned in vitro test.

EXPERIMENTAL EXAMPLE 4

Effect on JAK Phosphorylation

Mouse T cell strain CTLL-2 cells, D10.G4.1 cells or HT-2 cells are cultured in the presence of recombinant monkey IL-15 or recombinant mouse IL-2 for 24 hr. Then, lysis buffer is added and the obtained cell lysate is mixed with anti-JAK3 antibody (UBI) or anti-JAKI antibody (Santa Cruz) and protein A agarose at 4° C. for 2 hr to allow for immunoprecipitation. The immunoprecipitated protein is subjected to 7.5% SDS polyacrylamide gel electrophoresis and transferred to a PVDF membrane filter to perform western blotting. That is, after blocking with skim milk, the protein is blotted with an anti-phosphotyrosine antibody (4G10, UBI), a peroxidase-labeled anti-immunoglobulin antibody is added, a substrate is added to allow for color development, whose band is detected.

The compound of the present invention and a pharmaceutically acceptable salt thereof are found to inhibit phosphorylation of JAK1 or JAK3 in a concentration-dependent manner.

EXPERIMENTAL EXAMPLE 5

Action on Type II Collagen Induced Arthritis in DBA/1J Mouse

Arthritis was started by mixing an emulsion prepared by mixing bovine type II collagen (100–200 μg, purchased from collagen gijyutsukensyuukai) and Freund complete adjuvant (Sigma) containing killed *Mycobacterium tuberculosis* H37Ra, and subcutaneously giving to the tail base of 6 to 7-week-old male DBA/1J mouse (Charles River Japan, Inc.) twice at 3 weeks' intervals for immunization. The compound of the present invention or a pharmaceutically acceptable salt thereof was suspended or dissolved in 0.5% hydroxypropylmethyl cellulose and repeatedly administered orally at a dose of 0.01–100 mg/kg body weight using an oral sonde for 6 weeks from the first day of immunization. In this model, the symptom of arthritis of the limbs was each evaluated according to the following evaluation criteria of 0 to 4 scores. The score of arthritis of each mouse was shown by the total of the scores of the limbs (maximum: 16 points), wherein the total score of 1 or above was judged to indicate onset of arthritis.

| score | symptom |
| --- | --- |
| 0 | No change |
| 1 | edema in only one joint |
| 2 | edema in 2 or more joints (light edema of the entire limb) |
| 3 | severe edema of the entire limb |
| 4 | severe edema of the entire limb, and ankylosis and immovability of joint |

The thickness of the limbs of the mouse was measured using vernier calipers and the total of the thickness of the limbs was calculated and used as an index of arthritis. Moreover, an X-ray photograph of the limbs was taken with a soft-X ray equipment Softex (Omic) and the level of joint destruction was evaluated.

The arthritis score, total thickness of limbs and joint destruction score are shown in the average value and standard error for each group (n=5–10). Using a group, to which only a vehicle was given, as a control, statistical analysis was done according to the nonparametric or parametric Dunnett's method. When the p value was not more than 0.05, the case was judged to be significant.

The compound of the present invention and a pharmaceutically acceptable salt thereof showed significant and dose-dependent improvement in the above-mentioned in vivo test by repeated administration of 0.1–100 mg/kg body weight, as regards severity of developed arthritis, swelling of the limbs and destruction of joint, as compared to the control group, to which only a vehicle was given, and was clarified to markedly inhibit the onset and progress of arthritis.

In contrast, 1-(4-fluorophenyl)-N-(4-trifluoromethylphenyl)-5-methylpyrazole-4-carboxamide described in Bioorganic and Medicinal Chemistry Letters, vol. 8, pp. 2787–2792 (1998) did not improve the severity of the developed arthritis, swelling of the limbs or destruction of joint by repeated oral administration at the dose of 10 mg/kg body weight, and repeated oral administration at the dose of 30 mg/kg body weight resulted in confirmed death.

EXPERIMENTAL EXAMPLE 6

Effect and Life Prolonging Effect on Lupus Nephritis in Systemic Lupus Erythematosus Spontaneously Onset Model MRL/MpJ-lpr/lpr Mouse The compound of the present invention or a pharmaceutically acceptable salt thereof is suspended or dissolved in 0.5% hydroxypropylmethyl cellulose and repeatedly administered orally to 8–16 weeks old male MRL/MpJ-lpr/lpr mouse (Charles River Japan, Inc.) at a dose of 0.01–100 mg/kg body weight using an oral sonde every day. The survival rate during the administration period is recorded and blood and urine are taken with the lapse of time and antinuclear antibody titer and rheumatism in plasma, and protein amount in urine are measured. The repeated oral administration of the compound of the present invention or a pharmaceutically acceptable salt thereof at a dose of 0.1–100 mg/kg body weight in the above-mentioned in vivo test results in remarkable decrease in the incidence of proteinuria and protein concentration in urine, thus showing inhibition of the onset of lupus nephritis and improvement of symptoms in MRL/MpJ-lpr/lpr mouse. The compound of the present invention and a pharmaceutically acceptable salt thereof are confirmed to show a life prolonging effect by long-term administration to MRL/MpJ-lpr/lpr mouse.

EXPERIMENTAL EXAMPLE 7

Action on Egg Albumin Induced Mouse Biphasic Ear Edema

Physiological saline (0.5 ml) containing egg albumin 10 μg (Sigma) and aluminum hydroxide gel (1 mg) was intraperitoneally given to 6 to 7-week-old male BALB/c mouse (Charles River Japan, Inc.) for immunization. Two weeks later, egg albumin (5 μg) was intradermally injected into the auricular region of the mouse to induce biphasic ear edema 1 hr and 24 hr after the test. The compound of the present invention or a pharmaceutically acceptable salt thereof was suspended or dissolved in 0.5% hydroxypropylmethyl cellulose and repeatedly administered orally at a dose of 0.01–100 mg/kg body weight using an oral sonde for 3 days from two days prior to antigen challenge to the very day of the challenge. In this model, the thickness of the auricular region was measured with a dialing gauge and used as an index of ear edema.

The thickness of the auricular region was shown in the average value and standard error of each group (n=5–10), and using a group, to which only a vehicle was given, as a control, statistically analyzed according to the Dunnett's method. When the p value was not more than 0.05, the case was judged to be significant.

In the above-mentioned in vivo test, the compound of the present invention or a pharmaceutically acceptable salt thereof significantly and dose-dependently inhibited induction of edema in a late phase of 24 hr after challenging by repeated oral administration of 0.1–100 mg/kg body weight, as compared to the control group, to which only a vehicle was given, and suggested to inhibit allergic response in which type 2 helper T cell is involved.

EXPERIMENTAL EXAMPLE 8

Inhibitory Activity on Rat Experimental Autoimmune Encephalomyelitis

An emulsion (0.1 ml) prepared by mixing a myelin basic protein (100 μg, Sigma) and Freund complete adjuvant (Sigma) containing killed *Mycobacterium tuberculosis* H37Ra is intradermally given to a right hind-limb footpad of 6-week-old female LEW rat for immunization, and time course physical changes after immunization are evaluated according to the following 6 criteria.

| score | symptom |
|---|---|
| 0 | no symptom |
| 1 | weak tail |

| score | symptom |
|---|---|
| 2 | weak hind-limb |
| 3 | paralysis of one hind-limb |
| 4 | paralysis of both hind-limb |
| 5 | incontinence or death |

In the above-mentioned in vivo test, the compound of the present invention or a pharmaceutically acceptable salt thereof is confirmed to remarkably inhibit the onset and progress of autoimmune encephalomyelitis by repeated oral administration at a dose of 0.01–100 mg/kg body weight.

EXPERIMENTAL EXAMPLE 9

Test of Effect by Combined Use

According to the method of B. D. Kahan et al. [Transplantation, vol. 55, pp. 849–900 (1993)], the effect in the combined use group is calculated based on the dose-response curve by single administration of each of the test compound (two or more agents) and the combination index is determined. It is defined that the combination index of 1 means an additive action, the combination index of less than 1 means a synergistic action and the combination index of greater than 1 means an antagonistic action.

In the above-mentioned combined use effect test, the compound of the present invention or a pharmaceutically acceptable salt thereof show a combination index of smaller than 1 when used concurrently with one or more pharmaceutical agents selected from antirheumatic drug, immunosuppressant and steroidal drug or nonsteroidal antiinflammatory drug, thereby confirming a synergistic action.

EXPERIMENTAL EXAMPLE 10

Toxicity Test

In a single administration toxicity test, the test compound is administered to male and female SD rats (3 per group) and beagle (1 per group) and the toxicity by single administration is evaluated using the presence or absence of death incident, general condition and body weight as indices. In a repeat administration toxicity test, the test compound is repeatedly administered to male and female SD rats (6 per group) and male and female beagle (2 per group) for 2 weeks and the toxicity of the test compound by repeat administration is evaluated using general condition, body weight, diet intake, hematological test, biochemical test for blood, weight of organs and autopsy (including pathological test of tissues) as indices.

EXPERIMENTAL EXAMPLE 11

Evaluation of Bioavailability in Rat

The test compound is intravenously and orally administered-to male SD rats (4 per group), and the blood is drawn with the lapse of time. Using high performance liquid chromatography, the drug concentration in plasma is measured. The bioavailability (BA) is calculated by the following formula.

$$\frac{AUC \text{ by oral administration}}{AUC \text{ by intravenous administration}} \times \frac{\text{dose of intravenous administration}}{\text{dose of oral administration}} \times 100(\%)$$

AUC: plasma concentration—area under time curve

INDUSTRIAL APPLICABILITY

As is clear from the above-mentioned pharmacological tests, toxicity test and the like, because the compound of the present invention and a pharmaceutically acceptable salt, thereof show a superior inhibitory effect on the proliferation of activated lymphocyte, particularly inhibitory effects on the proliferation of IL-2, IL-4, IL-7, IL-9, IL-13 or IL-15-dependent activated lymphocyte, and also suppress the production of IL-15 and inflammatory cytokines derived from IL-15 and show a superior effect in arthritis model and autoimmune disease model, they are useful as agents for the prophylaxis or treatment of various autoimmune diseases.

This application is based on a patent application No. 241934/2000 filed in Japan, the contents of which are hereby incorporated by reference.

What is claimed is:

1. A fused bicyclic amide compound represented by the formula (I)

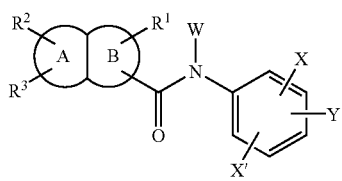

wherein $R^1$ is hydrogen, alkyl, halogen, hydroxyl group or alkoxy;

$R^2$ and $R^3$ are the same or different and each is hydrogen, alkyl or halogen;

ring A is benzene or cyclohexane, represented by one of the following formulas:

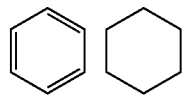

ring B is pyrrole or a derivative thereof, furan or thiophene, represented by one of the following formulas:

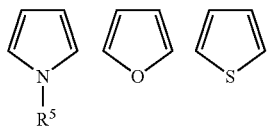

wherein $R^5$ is hydrogen, alkyl, alkoxycarbonylalkyl, hydroxycarbonylalkyl, acyloxyalkyl or hydroxyalkyl;

W is hydrogen, alkyl or hydroxycarbonylalkyl;

X is cyano;

X' is hydrogen; and

Y is piperidine having at least one substituent selected from the group consisting of hydroxy; carboxy; alkoxycarbonyl; hydroxyalkyl; alkoxyalkoxy; carboxyalkylcarbonyloxy; acyloxy; benzoyloxy; phenyl; alkylenedioxy; oxo; amino optionally mono- or di- substituted by alkoxyalkyl; cyclic amine selected from piperidine optionally having substituent, morpholine, thiomorpholine, and piperazine optionally having substituent (wherein the cyclic amine may be N-oxide); and morpholinomethyl;

or a pharmaceutically acceptable salt thereof.

2. The fused bicyclic amide compound of claim 1, wherein X is cyano that substitutes the 3-position of the phenyl group, or a pharmaceutically acceptable salt thereof.

3. The fused bicyclic amide compound of claim 1, wherein X is cyano that substitutes the 3-position of the phenyl group, and Y substitutes the 4-position of the phenyl group, or a pharmaceutically acceptable salt thereof.

4. The fused bicyclic amide compound of claim 1, which is selected from

N-[3-cyano-4-(4-hydroxypiperidin-1-yl)phenyl]-5-fluoro-2-methyl-1H-indole-3-carboxamide, N-[3-cyano-4-(4-hydroxypiperidin-1-yl)phenyl]benzo[b]thiophene-2-carboxamide, and N-{3-cyano-4-[4-(2-hydroxyethyl)piperidin-1-yl]phenyl}benzo[b]furan-2-carboxamide, or a pharmaceutically acceptable salt thereof.

5. A pharmaceutical composition comprising the fused bicyclic amide compound of any of claim 1, 2, 3 to claim 4 or a pharmaceutically acceptable salt thereof, and a pharmaceutically acceptable carrier.

6. A method for the or treatment of a disease caused by the proliferation of lymphocyte, which comprises administering an effective amount of the fused bicyclic amide compound of any one of claim 1, 2, 3 or 4 or a pharmaceutically acceptable salt thereof to a subject in need thereof.

7. The method of claim 6, wherein the disease is an autoiminune disease.

8. A method of inhibiting proliferation of activated lymphocycle, which comprises administering an effective amount of a fused bicyclic amide compound according to claim 1, or a pharmaceutically acceptable salt thereof, to a subject in need thereof.

9. The method of claim 6, wherein the disease is rheumatoid arthritis.

10. The method of claim 6, wherein the disease is an inflammatory, proliferative or hyper-proliferative skin disease.

11. The method of claim 6, wherein the disease is an immunity-mediated skin disease.

12. The method of claim 6, wherein the disease is atopic dermatitis.

* * * * *